United States Patent
Vallone et al.

(10) Patent No.: US 7,371,537 B2
(45) Date of Patent: *May 13, 2008

(54) MODULATORS OF B-LYMPHOCYTE ACTIVATION, MYOSIN-1F COMPOSITIONS AND METHODS OF USE

(75) Inventors: Marcy K. Vallone, San Francisco, CA (US); Brian R. Wong, San Mateo, CA (US); Esteban Masuda, Menlo Park, CA (US); Mark Powell, Burlingame, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/116,725

(22) Filed: Apr. 27, 2005

(65) Prior Publication Data

US 2005/0191719 A1  Sep. 1, 2005

Related U.S. Application Data

(63) Continuation of application No. 10/202,481, filed on Jul. 23, 2002, now Pat. No. 6,890,725.

(51) Int. Cl.
*C02K 1/00* (2006.01)
*G01N 33/53* (2006.01)

(52) U.S. Cl. .............................. 435/7.24; 435/4; 435/6; 435/7.21; 435/21

(58) Field of Classification Search .............. 435/7.21, 435/7.24, 21, 4, 6
See application file for complete search history.

(56) References Cited

U.S. PATENT DOCUMENTS

| | | | |
|---|---|---|---|
| 4,987,084 A * | 1/1991 | Tedder et al. | 436/63 |
| 5,969,102 A | 10/1999 | Bram et al. | |
| 6,160,010 A | 12/2000 | Uckun et al. | |
| 6,808,906 B2 * | 10/2004 | Shen et al. | 435/91.41 |
| 6,890,725 B2 * | 5/2005 | Vallone et al. | 435/7.24 |
| 7,122,332 B2 * | 10/2006 | Wong et al. | 435/7.8 |
| 2005/0191719 A1 * | 9/2005 | Vallone et al. | 435/18 |

OTHER PUBLICATIONS

Crozet, et al., "Cloning of the Genes Encoding Two Murine and Human Cochlear Unconventional Type I Myosins," *Genomics*, 1997, vol. 40, pp. 332-341.

* cited by examiner

*Primary Examiner*—David A. Saunders
(74) *Attorney, Agent, or Firm*—Klarquist Sparkman, LLP

(57) ABSTRACT

The present invention provides compositions and methods for modulating B-lymphocyte activation. Nucleic acids encoding proteins and proteins so encoded which are capable of modulating B-lymphocyte activation are provided. Compositions and methods for the treatment of disorders related to dysfunction or dysregulation of B-lymphocyte activation are also provided. Prophylactics and methods for the prevention of such disorders are also provided. Also provided are compositions and methods for diagnostic and prognostic determination of such disorders. Further provided are assays for the identification of bioactive agents capable of modulating B-lymphocyte activation.

8 Claims, 10 Drawing Sheets

```
   1   attcaggagc ctccaggagc ccagacacca gcccccacc atgggcagca aggagcgctt
  61   ccactggcag agccacaacg tgaagcagag cggcgtggat gacatggtgc ttcttcccca
 121   gatcaccgaa gacgccattg ccgccaacct ccggaagcgc ttcatggacg actacatctt
 181   cacctacatc ggctctgtgc tcatctctgt aaaccccttc aagcagatgc cctacttcac
 241   cgaccgtgag atcgacctct atcagggcgc ggcccagtat gagaatcctc gcacatcta
 301   cgccctcacg gacaacatgt accggaacat gcttatcgac tgtgagaacc agtgtgtcat
 361   cattagtgga gagagtggag ctgggaagac agtggcagcc aaatatatca tgggctacat
 421   ctccaaggtg tctggcggag gcgagaaggt ccagcacgtc aaagatatca tcctgcagtc
 481   caacccgctg ctcgaggcct tcggcaacgc caagactgtg cgcaacaaca attccagccg
 541   ctttggcaag tactttgaga tccagttcag ccgaggtggg gagccagatg ggggcaagat
 601   ctccaacttc ttgctggaga agtcccgcgt ggtcatgcaa aatgaaaatg agaggaactt
 661   ccacatctac taccagctgc tggaaggggc ctcccaggag caaaggcaga acctgggcct
 721   catgacaccg gactactatt actacctcaa ccaatcggac acctaccagg tggacggcac
 781   ggacgacaga agcgactttg gtgagactct gagtgctatg caggttattg ggatcccgcc
 841   cagcatccag cagctggtcc tgcagctcgt ggcggggatc ttgcacctgg ggaacatcag
 901   tttctgtgaa gacgggaatt acgcccgagt ggagagtgtg gacctcctgg cctttcccgc
 961   ctacctgctg ggcattgaca gcgggcgact gcaggagaag ctgaccagcc gcaagatgga
1021   cagccgctgg ggcgggcgca gcgagtccat caatgtgacc ctcaacgtgg agcaggcagc
1081   ctacacccgt gatgccctgg ccaaggggct ctatgcccgc ctcttcgact cctcgtgga
1141   ggccatcaac cgtgctatgc agaaacccca ggaagagtac agcatcggtg tgctggacat
1201   ttacggcttc gagatcttcc agaaaaatgg cttcgagcag ttttgcatca cttcgtcaa
1261   tgagaagctg cagcaaatct ttatcgaact taccctgaag gccgagcagg aggagtatgt
1321   gcaggaaggc attcgctgga ctccaatcca gtacttcaac aacaaggtcg tctgtgacct
1381   catcgaaaac aagctgagcc ccccaggcat catgagcgtc ttggacgacg tgtgcgccac
1441   catgcacgcc acgggcgggg gagcagacca gacactgctg cagaagctgc aggcggctgt
1501   ggggacccac gagcatttca acagctggag cgccggcttc gtcatccacc actacgctgg
1561   caaggtctcc tacgacgtca gcggcttctg cgagaggaac cgagacgttc tcttctccga
1621   cctcatagag ctgatgcaga ccagtgagca ggccttcctc cggatgctct ccccgagaa
1681   gctggatgga gacaagaagg ggcgccccag caccgccggc tccaagatca gaaacaagc
1741   caacgacctg gtggccacac tgatgaggtg cacaccccac tacatccgct gcatcaaacc
1801   caacgagacc aagcacgccc gagactggga ggagaacaga gtcaagcacc aggtggaata
1861   cctgggcctg aaggagaaca tcagggtgcg cagagccggc ttcgcctacc gccgccagtt
1921   cgccaaattc ctgcagaggt atgccattct gaccccgag acgtggccgc ggtggcgtgg
1981   ggacgaacgc cagggcgtcc agcacctgct tcgggcggtc aacatggagc ccgaccagta
2041   ccagatgggg agcaccaagg tctttgtcaa gaacccagag tcgcttttcc tcctggagga
2101   ggtgcgagag cgaaagttcg atggctttgc ccgaaccatc agaaggcct ggcggcgcca
2161   cgtggctgtc cggaagtacg aggagatgcg ggaggaagct ccaacatcc tgctgaacaa
2221   gaaggagcgg aggcgcaaca gcatcaatcg gaacttcgtc ggggactacc tggggctgga
2281   ggagcggccc gagctgcgtc agttcctggg caagaaggag cgggtggact cgccgattc
2341   ggtcaccaag tacgaccgcc gcttcaagcc catcaagcgg gacttgatcc tgacgcccaa
2401   gtgtgtgtat gtgattgggc gagagaaaat gaagaaggga cctgagaagg gccaggtgtg
2461   tgaagtcttg aagaagaaag tggacatcca ggctctgcgg ggagtctccc tcagcacgcg
2521   acaggacgac ttcttcatcc tccaagagga tgccgcgac agcttcctgg agagcgtctt
2581   caagaccgag tttgtcagcc ttctgtgcaa gcgcttcgag gaggcgacgc ggaggccct
2641   gccccctcacc ttcagcgaca cactacagtt tcgggtgaag aaggagggct ggggcggtgg
2701   cggcacccgc agcgtcacct ctctcccgcgg cttcggcgac ttggcagtgc tcaaggttgg
2761   cggtcggacc ctcacggtca gcgtgggcga tgggctgccc aagagctcca agcctacgcg
```

FIG._1A

```
2821 gaagggaatg gccaagggaa aacctcggag gtcgtcccaa gcccctaccc gggcggcccc
2881 tgcgccgccc agaggcatgg atcgcaatgg ggtgccgccc tctgccagag ggggccccct
2941 gcccctggag atcatgtctg gagggggcac ccacaggcct ccccggggcc ctccgtccac
3001 atccctggga gccagcagac gaccccgggc acgtccgccc tcagagcaca acacagaatt
3061 cctcaacgtg cctgaccagg gcatggccgg catgcagagg aagcgcagcg tggggcaacg
3121 gccagtgcct ggtgtgggcc gacccaagcc ccagcctcgg acacatggtc ccaggtgccg
3181 ggccctatac cagtacgtgg gccaagatgt ggacgagctg agcttcaacg tgaacgaggt
3241 cattgagatc ctcatggaag atccctcggg ctggtggaag ggccggcttc acggccagga
3301 gggccttttc ccaggraact acgtggagaa gatctgagct gggccctggg atactgcctt
3361 ctctttcgcc cgcctatctg cctgccggcc tggtggggag ccaggccctg ccaatgagag
3421 cctcgtttac ctgggctgca atagcctaaa agtccagtcc tttggcctcc agtcctgccc
3481 aggccctggg tcaccaggtc actgctgcag ccccgcccc tgggccctgg tcttcctcca
3541 acatcacacc tgctgcccat tctccatttc tgtgtgtgtc aaaggggact aacagcagaa
3601 tctacctccc aactgcc
```

Human Myosin-1F
cds 41-3337

FIG._1B

```
   1  mgskerfhwq shnvkqsgvd dmvllpqite daiaanlrkr fmddyiftyi gsvlisvnpf
  61  kqmpyftdre idlyqgaaqy enpphiyalt dnmyrnmlid cenqcviisg esgagktvaa
 121  kyimgyiskv sgggekvqhv kdiilqsnpl leafgnaktv rnnnssrfgk yfeiqfsrgg
 181  epdggkisnf lleksrvvmq nenernfhiy yqllegasqe qrqnlglmtp dyyyylnqsd
 241  tyqvdgtddr sdfgetlsam qvigippsiq qlvlqlvagi lhlgnisfce dgnyarvesv
 301  dllafpayll gidsgrlqek ltsrkmdsrw ggrsesinvt lnveqaaytr dalakglyar
 361  lfdflveain ramqkpqeey sigvldiygf eifqkngfeq fcinfvnekl qqifieltlk
 421  aeqeeyvqeg irwtpiqyfn nkvvcdlien klsppgimsv lddvcatmha tgggadqtll
 481  qklqaavgth ehfnswsagf vihhyagkvs ydvsgfcern rdvlfsdlie lmqtseqafl
 541  rmlfpekldg dkkgrpstag skikkqandl vatlmrctph yircikpnet khardweenr
 601  vkhqveylgl kenirvrrag fayrrqfakf lqryailtpe twprwrgder qgvqhllrav
 661  nmepdqyqmg stkvfvknpe slflleevre rkfdgfarti qkawrrhvav rkyeemreea
 721  snilInkker rrnsinrnfv gdylgleerp elrqflgkke rvdfadsvtk ydrrfkpikr
 781  dliltpkcvy vigrekmkkg pekgqvcevl kkkvdiqalr gvslstrqdd ffilqedaad
 841  sflesvfkte fvsllckrfe eatrrplplt fsdtlqfrvk kegwggggtr svtfsrgfgd
 901  lavlkvggrt ltvsvgdglp ksskptrkgm akgkprrssq aptraapapp rgmdrngvpp
 961  sarggplple imsgggthrp prgppstslg asrrprarpp sehnteflnv pdqgmagmqr
1021  krsvgqrpvp gvgrpkpqpr thgprcraly qyvgqdvdel sfnvneviei lmedpsgwwk
1081  grlhgqeglf pgnyveki
```

Human myosin-1F
IQ motif in bold conserved DALAK sequence shown in italics and underlined
phosphorylation site serine in bold upstream of DALAK sequence

FIG._2

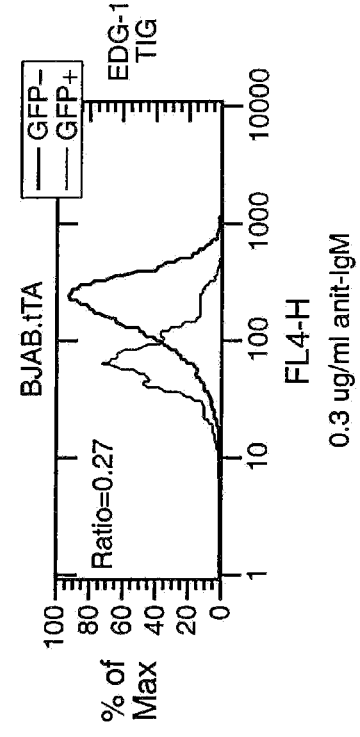
FIG._3B
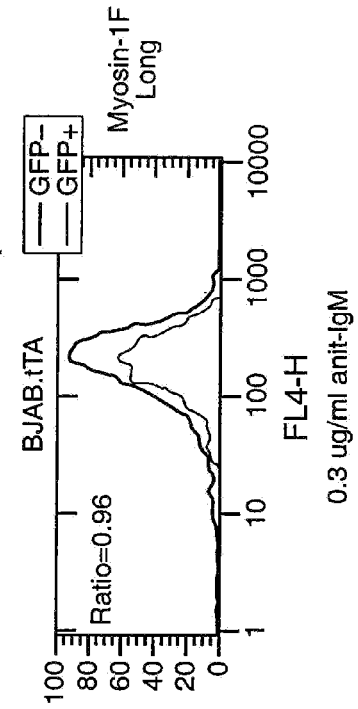
FIG._3D
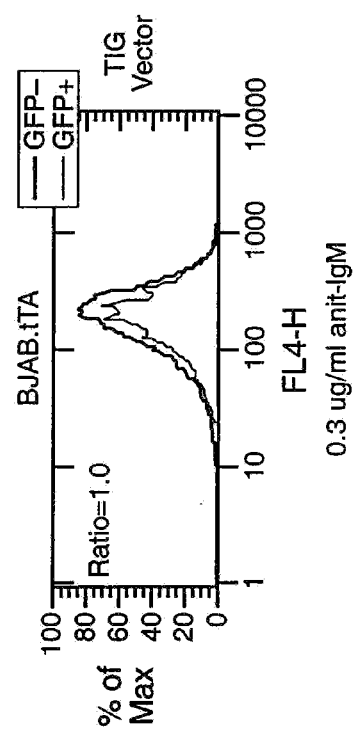
FIG._3A
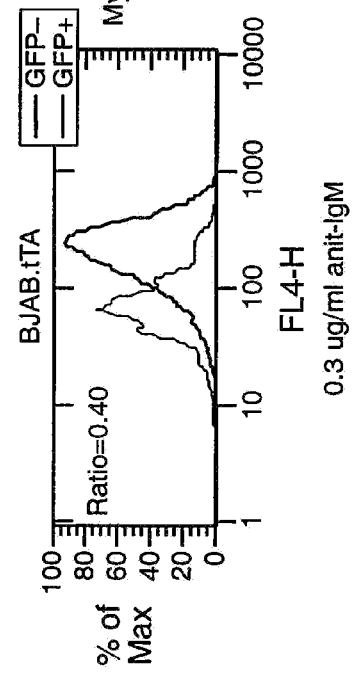
FIG._3C

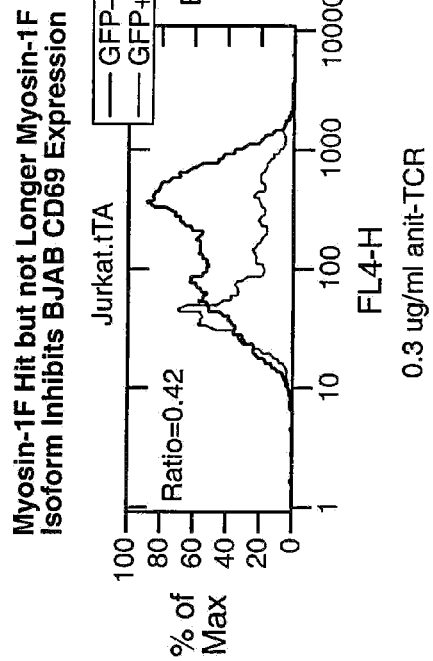
FIG._3E
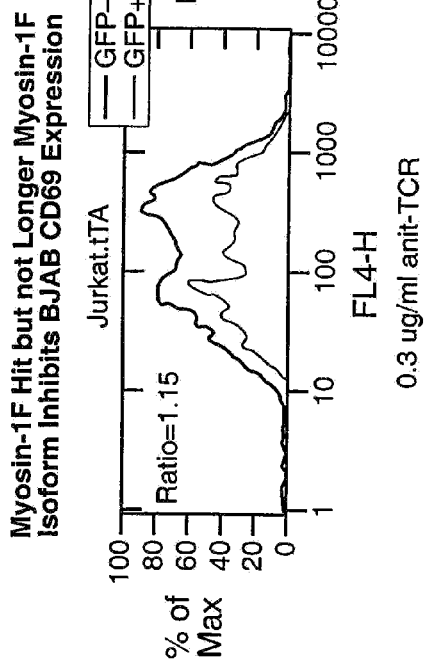
FIG._3F
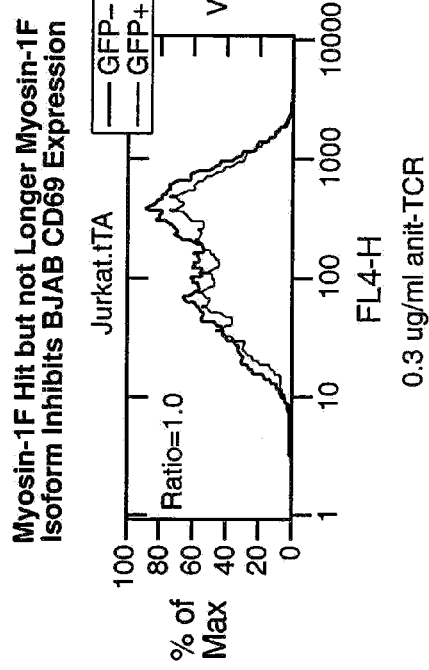
FIG._3G
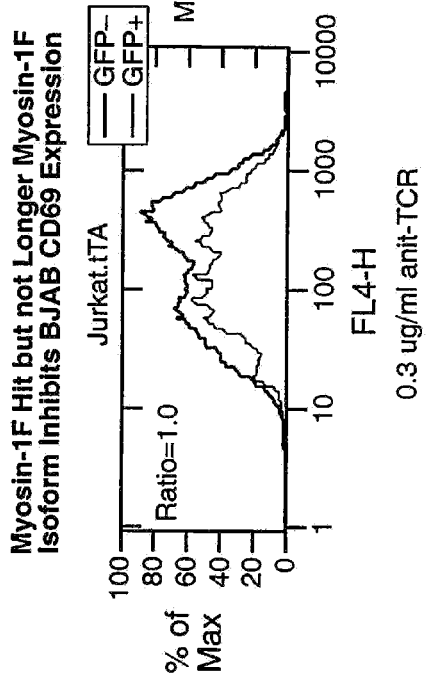
FIG._3H

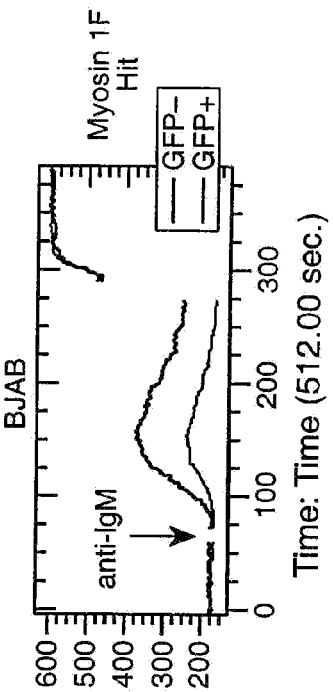
FIG._4A
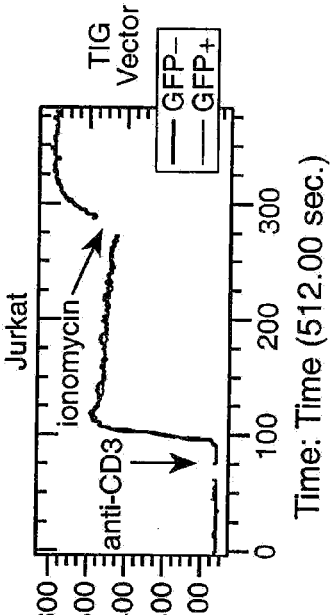
FIG._4B
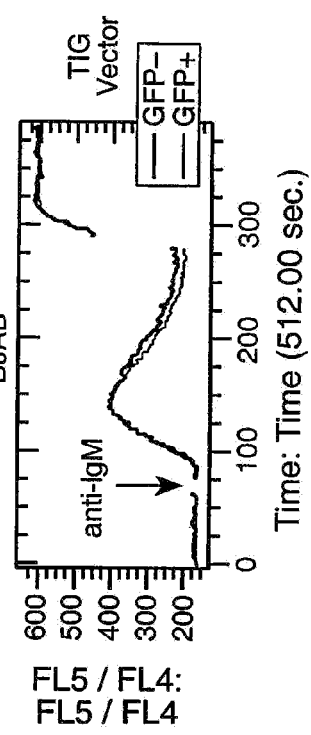
FIG._4C
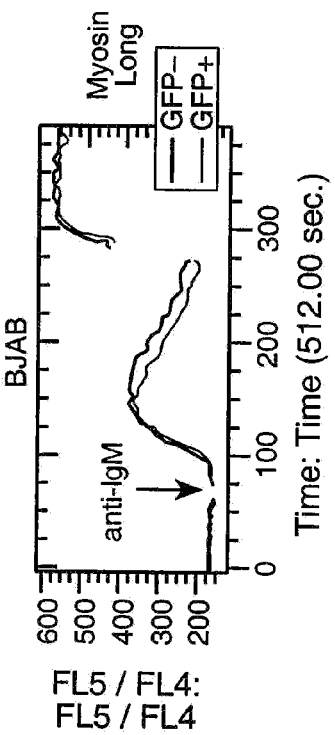
FIG._4D

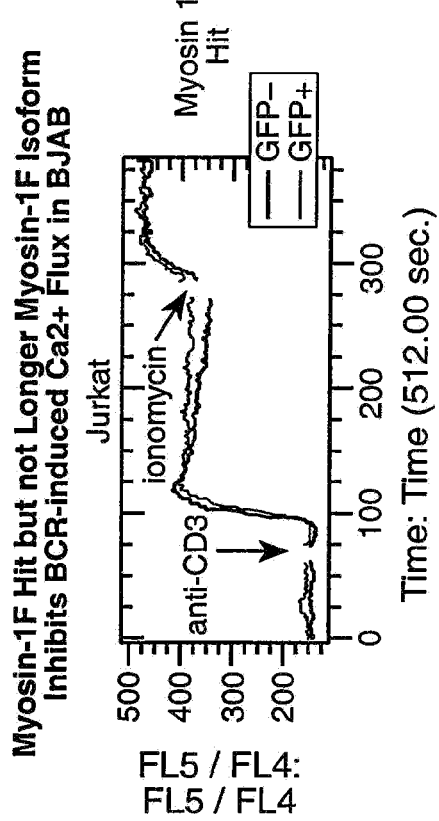
FIG.—4E
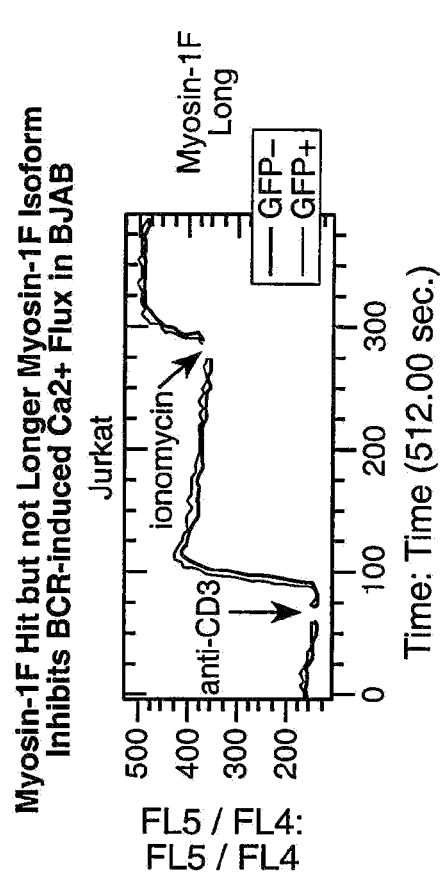
FIG.—4F

TABLE 1

Human Autoimmune Diseases

| Disease | Self-Antigen | Immune Response |
|---|---|---|
| *Organ-Specific Autoimmune Disease* | | |
| Addison's disease | Adrenal cells | Autoantibodies |
| Autoimmune hemolytic anemia | Red blood cells | Autoantibodies |
| Goodpasture's disease | Renal and lung membranes | Autoantibodies |
| Graves' disease | Thyroid-stimulating hormone receptor | Autoantibodies |
| Hashimoto's thyroiditis | Thyroid proteins | $T_{DTH}$ cells, autoantibodies |
| Idiopathic thrombocytopenia | Platelet membranes | Autoantibodies |
| Insulin-dependent diatetes mellitus (IDDM) | Pancreatic beta cells | $T_{DTH}$ cells, autoantibodies |
| Myasthenia gravis | Acetylcholine receptors | Autoantibodies |
| Myocardial infarction | Heart muscle | Autoantibodies |
| Pernicious anemia | Gastric intrinsic factor | Autoantibodies |
| Poststreptococcal glomerulonephritis | Kidney | Immune complexes |
| Spontaneous inferility | Sperm | Autoantibodies |
| *Systemic Autoimmune Disease* | | |
| Ankylosing spondylitis | Vertebrae | Immune complexes |
| Multiple sclerosis | Brain or white matter | $T_{DTH}$ and $T_c$ cells, autoantibodies |
| Rheumatoid arthritis | Connective tissue | Autoantibodies, immune complexes |
| Scleroderma | Nuclei, heart, lungs, GI tract, Kidney | Autoantibodies |
| Sjogren's syndrome | Salivary gland, liver, kidney, thyroid | Autoantibodies |
| Systemic lupus erythematosus (SLE) | DNA, nuclear protein, RBC and platelet membranes | Autoantibodies, immune complexes |

*FIG._5*

Myosin-1F: ATP Binding Site Alignment

```
                               70            80            90           100           110           120
                        *....|....*....|....*....|....*....|....*....|....*....|....*....|....*....|
Consensus                                                                                             
Myosin-1F, Human           ---RYE-------LPPHIFAIADEAYRSMLSDKENQSILISGESGAGKTENTKKKVM
Smooth Muscle Myosin, Chicken ---RHE-------DNMYRNMLIDCENQCVIISGESGAGKTVAAKYIM
Muscle Myosin, Mollusc     ---RHE-------MPPHIYAIADTAYRSMLQDREDQSILCTGESGAGKTENTKKVI
Myosin II, Dictyostelium   ---KTE-------IPPPHLFSVADNAYQNMVTDRENQSCLITGESGAGKTENTKKVI
Myosin-3 C.elegans         ---RNE-------VAPHIFAISDVAYRSMLDDRQNQSLLITGESGAGKTENTKKVI
Non-muscle Myosin, Drosophila ---RNE-------MPPHLFAVSDEAYRNMVQDKENQSMLITGESGAGKTENTKKVI
Myosin-II, Acanthamoeba    ---RHE-------VPPHVFAITDSAYRNMLGDREDQSILCTGESGAGKTENTKKVI
Myosin-4, Yeast            ---RDK-------VAPHIFAISDAAYRAMLNTRQNQSMLITGESGAFKTENTKKVI
Brush Border Myo-1, Bovine ---KDE-------LEPHLFAIAEEAYRFMVHEKANQTVVVSGESGAGKTVSAKYIM
                           ---FYE-------LKPHIYALANMAYQSLRDRDRDQCILITGESGAGKTEASKLVM
```

FIG._6

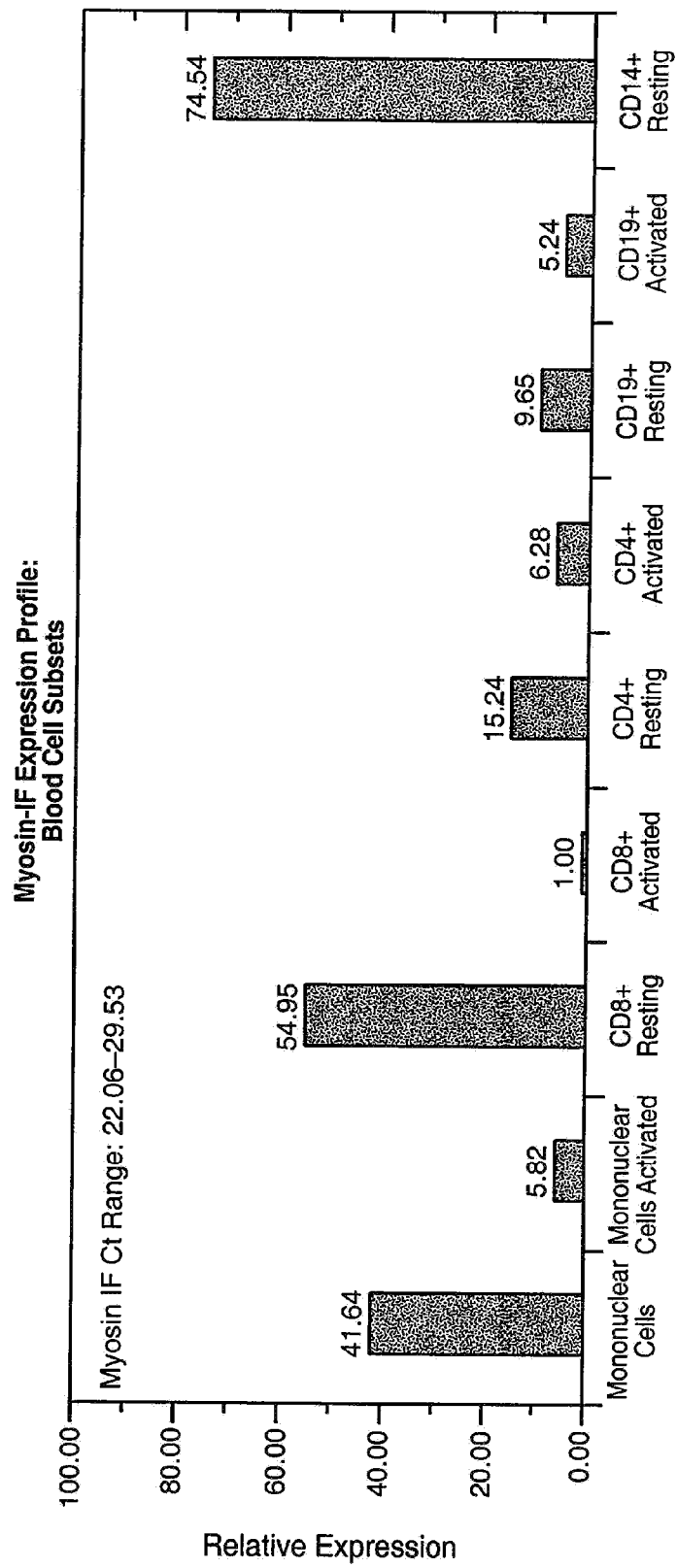
FIG._7A
FIG._7B

SEQUENCE LISTING

<160> NUMBER OF SEQ ID NOS: 15

<210> SEQ ID NO 1
<211> LENGTH: 3617
<212> TYPE: DNA
<213> ORGANISM: Homo sapiens

<400> SEQUENCE: 1

```
attcaggagc ctccaggagc ccagacacca gcccccacc atgggcagca aggagcgctt      60
ccactggcag agccacaacg tgaagcagag cggcgtggat gacatggtgc ttcttcccca     120
gatcaccgaa gacgccattg ccgccaacct ccggaagcgc ttcatggacg actacatctt     180
```

-continued

```
cacctacatc ggctctgtgc tcatctctgt aaacccttc aagcagatgc cctacttcac      240
cgaccgtgag atcgacctct atcagggcgc ggcccagtat gagaatcctc cgcacatcta      300
cgccctcacg gacaacatgt accggaacat gcttatcgac tgtgagaacc agtgtgtcat      360
cattagtgga gagagtggag ctgggaagac agtggcagcc aaatatatca tgggctacat      420
ctccaaggtg tctggcggag gcgagaaggt ccagcacgtc aaagatatca tcctgcagtc      480
caacccgctg ctcgaggcct tcggcaacgc caagactgtg cgcaacaaca attccagccg      540 cttttggcaag tactttgaga tccagttcag ccgaggtggg gagccagatg ggggcaagat      600
ctccaacttc ttgctggaga gtcccgcgt ggtcatgcaa aatgaaaatg agaggaactt      660
ccacatctac taccagctgc tggaaggggc ctcccaggag caaaggcaga acctgggcct      720
catgacaccg gactactatt actacctcaa ccaatcggac acctaccagg tggacggcac      780
ggacgacaga agcgactttg gtgagactct gagtgctatg caggttattg ggatcccgcc      840
cagcatccag cagctggtcc tgcagctcgt ggcggggatc ttgcacctgg ggaacatcag      900
tttctgtgaa gacgggaatt acgcccgagt ggagagtgtg gacctcctgg cctttcccgc      960
ctacctgctg ggcattgaca gcgggcgact gcaggagaag ctgaccagcc gcaagatgga     1020
cagccgctgg ggcgggcgca gcgagtccat caatgtgacc ctcaacgtgg agcaggcagc     1080
ctacacccgt gatgccctgg ccaagggggct ctatgcccgc ctcttcgact cctcgtgga     1140 ggccatcaac cgtgctatgc agaaacccca ggaagagtac agcatcggtg tgctggacat     1200
ttacggcttc gagatcttcc agaaaaatgg cttcgagcag ttttgcatca acttcgtcaa     1260
tgagaagctg cagcaaatct ttatcgaact taccctgaag gccgagcagg aggagtatgt     1320
gcaggaaggc attcgctgga ctccaatcca gtacttcaac aacaaggtcg tctgtgacct     1380
catcgaaaac aagctgagcc ccccaggcat catgagcgtc ttggacgacg tgtgcgccac     1440
catgcacgcc acgggcgggg gagcagacca gacactgctg cagaagctgc aggcggctgt     1500
ggggacccac gagcatttca acagctggag cgccggcttc gtcatccacc actacgctgg     1560
caaggtctcc tacgacgtca gcggcttctg cgagaggaac cgagacgttc tcttctccga     1620
cctcatagag ctgatgcaga ccagtgagca ggccttcctc cggatgctct ccccgagaa     1680 gctggatgga cacaagaagg ggcgccccag caccgccggc tccaagatca agaaacaagc     1740
caacgacctg gtggccacac tgatgagctg cacaccccac tacatccgct gcatcaaacc     1800
caacgagacc aagcacgccc gagactggga ggagaacaga gtcaagcacc aggtggaata     1860
cctgggcctg aaggagaaca tcagggtgcg cagagccggc ttcgcctacc gccgccagtt     1920
cgccaaattc ctgcagaggt atgccattct gaccccgag acgtggccgc ggtggcgtgg     1980
ggacgaacgc cagggcgtcc agcacctgct tcgggcggtc aacatggagc ccgaccagta     2040
ccagatgggg agcaccaagg tctttgtcaa gaacccagag tcgctttcc tcctggagga     2100 ggtgcgagag cgaaagttcg atggctttgc ccgaaccatc cagaaggcct ggcggcgcca     2160
cgtggctgtc cggaagtacg aggagatgcg ggaggaagct tccaacatcc tgctgaacaa     2220
gaaggagcgg aggcgcaaca gcatcaatcg gaacttcgtc ggggactacc tggggctgga     2280
ggagcggccc gagctgcgtc agttcctggg caagaaggag cgggtggact cgccgattc     2340 ggtcaccaag tacgaccgcc gcttcaagcc catcaagcgg acttgatcc tgcgcccaa     2400 gtgtgtgtat gtgattgggc gagagaaaat gaagaaggga cctgagaagg gccaggtgtg     2460
tgaagtcttg aagaagaaag tggacatcca ggctctgcgg ggagtctccc tcagcacgcg     2520
```

-continued

```
acaggacgac ttcttcatcc tccaagagga tgccgccgac agcttcctgg agagcgtctt    2580
caagaccgag tttgtcagcc ttctgtgcaa gcgcttcgag gaggcgacgc ggaggcccct    2640
gcccctcacc ttcagcgaca cactacagtt tcgggtgaag aaggagggct ggggcggtgg    2700
cggcacccgc agcgtcacct tctcccgcgg cttcggcgac ttggcagtgc tcaaggttgg    2760
cggtcggacc ctcacggtca gcgtgggcga tgggctgccc aagagctcca agcctacgcg    2820
gaagggaatg gccaagggaa acctcggag gtcgtcccaa gccccctaccc gggcggcccc    2880 tgcgccccccc agaggcatgg atcgcaatgg ggtgcccccc tctgccagag ggggcccccct   2940 gcccctggag atcatgtctg aggggggcac ccacaggcct ccccggggcc ctccgtccac    3000
atccctggga ccagcagac gaccccgggc acgtccgccc tcagagcaca acacagaatt    3060
cctcaacgtg cctgaccagg gcatggccgg catgcagagg aagcgcagcg tggggcaacg    3120
gccagtgcct ggtgtgggcc gacccaagcc ccagcctcgg acacatggtc ccaggtgccg    3180
ggccctatac cagtacgtgg gccaagatgt ggacgagctg agcttcaacg tgaacgaggt    3240
cattgagatc ctcatggaag atccctcggg ctggtggaag ggccggcttc acggccagga    3300 gggcctttc ccaggraact acgtggagaa gatctgagct gggccctggg atactgcctt    3360
ctctttcgcc cgcctatctg cctgccggcc tggtggggag ccaggccctg ccaatgagag    3420
cctcgtttac ctgggctgca atagcctaaa agtccagtcc tttggcctcc agtcctgccc    3480
aggccctggg tcaccaggtc actgctgcag ccccccgcccc tgggccctgg tcttcctcca    3540
acatcacacc tgctgcccat tctccatttc tgtgtgtgtc aaagggact aacagcagaa    3600 tctacctccc aactgcc                                                   3617
```

<210> SEQ ID NO 2
<211> LENGTH: 1098
<212> TYPE: PRT
<213> ORGANISM: Homo sapiens

<400> SEQUENCE: 2

```
Met Gly Ser Lys Glu Arg Phe His Trp Gln Ser His Asn Val Lys Gln
1               5                   10                  15

Ser Gly Val Asp Asp Met Val Leu Leu Pro Gln Ile Thr Glu Asp Ala
            20                  25                  30

Ile Ala Ala Asn Leu Arg Lys Arg Phe Met Asp Asp Tyr Ile Phe Thr
        35                  40                  45

Tyr Ile Gly Ser Val Leu Ile Ser Val Asn Pro Phe Lys Gln Met Pro
    50                  55                  60

Tyr Phe Thr Asp Arg Glu Ile Asp Leu Tyr Gln Gly Ala Ala Gln Tyr
65                  70                  75                  80

Glu Asn Pro Pro His Ile Tyr Ala Leu Thr Asp Asn Met Tyr Arg Asn
                85                  90                  95

Met Leu Ile Asp Cys Glu Asn Gln Cys Val Ile Ile Ser Gly Glu Ser
            100                 105                 110

Gly Ala Gly Lys Thr Val Ala Ala Lys Tyr Ile Met Gly Tyr Ile Ser
        115                 120                 125

Lys Val Ser Gly Gly Gly Glu Lys Val Gln His Val Lys Asp Ile Ile
    130                 135                 140

Leu Gln Ser Asn Pro Leu Leu Glu Ala Phe Gly Asn Ala Lys Thr Val
145                 150                 155                 160

Arg Asn Asn Asn Ser Ser Arg Phe Gly Lys Tyr Phe Glu Ile Gln Phe
                165                 170                 175
```

```
Ser Arg Gly Gly Glu Pro Asp Gly Gly Lys Ile Ser Asn Phe Leu Leu
            180                 185                 190

Glu Lys Ser Arg Val Val Met Gln Asn Glu Asn Arg Asn Phe His
        195                 200                 205

Ile Tyr Tyr Gln Leu Leu Glu Gly Ala Ser Gln Glu Gln Arg Gln Asn
    210                 215                 220

Leu Gly Leu Met Thr Pro Asp Tyr Tyr Tyr Leu Asn Gln Ser Asp
225                 230                 235                 240

Thr Tyr Gln Val Asp Gly Thr Asp Asp Arg Ser Asp Phe Gly Glu Thr
                245                 250                 255

Leu Ser Ala Met Gln Val Ile Gly Ile Pro Pro Ser Ile Gln Gln Leu
            260                 265                 270

Val Leu Gln Leu Val Ala Gly Ile Leu His Leu Gly Asn Ile Ser Phe
        275                 280                 285

Cys Glu Asp Gly Asn Tyr Ala Arg Val Glu Ser Val Asp Leu Leu Ala
    290                 295                 300

Phe Pro Ala Tyr Leu Leu Gly Ile Asp Ser Gly Arg Leu Gln Glu Lys
305                 310                 315                 320

Leu Thr Ser Arg Lys Met Asp Ser Arg Trp Gly Gly Arg Ser Glu Ser
                325                 330                 335

Ile Asn Val Thr Leu Asn Val Glu Gln Ala Ala Tyr Thr Arg Asp Ala
            340                 345                 350

Leu Ala Lys Gly Leu Tyr Ala Arg Leu Phe Asp Phe Leu Val Glu Ala
        355                 360                 365

Ile Asn Arg Ala Met Gln Lys Pro Gln Glu Glu Tyr Ser Ile Gly Val
    370                 375                 380

Leu Asp Ile Tyr Gly Phe Glu Ile Phe Gln Lys Asn Gly Phe Glu Gln
385                 390                 395                 400

Phe Cys Ile Asn Phe Val Asn Glu Lys Leu Gln Gln Ile Phe Ile Glu
                405                 410                 415

Leu Thr Leu Lys Ala Glu Gln Glu Glu Tyr Val Gln Glu Gly Ile Arg
            420                 425                 430

Trp Thr Pro Ile Gln Tyr Phe Asn Asn Lys Val Val Cys Asp Leu Ile
        435                 440                 445

Glu Asn Lys Leu Ser Pro Pro Gly Ile Met Ser Val Leu Asp Asp Val
    450                 455                 460

Cys Ala Thr Met His Ala Thr Gly Gly Gly Ala Asp Gln Thr Leu Leu
465                 470                 475                 480

Gln Lys Leu Gln Ala Ala Val Gly Thr His Glu His Phe Asn Ser Trp
                485                 490                 495

Ser Ala Gly Phe Val Ile His His Tyr Ala Gly Lys Val Ser Tyr Asp
            500                 505                 510

Val Ser Gly Phe Cys Glu Arg Asn Arg Asp Val Leu Phe Ser Asp Leu
        515                 520                 525

Ile Glu Leu Met Gln Thr Ser Glu Gln Ala Phe Leu Arg Met Leu Phe
    530                 535                 540

Pro Glu Lys Leu Asp Gly Asp Lys Lys Gly Arg Pro Ser Thr Ala Gly
545                 550                 555                 560

Ser Lys Ile Lys Lys Gln Ala Asn Asp Leu Val Ala Thr Leu Met Arg
                565                 570                 575

Cys Thr Pro His Tyr Ile Arg Cys Ile Lys Pro Asn Glu Thr Lys His
            580                 585                 590

Ala Arg Asp Trp Glu Glu Asn Arg Val Lys His Gln Val Glu Tyr Leu
```

-continued

```
                595                 600                 605
Gly Leu Lys Glu Asn Ile Arg Val Arg Arg Ala Gly Phe Ala Tyr Arg
    610                 615                 620

Arg Gln Phe Ala Lys Phe Leu Gln Arg Tyr Ala Ile Leu Thr Pro Glu
625                 630                 635                 640

Thr Trp Pro Arg Trp Arg Gly Asp Glu Arg Gln Gly Val Gln His Leu
                645                 650                 655

Leu Arg Ala Val Asn Met Glu Pro Asp Gln Tyr Gln Met Gly Ser Thr
                660                 665                 670

Lys Val Phe Val Lys Asn Pro Glu Ser Leu Phe Leu Leu Glu Glu Val
                675                 680                 685

Arg Glu Arg Lys Phe Asp Gly Phe Ala Arg Thr Ile Gln Lys Ala Trp
690                 695                 700

Arg Arg His Val Ala Val Arg Lys Tyr Glu Glu Met Arg Glu Glu Ala
705                 710                 715                 720

Ser Asn Ile Leu Leu Asn Lys Lys Glu Arg Arg Asn Ser Ile Asn
                725                 730                 735

Arg Asn Phe Val Gly Asp Tyr Leu Gly Leu Glu Glu Arg Pro Glu Leu
                740                 745                 750

Arg Gln Phe Leu Gly Lys Lys Glu Arg Val Asp Phe Ala Asp Ser Val
                755                 760                 765

Thr Lys Tyr Asp Arg Arg Phe Lys Pro Ile Lys Arg Asp Leu Ile Leu
                770                 775                 780

Thr Pro Lys Cys Val Tyr Val Ile Gly Arg Glu Lys Met Lys Lys Gly
785                 790                 795                 800

Pro Glu Lys Gly Gln Val Cys Glu Val Leu Lys Lys Val Asp Ile
                805                 810                 815

Gln Ala Leu Arg Gly Val Ser Leu Ser Thr Arg Gln Asp Asp Phe Phe
                820                 825                 830

Ile Leu Gln Glu Asp Ala Ala Asp Ser Phe Leu Glu Ser Val Phe Lys
                835                 840                 845

Thr Glu Phe Val Ser Leu Leu Cys Lys Arg Phe Glu Glu Ala Thr Arg
                850                 855                 860

Arg Pro Leu Pro Leu Thr Phe Ser Asp Thr Leu Gln Phe Arg Val Lys
865                 870                 875                 880

Lys Glu Gly Trp Gly Gly Gly Thr Arg Ser Val Thr Phe Ser Arg
                885                 890                 895

Gly Phe Gly Asp Leu Ala Val Leu Lys Val Gly Gly Arg Thr Leu Thr
                900                 905                 910

Val Ser Val Gly Asp Gly Leu Pro Lys Ser Ser Lys Pro Thr Arg Lys
                915                 920                 925

Gly Met Ala Lys Gly Lys Pro Arg Arg Ser Ser Gln Ala Pro Thr Arg
                930                 935                 940

Ala Ala Pro Ala Pro Pro Arg Gly Met Asp Arg Asn Gly Val Pro Pro
945                 950                 955                 960

Ser Ala Arg Gly Gly Pro Leu Pro Leu Glu Ile Met Ser Gly Gly Gly
                965                 970                 975

Thr His Arg Pro Pro Arg Gly Pro Pro Ser Thr Ser Leu Gly Ala Ser
                980                 985                 990

Arg Arg Pro Arg Ala Arg Pro Pro  Ser Glu His Asn Thr  Glu Phe Leu
                995                 1000                1005

Asn Val  Pro Asp Gln Gly Met  Ala Gly Met Gln Arg  Lys Arg Ser
    1010                1015                1020
```

```
Val Gly Gln Arg Pro Val Pro Gly Val Gly Arg Pro Lys Pro Gln
    1025                1030                1035

Pro Arg Thr His Gly Pro Arg Cys Arg Ala Leu Tyr Gln Tyr Val
    1040                1045                1050

Gly Gln Asp Val Asp Glu Leu Ser Phe Asn Val Asn Glu Val Ile
    1055                1060                1065

Glu Ile Leu Met Glu Asp Pro Ser Gly Trp Trp Lys Gly Arg Leu
    1070                1075                1080

His Gly Gln Glu Gly Leu Phe Pro Gly Asn Tyr Val Glu Lys Ile
    1085                1090                1095

<210> SEQ ID NO 3
<211> LENGTH: 2520
<212> TYPE: DNA
<213> ORGANISM: Homo sapiens

<400> SEQUENCE: 3
atgcaggtta ttgggatccc gcccagcatc cagcagctgg tcctgcagct cgtggcgggg      60
atcttgcacc tggggaacat cagtttctgt gaagacggga attacgcccg agtggagagt     120
gtggacctcc tggcctttcc cgcctacctg ctgggcattg acagcgggcg actgcaggag     180
aagctgacca gccgcaagat ggacagccgc tgggcgggc gcagcgagtc catcaatgtg      240
accctcaacg tggagcaggc agcctacacc cgtgatgccc tggccaaggg gctctatgcc     300
cgcctcttcg acttcctcgt ggaggccatc aaccgtgcta gcagaaacc ccaggaagag      360 tacagcatcg gtgtgctgga catttacggc ttcgagatct ccagaaaaa tggcttcgag      420 cagttttgca tcaacttcgt caatgagaag ctgcagcaaa tctttatcga acttaccctg     480
aaggccgagc aggaggagta tgtgcaggaa ggcattcgct ggactccaat ccagtacttc     540
aacaacaagg tcgtctgtga cctcatcgaa aacaagctga ccccccagg catcatgagc      600 gtcttggacg acgtgtgcgc caccatgcac gccacgggcg ggggagcaga ccagacactg     660
ctgcagaagc tgcaggcggc tgtggggacc acgagcatt tcaacagctg gagcgccggc     720
ttcgtcatcc accactacgc tggcaaggtc tcctacgacg tcagcggctt ctgcgagagg     780
aaccgagacg ttctcttctc cgacctcata gagctgatgc agaccagtga gcaggccttc     840
ctccggatgc tcttccccga gaagctggat ggagacaaga aggggcgccc cagcaccgcc     900
ggctccaaga tcaagaaaca agccaacgac ctggtggcca cactgatgag gtgcacaccc     960
cactacatcc gctgcatcaa acccaacgag accaagaggc cccgagactg ggaggagaac    1020
agagtcaagc accaggtgga atacctgggc ctgaaggaga acatcagggt gcgcagagcc    1080
ggcttcgcct accgccgcca gttcgccaaa ttcctgcaga ggtatgccat ctctgacccc    1140
gagacgtggc gcggtggcg tggggacgaa cgccagggcg tccagcacct gcttcgggcg    1200
gtcaacatga gcccgacca gtaccagatg gggagcacca aggtctttgt caagaaccca    1260
gagtcgcttt tcctcctgga ggaggtgcga gagcgaaagt tcgatggctt tgcccgaacc    1320
atccagaagg cctggcggcg ccacgtggct gtccggaagt acgaggagat gcgggaggaa    1380
gcttccaaca tcctgctgaa caagaaggag cggaggcgca acagcatcaa tcggaacttc    1440 gtcgggact acctggggct ggaggagcgg cccgagctgc gtcagttcct gggcaagagg    1500
gagcgggtgg acttcgccga ttcggtcacc aagtacgacc gccgcttcaa gccccatcaag    1560 cgggacttga tcctgacgcc caagtgtgtg tatgtgattg gcgagagaa agtgaagaag    1620 ggacctgaga agggccaggt gtgtgaagtc ttgaagaaga agtggacat ccaggctctg    1680
```

```
cggggagtct ccctcagcac gcgacaggac gacttcttca tcctccaaga ggatgccgcc    1740
gacagcttcc tggagagcgt cttcaagacc gagtttgtca gccttctgtg caagcgcttc    1800
gaggaggcga cgcggaggcc cctgcccctc accttcagcg acacactaca gtttcgggtg    1860
aagaaggagg gctggggcgg tggcggcacc cgcagcgtca ccttctcccg cggcttcggc    1920
gacttggcag tgctcaaggt tggcggtcgg accctcacgg tcagcgtggg cgatgggctg    1980
cccaagagct ccaagcctac gcggaaggga atggccaagg aaaacctcg gaggtcgtcc     2040 caagccccta cccgggcggc ccctgcgccc ccagaggca tggatcgcaa tggggtgccc     2100
ccctctgcca gagggggccc cctgcccctg gagatcatgt ctggaggggg cacccacagg    2160
cctccccggg gccctccgtc cacatccctg ggagccagca gacgaccccg gcacgtccg     2220 ccctcagagc acaacacaga attcctcaac gtgcctgacc agggcatggc cggcatgcag    2280
aggaagcgca gcgtggggca acggccagtg cctggtgtgg gccgacccaa gccccagcct    2340
cggacacatg gtcccaggtg ccgggcccta taccagtacg tgggccaaga tgtggacgag    2400
ctgagcttca cgtgaacga ggtcattgag atcctcatgg aagatccctc gggctggtgg     2460
aagggccggc ttcacggcca ggagggcctt ttcccaggaa actacgtgga agatctga     2520

<210> SEQ ID NO 4
<211> LENGTH: 839
<212> TYPE: PRT
<213> ORGANISM: Homo sapiens

<400> SEQUENCE: 4

Met Gln Val Ile Gly Ile Pro Pro Ser Ile Gln Gln Leu Val Leu Gln
1               5                   10                  15

Leu Val Ala Gly Ile Leu His Leu Gly Asn Ile Ser Phe Cys Glu Asp
            20                  25                  30

Gly Asn Tyr Ala Arg Val Glu Ser Val Asp Leu Leu Ala Phe Pro Ala
        35                  40                  45

Tyr Leu Leu Gly Ile Asp Ser Gly Arg Leu Gln Glu Lys Leu Thr Ser
    50                  55                  60

Arg Lys Met Asp Ser Arg Trp Gly Gly Arg Ser Glu Ser Ile Asn Val
65                  70                  75                  80

Thr Leu Asn Val Glu Gln Ala Ala Tyr Thr Arg Asp Ala Leu Ala Lys
                85                  90                  95

Gly Leu Tyr Ala Arg Leu Phe Asp Phe Leu Val Glu Ala Ile Asn Arg
            100                 105                 110

Ala Met Gln Lys Pro Gln Glu Glu Tyr Ser Ile Gly Val Leu Asp Ile
        115                 120                 125

Tyr Gly Phe Glu Ile Phe Gln Lys Asn Gly Phe Glu Gln Phe Cys Ile
    130                 135                 140

Asn Phe Val Asn Glu Lys Leu Gln Gln Ile Phe Ile Glu Leu Thr Leu
145                 150                 155                 160

Lys Ala Glu Gln Glu Glu Tyr Val Gln Glu Gly Ile Arg Trp Thr Pro
                165                 170                 175

Ile Gln Tyr Phe Asn Asn Lys Val Val Cys Asp Leu Ile Glu Asn Lys
            180                 185                 190

Leu Ser Pro Pro Gly Ile Met Ser Val Leu Asp Asp Val Cys Ala Thr
        195                 200                 205

Met His Ala Thr Gly Gly Gly Ala Asp Gln Thr Leu Leu Gln Lys Leu
    210                 215                 220
```

-continued

```
Gln Ala Ala Val Gly Thr His Glu His Phe Asn Ser Trp Ser Ala Gly
225                 230                 235                 240

Phe Val Ile His His Tyr Ala Gly Lys Val Ser Tyr Asp Val Ser Gly
            245                 250                 255

Phe Cys Glu Arg Asn Arg Asp Val Leu Phe Ser Asp Leu Ile Glu Leu
        260                 265                 270

Met Gln Thr Ser Glu Gln Ala Phe Leu Arg Met Leu Phe Pro Glu Lys
    275                 280                 285

Leu Asp Gly Asp Lys Lys Gly Arg Pro Ser Thr Ala Gly Ser Lys Ile
290                 295                 300

Lys Lys Gln Ala Asn Asp Leu Val Ala Thr Leu Met Arg Cys Thr Pro
305                 310                 315                 320

His Tyr Ile Arg Cys Ile Lys Pro Asn Glu Thr Lys Arg Pro Arg Asp
                325                 330                 335

Trp Glu Glu Asn Arg Val Lys His Gln Val Glu Tyr Leu Gly Leu Lys
            340                 345                 350

Glu Asn Ile Arg Val Arg Arg Ala Gly Phe Ala Tyr Arg Arg Gln Phe
        355                 360                 365

Ala Lys Phe Leu Gln Arg Tyr Ala Ile Leu Thr Pro Glu Thr Trp Pro
    370                 375                 380

Arg Trp Arg Gly Asp Glu Arg Gln Gly Val Gln His Leu Leu Arg Ala
385                 390                 395                 400

Val Asn Met Glu Pro Asp Gln Tyr Gln Met Gly Ser Thr Lys Val Phe
                405                 410                 415

Val Lys Asn Pro Glu Ser Leu Phe Leu Leu Glu Glu Val Arg Glu Arg
            420                 425                 430

Lys Phe Asp Gly Phe Ala Arg Thr Ile Gln Lys Ala Trp Arg Arg His
        435                 440                 445

Val Ala Val Arg Lys Tyr Glu Glu Met Arg Glu Glu Ala Ser Asn Ile
    450                 455                 460

Leu Leu Asn Lys Lys Glu Arg Arg Asn Ser Ile Asn Arg Asn Phe
465                 470                 475                 480

Val Gly Asp Tyr Leu Gly Leu Glu Glu Arg Pro Glu Leu Arg Gln Phe
                485                 490                 495

Leu Gly Lys Arg Glu Arg Val Asp Phe Ala Asp Ser Val Thr Lys Tyr
            500                 505                 510

Asp Arg Arg Phe Lys Pro Ile Lys Arg Asp Leu Ile Leu Thr Pro Lys
        515                 520                 525

Cys Val Tyr Val Ile Gly Arg Glu Lys Val Lys Lys Gly Pro Glu Lys
    530                 535                 540

Gly Gln Val Cys Glu Val Leu Lys Lys Lys Val Asp Ile Gln Ala Leu
545                 550                 555                 560

Arg Gly Val Ser Leu Ser Thr Arg Gln Asp Asp Phe Phe Ile Leu Gln
                565                 570                 575

Glu Asp Ala Ala Asp Ser Phe Leu Glu Ser Val Phe Lys Thr Glu Phe
            580                 585                 590

Val Ser Leu Leu Cys Lys Arg Phe Glu Glu Ala Thr Arg Arg Pro Leu
        595                 600                 605

Pro Leu Thr Phe Ser Asp Thr Leu Gln Phe Arg Val Lys Lys Glu Gly
    610                 615                 620

Trp Gly Gly Gly Gly Thr Arg Ser Val Thr Phe Ser Arg Gly Phe Gly
625                 630                 635                 640

Asp Leu Ala Val Leu Lys Val Gly Gly Arg Thr Leu Thr Val Ser Val
```

```
                      645                 650                 655
Gly Asp Gly Leu Pro Lys Ser Ser Lys Pro Thr Arg Lys Gly Met Ala
            660                 665                 670

Lys Gly Lys Pro Arg Arg Ser Ser Gln Ala Pro Thr Arg Ala Ala Pro
        675                 680                 685

Ala Pro Pro Arg Gly Met Asp Arg Asn Gly Val Pro Pro Ser Ala Arg
    690                 695                 700

Gly Gly Pro Leu Pro Leu Glu Ile Met Ser Gly Gly Thr His Arg
705                 710                 715                 720

Pro Pro Arg Gly Pro Ser Thr Ser Leu Gly Ala Ser Arg Arg Pro
                725                 730                 735

Arg Ala Arg Pro Pro Ser Glu His Asn Thr Glu Phe Leu Asn Val Pro
            740                 745                 750

Asp Gln Gly Met Ala Gly Met Gln Arg Lys Arg Ser Val Gly Gln Arg
        755                 760                 765

Pro Val Pro Gly Val Gly Arg Pro Lys Pro Gln Pro Arg Thr His Gly
    770                 775                 780

Pro Arg Cys Arg Ala Leu Tyr Gln Tyr Val Gly Gln Asp Val Asp Glu
785                 790                 795                 800

Leu Ser Phe Asn Val Asn Glu Val Ile Glu Ile Leu Met Glu Asp Pro
                805                 810                 815

Ser Gly Trp Trp Lys Gly Arg Leu His Gly Gln Glu Gly Leu Phe Pro
            820                 825                 830

Gly Asn Tyr Val Glu Lys Ile
        835

<210> SEQ ID NO 5
<211> LENGTH: 1668
<212> TYPE: DNA
<213> ORGANISM: Homo sapiens

<400> SEQUENCE: 5
cagagccggc ttcgcctacc gccgccagtt cgccaaattc ctgcagaggt atgccattct      60
gacccccgag acgtggccgc ggtggcgtgg ggacgaacgc cagggcgtcc agcacctgct     120
tcgggcggtc aacatggagc ccgaccagta ccagatgggg agcaccaagg tctttgtcaa     180
gaacccagag tcgcttttcc tcctggagga ggtgcgagag cgaaagttcg atggctttgc     240
ccgaaccatc cagaaggcct ggcggcgcca cgtggctgtc cggaagtacg aggagatgcg     300
ggaggaagct tccaacatcc tgctgaacaa gaaggagcgg aggcgcaaca gcatcaatcg     360
gaacttcgtc gggactacc tggggctgga ggagcggccc gagctgcgtc agttcctggg     420
caagagggag cgggtggact cgccgattc ggtcaccaag tacgaccgcc gcttcaagcc     480
catcaagcgg gacttgatcc tgacgcccaa gtgtgtgtat gtgattgggc gagagaaagt     540
gaagaaggga cctgagaagg ccaggtgtg tgaagtcttg aagaagaaag tggacatcca     600
ggctctgcgg ggagtctccc tcagcacgcg acaggacgac ttcttcatcc tccaagagga     660
tgccgccgac agcttcctgg agagcgtctt caagaccgag tttgtcagcc ttctgtgcaa     720
gcgcttcgag gaggcgacgc ggaggcccct gcccctcacc ttcagcgaca cactacagtt     780
tcgggtgaag aaggagggct ggggcggtgg cggcaccccgc agcgtcacct tctcccccgg     840
cttcggcgac ttggcagtgc tcaaggttgg cggtcggacc ctcacggtca gcgtgggcga     900
tgggctgccc aagagctcca agcctacgcg aagggaatg gccaagggaa aacctcggag     960
gtcgtcccaa gcccctaccc gggcggcccc tgcgcccccc agaggcatgg atcgcaatgg    1020
```

-continued

```
ggtgccccc tctgccagag ggggcccct gccctggag atcatgtctg gagggggcac      1080
ccacaggcct ccccggggcc ctccgtccac atccctggga gccagcagac gaccccgggc   1140
acgtccgccc tcagagcaca acacagaatt cctcaacgtg cctgaccagg gcatggccgg   1200
catgcagagg aagcgcagcg tggggcaacg gccagtgcct ggtgtgggcc gacccaagcc   1260
ccagcctcgg acacatggtc ccaggtgccg ggccctatac cagtacgtgg gccaagatgt   1320
ggacgagctg agcttcaacg tgaacgaggt cattgagatc ctcatggaag atccctcggg   1380
ctggtggaag ggccggcttc acggccagga gggcctttc ccaggaaact acgtggagaa    1440
gatctgagct gggccctggg atactgcctt ctctttcgcc cgcctatctg cctgccggcc   1500
tggtggggag ccaggccctg ccaatgagag cctcgtttac ctgggctgca atagcctaaa   1560
agtccagtcc tttggcctcc agtcctgccc aggccctggg tcaccaggtc actgctgcag   1620 ccccgcccc tgggccctgg tcttcctcca acatcacacc tgctgccc                 1668
```

<210> SEQ ID NO 6
<211> LENGTH: 43
<212> TYPE: PRT
<213> ORGANISM: Artificial sequence
<220> FEATURE:
<223> OTHER INFORMATION: consensus sequence

<400> SEQUENCE: 6

```
Leu Pro Pro His Ile Phe Ala Ile Ala Asp Glu Ala Tyr Arg Ser Met
1               5                   10                  15

Leu Ser Asp Lys Glu Asn Gln Ser Ile Leu Ile Ser Gly Glu Ser Gly
            20                  25                  30

Ala Gly Lys Thr Glu Asn Thr Lys Lys Val Met
        35                  40
```

<210> SEQ ID NO 7
<211> LENGTH: 34
<212> TYPE: PRT
<213> ORGANISM: Homo sapiens

<400> SEQUENCE: 7

```
Asp Asn Met Tyr Arg Asn Met Leu Ile Asp Cys Glu Asn Gln Cys Val
1               5                   10                  15

Ile Ile Ser Gly Glu Ser Gly Ala Gly Lys Thr Val Ala Ala Lys Tyr
            20                  25                  30

Ile Met
```

<210> SEQ ID NO 8
<211> LENGTH: 43
<212> TYPE: PRT
<213> ORGANISM: Gallus gallus

<400> SEQUENCE: 8

```
Met Pro Pro His Ile Tyr Ala Ile Ala Asp Thr Ala Tyr Arg Ser Met
1               5                   10                  15

Leu Gln Asp Arg Glu Asp Gln Ser Ile Leu Cys Thr Gly Glu Ser Gly
            20                  25                  30

Ala Gly Lys Thr Glu Asn Thr Lys Lys Val Ile
        35                  40
```

<210> SEQ ID NO 9
<211> LENGTH: 43
<212> TYPE: PRT

-continued

<213> ORGANISM: Mollusca

<400> SEQUENCE: 9

Ile Pro Pro His Leu Phe Ser Val Ala Asp Asn Ala Tyr Gln Asn Met
1               5                   10                  15

Val Thr Asp Arg Glu Asn Gln Ser Cys Leu Ile Thr Gly Glu Ser Gly
            20                  25                  30

Ala Gly Lys Thr Glu Asn Thr Lys Lys Val Ile
        35                  40

<210> SEQ ID NO 10
<211> LENGTH: 43
<212> TYPE: PRT
<213> ORGANISM: Dictyostelium sp.

<400> SEQUENCE: 10

Val Ala Pro His Ile Phe Ala Ile Ser Asp Val Ala Tyr Arg Ser Met
1               5                   10                  15

Leu Asp Asp Arg Gln Asn Gln Ser Leu Leu Ile Thr Gly Glu Ser Gly
            20                  25                  30

Ala Gly Lys Thr Glu Asn Thr Lys Lys Val Ile
        35                  40

<210> SEQ ID NO 11
<211> LENGTH: 43
<212> TYPE: PRT
<213> ORGANISM: Caenorhabditis elegans

<400> SEQUENCE: 11

Met Pro Pro His Leu Phe Ala Val Ser Asp Glu Ala Tyr Arg Asn Met
1               5                   10                  15

Val Gln Asp Lys Glu Asn Gln Ser Met Leu Ile Thr Gly Glu Ser Gly
            20                  25                  30

Ala Gly Lys Thr Glu Asn Thr Lys Lys Val Ile
        35                  40

<210> SEQ ID NO 12
<211> LENGTH: 43
<212> TYPE: PRT
<213> ORGANISM: Drosophila sp.

<400> SEQUENCE: 12

Val Pro Pro His Val Phe Ala Ile Thr Asp Ser Ala Tyr Arg Asn Met
1               5                   10                  15

Leu Gly Asp Arg Glu Asp Gln Ser Ile Leu Cys Thr Gly Glu Ser Gly
            20                  25                  30

Ala Gly Lys Thr Glu Asn Thr Lys Lys Val Ile
        35                  40

<210> SEQ ID NO 13
<211> LENGTH: 43
<212> TYPE: PRT
<213> ORGANISM: Acanthamoeba sp.

<400> SEQUENCE: 13

Val Ala Pro His Ile Phe Ala Ile Ser Asp Ala Ala Tyr Arg Ala Met
1               5                   10                  15

Leu Asn Thr Arg Gln Asn Gln Ser Met Leu Ile Thr Gly Glu Ser Gly
            20                  25                  30

Ala Gly Lys Thr Glu Asn Thr Lys Lys Val Ile

```
                35                  40

<210> SEQ ID NO 14
<211> LENGTH: 43
<212> TYPE: PRT
<213> ORGANISM: Saccharomyces sp.

<400> SEQUENCE: 14

Leu Glu Pro His Leu Phe Ala Ile Ala Glu Glu Ala Tyr Arg Phe Met
1               5                   10                  15

Val His Glu Lys Ala Asn Gln Thr Val Val Ser Gly Glu Ser Gly
            20                  25                  30

Ala Gly Lys Thr Val Ser Ala Lys Tyr Ile Met
            35                  40

<210> SEQ ID NO 15
<211> LENGTH: 43
<212> TYPE: PRT
<213> ORGANISM: Bos taurus

<400> SEQUENCE: 15

Leu Lys Pro His Ile Tyr Ala Leu Ala Asn Met Ala Tyr Gln Ser Leu
1               5                   10                  15

Arg Asp Arg Asp Arg Asp Gln Cys Ile Leu Ile Thr Gly Glu Ser Gly
            20                  25                  30

Ala Gly Lys Thr Glu Ala Ser Lys Leu Val Met
            35                  40
```

MODULATORS OF B-LYMPHOCYTE ACTIVATION, MYOSIN-1F COMPOSITIONS AND METHODS OF USE

This application is a continuation of application Ser. No. 10/202,481, filed Jul. 23, 2002, now U.S. Pat. No. 6,890,725 B2, issued May 10, 2005; which is herein incorporated by reference.

FIELD OF THE INVENTION

The present invention relates to B-lymphocyte activation and platelet proliferation, and provides nucleic acids and proteins which are capable of modulating B-lymphocyte activation and platelet proliferation. The invention concerns disorders related to the dysfunction and dysregulation of B-lymphocyte activation, as well as disorders related to the dysfunction and dysregulation of platelet proliferation. These disorders include autoimmune diseases, acute and chronic inflammatory diseases, lymphomas, leukemias, and Wiskott-Aldrich syndrome. The invention further concerns the immune response of a host receiving a transplant. The invention further concerns disorders related to the dysfunction or dysregulation of myosin-1F.

BACKGROUND OF THE INVENTION

The immune response comprises a cellular response and a humoral response. The cellular response is mediated largely by T lymphocytes (alternatively and equivalently referred to herein as T-cells), while the humoral response is mediated by B lymphocytes (alternatively and equivalently referred to herein as B-cells).

B-cells produce and secrete antibodies in response to the presentation of antigen and MHC class II molecules on the surface of antigen presenting cells. Antigen presentation initiates B-cell activation with the engagement of the B-cell receptor (BCR) at the cell's surface. Following engagement, the BCR relays signals that are propagated through the cell's interior via signal transduction pathways. These signals lead to changes in B-cell gene expression and physiology, which underlie B-cell activation.

T-cells produce costimulatory molecules, including cytokines, that augment antibody production by B-cells during the humoral immune response. Cytokines also play a role in modulating the activity of T-cells themselves. Many T-cells act directly to engulf and destroy cells or agents that they recognize by virtue of the cell surface proteins they possess. The engagement of cell surface receptors on T-cells results in the propagation of intracellular signals that provoke changes in T-cell gene expression and physiology, which underlie the cellular immune response.

Antigen recognition alone is usually not sufficient to initiate a complete effector T or B-cell response. The generation of many B-cell responses to antigen is dependent upon the interaction of B-cells with CD4+ helper T-cells directed against the same antigen. These helper T-cells express CD40L (CD154) which binds to the cell surface receptor, CD40, on resting B-cells. This interaction provides a critical activation signal to B-cells. Mutations in the CD40L lead to the X-linked immunodeficiency disorder hyper-IgM syndrome, which is characterized by low levels of IgA and IgG, normal to elevated levels of IgM, absence of germinal center formation, and decreased immune response. In addition, transgenic mice lacking CD40 exhibit reduced graft rejection. (Zanelli et al., Nature Medicine, 6: 629-630, 2000; Schonbeck et al., Cell Mol Life Sci, 58:443, 2001).

Intercellular communication between different types of lymphocytes, as well as between lymphocytes and non-lymphocytes in the normally functioning immune system is well known. Much of this communication is mediated by cytokines and their cognate receptors. Cytokine-induced signals begin at the cell surface with a cytokine receptor and are transmitted intracellularly via signal transduction pathways. Many types of cells produce cytokines, and cytokines can induce a variety of responses in a variety of cell types, including lymphocytes. The response to a cytokine can be context-dependent as well as cell type specific.

Dysregulation of intercellular communication can perturb lymphocyte activity and the regulation of immune responses. Such dysregulation is believed to underlie certain autoimmune disease states, hyper-immune states, and immune-compromised states. Such dysfunction may be cell autonomous or non-cell autonomous with respect to lymphocytes.

The activation of specific signaling pathways in lymphocyte determines the quality, magnitude, and duration of immune responses. In response to transplantation, in acute and chronic inflammatory diseases, and in autoimmune responses, it is these pathways that are responsible for the induction, maintenance and exacerbation of undesirable lymphocyte responses. Identification of these signaling pathways is desirable in order to provide diagnostic and prognostic tools, as well as therapeutic targets for modulating lymphocyte function in a variety of disorders or abnormal physiological states. In addition, the ability to modulate these pathways and suppress normal immune responses is often desirable, for example in the treatment of hosts receiving a transplant.

The cytoskeleton is a target of some signal transduction pathways and regulation of the actin cytoskeleton is an important point of control in the immune response. The migration of lymphocytes in response to chemokines, the division of lymphocytes in response to cytokines and antigens, and the cellular shape changes associated with the development of plasma cells from pre B-cells, all involve changes in the actin cytoskeleton.

Myosin proteins are important regulators of actin organization, as well as motor proteins which interact with actin filaments to mediate important cellular functions, e.g., vesicle trafficking.

Unconventional myosins make up a diverse group of multidomain actin-based motor proteins which have been implicated in the regulation of focal actin polymerization and the trafficking of actin and phospholipids along actin fibers. The class I myosins contain an N-terminal myosin head domain, comprising an ATP-binding motif and an actin binding site. The myosin head domain has ATPase activity and exhibits ATP-dependent actin binding activity. Following the myosin head domain is an IQ domain(s), which mediates binding to the calcium-binding protein "calmodulin". Following the IQ domain are three domains, denoted TH1, TH2 and TH3 (Crozet-et al., Genomics; 40: 332-341, 1997).

The TH1 domain is rich in basic residues and mediates myosin-1 binding to phospholipds. The TH2 domain is enriched in glycine, proline and alanine, and may mediate ATP-independent binding to actin. The C-terminal TH3 domain is an SH3 domain, which mediates protein-protein interactions (Crozet et al., supra).

SUMMARY OF THE INVENTION

The present invention provides compositions and methods for modulating B-lymphocyte and platelet activation. Compositions and methods for the treatment of disorders related to the dysfunction and dysregulation of B-lymphocyte and platelet activation are also provided. Prophylactics and methods for the prevention of such disorders are also provided. Also provided are compositions and methods for the diagnostic and prognostic determination of such disorders. Further provided are assays for the identification of bioactive agents capable of modulating B-lymphocyte and platelet activation.

Accordingly, in one aspect, the invention provides myosin-1F nucleic acids which are capable of modulating B-lymphocyte and platelet activation. In another aspect, the invention provides myosin-1F proteins capable of modulating B-lymphocyte and platelet activation.

In a preferred embodiment, the invention provides myosin-1F nucleic acids which encode myosin-1F proteins.

In a preferred embodiment, the present invention provides myosin-1F proteins which can bind to one or more myosin-1F binding partners selected from the group consisting of BLNK, WASP, WASP-IP, Bee1p, Vrp1p, calmodulin, Arp2/3 complex, Acan125, ATP and actin.

In a preferred embodiment, a myosin-1F protein provided herein is capable of modulating B-cell receptor (BCR)-induced expression of CD69 in a B-lymphocyte. In an especially preferred embodiment, a myosin-1F protein provided herein is capable of modulating BCR-induced expression of CD69 in a B-lymphocyte, but does not modulate T-cell receptor (TCR)-induced CD69 expression in a T-lymphocyte.

In a preferred embodiment, a myosin-1F protein provided herein is capable of modulating BCR-induced activation of the immunoglobulin heavy chain gene (IgH) promoter in a B-lymphocyte. In an especially preferred embodiment, such a myosin-1F protein does not modulate TCR-induced T-cell activation.

In a preferred embodiment, a myosin-1F protein provided herein is capable of modulating BCR-induced immunoglobulin production in a B-lymphocyte. In an especially preferred embodiment, such a myosin-1F protein does not modulate TCR-induced T-cell activation.

In a preferred embodiment, a myosin-1F protein provided herein is capable of modulating intracellular calcium increase induced by antigen receptor activation in B-lymphocytes. In an especially preferred embodiment, such a myosin-1F protein does not modulate TCR-induced T-cell activation.

In a preferred embodiment, a myosin-1F protein provided herein is capable of modulating antigen receptor-induced calcineurin activity in B-lymphocytes. In an especially preferred embodiment, such a myosin-1F protein does not modulate TCR-induced T-cell activation.

In a preferred embodiment, a myosin-1F protein provided herein is capable of modulating the level of surface Ig, preferably surface IgM expression, on a resting B-lymphocyte.

In a preferred embodiment, a myosin-1F protein provided herein comprises the consensus phosphorylation site sequence GRSESINV occurring upstream of a conserved DALAK sequence, as in SEQ ID NO:2.

In a preferred embodiment, a myosin-1F protein provided herein is a substrate for phosphorylation by a protein kinase, preferably a PAK, as is known for myosin-1F homologs.

In a preferred embodiment, a myosin-1F nucleic acid provided herein is expressed in the following tissues and cells, in decreasing order of abundance of expression: lung, bone marrow, peripheral blood mononuclear cells, heart, spleen, placenta, HL-60 cells, liver, small intestine, BJAB cells, colon, trachea, uterus, adrenal gland, thymus, skeletal muscle, prostate, salivary gland, testis, thyroid, kidney, pancreas, whole brain, MCF-7 cells, Huh7 cells, cerebellum, phoenix A cells, and Jurkat cells.

The present invention also provides isolated polypeptides which specifically bind to a myosin-1F protein. In one embodiment, the polypeptide is an antibody. In a preferred embodiment, the polypeptide is a monoclonal antibody. In one embodiment, the monoclonal antibody is capable of reducing or eliminating the activity of myosin-1F. In another embodiment, the monoclonal antibody is capable of increasing or enhancing the activity of myosin-1F.

Also provided herein are methods of screening for a bioactive agent capable of binding to a myosin-1F protein. The methods comprise combining a myosin-1F protein and a candidate bioactive agent and determining the binding of candidate agent to myosin-1F protein. In one embodiment, the method involves identifying the candidate agent.

Also provided herein are methods of screening for a bioactive agent capable of interfering with the binding of a myosin-1F protein. The methods comprise combining a candidate bioactive agent, a myosin-1F protein, and a myosin-1F binding partner which will bind to myosin-1F in the absence of candidate agent, and determining the binding of myosin-1F to binding partner in the presence of candidate bioactive agent. In a preferred embodiment, the myosin-1F binding partner is selected from the group consisting of Wiskott-Aldrich syndrome protein-interacting protein (WASP), WASP-interacting protein (WASP-IP), BLNK, Bee1p, Vrp1p, calmodulin, Arp2/3 complex, Acan125, ATP and actin. In a preferred embodiment, the method involves determining the binding of myosin-1F to binding partner in the presence and absence of candidate bioactive agent. In one embodiment, myosin-1F and myosin-1F binding partner are combined first. In one embodiment, the method involves identifying the candidate agent.

Also provided herein are methods of screening for a bioactive agent capable of increasing the binding of a myosin-1F protein. The methods comprise combining a candidate bioactive agent, a myosin-1F protein, and a myosin-1F binding partner which will bind to myosin-1F in the absence of candidate agent, and determining the binding of myosin-1F to binding partner in the presence of candidate bioactive agent. In a preferred embodiment, the myosin-1F binding partner is selected from the group consisting of WASP, BLNK, WASP-IP, Bee1p, Vrp1p, calmodulin, Arp2/3 complex, Acan125, ATP and actin. In a preferred embodiment, the method involves determining the binding of myosin-1F to binding partner in the presence and absence of candidate bioactive agent. In one embodiment, myosin-1F and myosin-1F binding partner are combined first. In one embodiment, the method involves identifying the candidate agent.

Also provided herein are methods of screening for a bioactive agent capable of modulating the activity of a myosin-1F protein. In a preferred embodiment, the method comprises contacting a candidate bioactive agent to a cell comprising a recombinant myosin-1F nucleic acid and expressing a myosin-1F protein. In a preferred embodiment, the method comprises contacting a library of candidate bioactive agents to a plurality of cells comprising a recombinant myosin-1F nucleic acid and expressing a myosin-1F protein. In a preferred embodiment, the method comprises determining ATPase activity. In another preferred embodiment, the method comprises determining actin polymerization. In another preferred embodiment, the method comprises determining intracellular calcium concentration.

Also provided herein are methods of screening for a bioactive agent capable of modulating B-lymphocyte activation.

In a preferred embodiment, the methods comprise determining the ability of a candidate agent to bind to myosin-1F.

In a preferred embodiment, the methods comprise detecting binding of candidate agent to myosin-1F protein, contacting the candidate bioactive agent to a B-lymphocyte, and determining lymphocyte activation in the presence of said candidate agent. In a preferred embodiment, lymphocyte activation in the presence and absence of candidate agent is determined. In a preferred embodiment, an agent that normally induces lymphocyte activation is used. Lymphocyte activation is measured in the presence, and optionally, the absence of candidate agent following contact with the agent that normally induces lymphocyte activation. A preferred activation agent for use with B lymphocytes is anti-IgM antibody.

Bioactive agents that inhibit B-lymphocyte activation in these assays are useful as immunosuppressants.

In another preferred embodiment, the methods comprise determining the ability of a candidate agent to modulate the binding of myosin-1F to a myosin-1F binding partner.

In a preferred embodiment, the methods comprise detecting modulation of the binding of myosin-1F protein to a myosin-1F binding partner in the presence of candidate agent, contacting the candidate bioactive agent to a B-lymphocyte, and determining lymphocyte activation in the presence of said candidate agent. In a preferred embodiment, lymphocyte activation in the presence and absence of candidate agent is determined. In a preferred embodiment, an agent that normally induces lymphocyte activation is used. Lymphocyte activation is measured in the presence, and optionally, the absence of candidate agent following contact with the agent that normally induces lymphocyte activation. A preferred activation agent for use with B lymphocytes is anti-IgM antibody.

In an especially preferred embodiment, the myosin-1F binding partner used in these methods is selected from the group consisting of WASP, BLNK, WASP-IP, Bee1p, Vrp1p, calmodulin, Arp2/3 complex, Acan125, ATP and actin.

Bioactive agents that inhibit B-lymphocyte activation in these assays are useful as immunosuppressants.

In another preferred embodiment, the methods comprise determining the ability of a candidate bioactive agent to modulate the activity of a myosin-1F protein.

In a preferred embodiment, the methods comprise detecting modulation of ATPase activity, or modulation of actin binding activity, or modulation of actin polymerization inducing activity of myosin-1F in the presence of candidate bioactive agent, contacting the candidate bioactive agent to a B-lymphocyte, and determining lymphocyte activation in the presence of said candidate agent. In a preferred embodiment, lymphocyte activation in the presence and absence of candidate agent is determined. In a preferred embodiment, an agent that normally induces lymphocyte activation is used. Lymphocyte activation is measured in the presence, and optionally, the absence of candidate agent following contact with the agent that normally induces lymphocyte activation. A preferred activation agent for use with B lymphocytes is anti-IgM antibody.

Bioactive agents that inhibit lymphocyte activation in these assays are useful as immunosuppressants.

In a preferred embodiment, the methods comprise detecting binding of candidate agent to myosin-1F protein, contacting the candidate bioactive agent to a B-lymphocyte, and determining CD23 expression in the presence of said candidate agent. In a preferred embodiment, CD23 expression in the presence and absence of candidate agent is determined. In a preferred embodiment, an agent that normally induces CD23 expression is used. Lymphocyte activation is measured in the presence, and optionally, the absence of candidate agent following contact with the agent that normally induces CD23 expression. Preferred CD23 inducing agents are IL4, CD40L, and the combination of IL4 and CD40L.

Bioactive agents that inhibit CD23 induction in these assays are useful as immunosuppressants.

In a preferred embodiment, the methods comprise detecting modulation of the binding of myosin-1F protein to a myosin-1F binding partner in the presence of candidate agent, contacting the candidate bioactive agent to a B-lymphocyte, and determining CD23 expression in the presence of said candidate agent. In a preferred embodiment, CD23 expression in the presence and absence of candidate agent is determined. In a preferred embodiment, an agent that normally induces CD23 expression is used. Lymphocyte activation is measured in the presence, and optionally, the absence of candidate agent following contact with the agent that normally induces CD23 expression. Preferred CD23 inducing agents are IL-4, CD40L, and the combination of IL-4 and CD40L.

In an especially preferred embodiment, the myosin-1F binding partner used in these methods is selected from the group consisting of WASP, BLNK, WASP-IP, Bee1p, Vrp1p, calmodulin, Arp2/3 complex, Acan125, ATP and actin.

Bioactive agents that inhibit CD23 induction in these assays are useful as immunosuppressants.

In a preferred embodiment, the methods comprise detecting modulation of ATPase activity, or modulation of actin binding activity, or modulation of actin polymerization inducing activity of myosin-1F in the presence of candidate bioactive agent, contacting the candidate bioactive agent to a B-lymphocyte, and determining CD23 expression in the presence of said candidate agent. In a preferred embodiment, CD23 expression in the presence and absence of candidate agent is determined. In a preferred embodiment, an agent that normally induces CD23 expression is used. Lymphocyte activation is measured in the presence, and optionally, the absence of candidate agent following contact with the agent that normally induces CD23 expression. Preferred CD23 inducing agents are IL-4, CD40L, and the combination of IL-4 and CD40L.

Bioactive agents that inhibit CD23 induction in these assays are useful as immunosuppressants.

In a preferred embodiment, the methods comprise detecting binding of candidate agent to myosin-1F protein, contacting the candidate bioactive agent to a resting B-lymphocyte, and determining the level of surface Ig expression, preferably surface IgM expression, in the cell. Particularly preferred are Ramos cells and primary B-cells.

In a preferred embodiment, the methods comprise detecting modulation of the binding of myosin-1F protein to a myosin-1F binding partner in the presence of candidate agent, contacting the candidate bioactive agent to a resting B-lymphocyte, and determining the level of surface Ig expression, preferably surface IgM expression, in the cell. Particularly preferred are Ramos cells and primary B-cells.

In a preferred embodiment, the methods comprise detecting modulation of ATPase activity, or modulation of actin binding activity, or modulation of actin polymerization inducing activity of myosin-1F in the presence of candidate bioactive agent, contacting the candidate bioactive agent to a resting B-lymphocyte, and determining the level of surface Ig expression, preferably surface IgM expression, in the cell. Particularly preferred are Ramos cells and primary B-cells.

Agents that decrease surface Ig expression in resting B-cells are particularly preferred, and are useful as immunosuppressants.

In a preferred embodiment, candidate bioactive agents used in these assays are small molecule chemical compounds, from about 100 to about 1500, more preferably about 100 to about 1200, more preferably about 100 to about 1000, more preferably about 200 to about 500 daltons.

In a preferred embodiment, a library of candidate bioactive agents is contacted to myosin-1F protein.

In a preferred embodiment, determining lymphocyte activation in the methods herein comprises determining the level of expression of a surface marker which is associated with activation of the lymphocyte, in the presence of candidate agent. In a preferred embodiment, the surface marker is selected from the group consisting of CD23, CD69, CD80, and CD86. In an especially preferred embodiment, the surface marker is CD69 or CD23.

In another preferred embodiment, determining lymphocyte activation in the methods herein comprises determining the level of activity of a promoter in the presence of candidate agent, which activity correlates with lymphocyte activation in the absence of candidate agent. In a preferred embodiment the promoter is an NFAT-responsive promoter, such as the IL-2 promoter. In another preferred embodiment, the promoter is the immunoglobulin heavy chain gene promoter.

In another preferred embodiment, determining lymphocyte activation in the methods herein comprises determining the intracellular calcium concentration in the presence of candidate agent. In a preferred embodiment, the intracellular calcium concentration is determined in the presence and absence of candidate agent. Preferably, calcium concentration is determined using a calcium sensitive dye.

In a preferred embodiment, determining lymphocyte activation, including CD23 induction, is done using a FACS machine. In a preferred embodiment, lymphocytes are sorted by FACS. A FACS machine may be used to determine the level of expression of a surface marker or intracellular marker which normally correlates with lymphocyte activation, or the level of activity of a promoter which normally correlates with lymphocyte activation, or the intracellular calcium level, or other indicators of lymphocyte activation, including those discussed herein. Sorting of lymphocytes may be done on these bases.

Also provided herein are methods for inhibiting immunoglobulin production in a B-cell. In one embodiment, the methods comprise introducing into a B cell an immunosuppressant identified by the methods provided herein. In one embodiment, the methods comprise introducing into a B-cell a modulator of myosin-1F activity.

Also provided herein are methods for modulating lymphocyte activation in a patient having a lymphocyte activation disorder, comprising administering to a patient having a lymphocyte activation disorder a medicament comprising a modulator of myosin-1F protein activity.

Also provided herein are methods for inhibiting B cell activation in a patient having an autoimmune disease, comprising administering to a patient having an autoimmune disease a medicament comprising a modulator of myosin-1F activity.

Also provided herein are methods for inhibiting B cell activation in a patient having an autoimmune disease, comprising administering to a patient having an autoimmune disease a medicament comprising an immunosuppressant obtained by the screening methods provided herein.

Also provided herein are methods for inhibiting immunoglobulin production in a patient having an autoimmune disease, comprising administering to a patient having an autoimmune disease a medicament comprising a modulator of myosin-1F activity.

Also provided herein are methods for inhibiting immunoglobulin production in a patient having an autoimmune disease, comprising administering to a patient having an autoimmune disease a medicament comprising an immunosuppressant identified by the methods provided herein.

Also provided herein are methods for prolonging the survival of a graft in a mammalian host, comprising administering to a mammalian host receiving a graft a medicament comprising a modulator of myosin-1F activity.

Also provided herein are methods for prolonging the survival of a graft in a mammalian host, comprising administering to a mammalian host receiving a graft a medicament comprising an immunosuppressant identified by the methods provided herein.

In a preferred embodiment, provided herein are small molecule chemical compositions useful for the prevention and treatment of acute inflammatory disorders, chronic inflammatory disorders, autoimmune disorders, and transplant rejection.

BRIEF DESCRIPTION OF THE DRAWINGS

FIG. 1 shows nucleotide sequence of human myosin-1F, SEQ ID NO:1.

FIG. 2 shows amino acid sequence of human myosin-1F, SEQ ID NO:2.

FIG. 3 shows the results from experiments in which a myosin-1F fragment, consisting of an IQ domain and a portion of the tail domain ("Myosin 1F Hit") (amino acids 617-1098 of SEQ ID NO:2; nucleic acid SEQ ID NO:5), and a longer isoform of myosin-1F (myosin-1F long; SEQ ID NO:4) were expressed in the BJAB (B-cell) cell line and the Jurkat (T-cell) cell line, and BCR- or TCR-induced endogenous CD69 expression was assayed using a FACS machine. The results demonstrate that the short myosin-1F fragment inhibits BCR-induced lymphocyte activation but not TCR-induced lymphocyte activation, as measured by CD69 expression. The results also demonstrate that overexpression of the longer myosin-1F isoform does not affect BCR-induced or TCR-induced CD69 expression in BJAB and Jurkat cells.

FIG. 4 shows the results from experiments in which a myosin-1F fragment, consisting of an IQ domain and a portion of the tail domain ("Myosin 1F Hit") (amino acids 617-1098 of SEQ ID NO:2; nucleic acid SEQ ID NO:5), and a longer isoform of myosin-1F (myosin-1F long; SEQ ID NO:4) were expressed in the BJAB cell line and the Jurkat cell line, and BCR- or TCR-induced calcium increase was detected using a fluorescent calcium dye which was measured by a FACS machine. The results demonstrate that the short myosin-1F fragment inhibits intracellular calcium increase in BJAB cells but not Jurkat cells. The results further show that the longer myosin-1F isoform does not affect BCR-induced or TCR-induced calcium intracellular increase in BJAB and Jurkat cells.

FIG. 5 is a table of human autoimmune diseases.

FIG. 6 shows an alignment of ATP binding site sequences (SEQ. ID NOS. 6-15) between different myosin isoforms.

FIG. 7 shows an expression profile of myosin-1F mRNA in blood cell subsets in the resting and activated states.

DETAILED DESCRIPTION OF THE INVENTION

Figure 8:
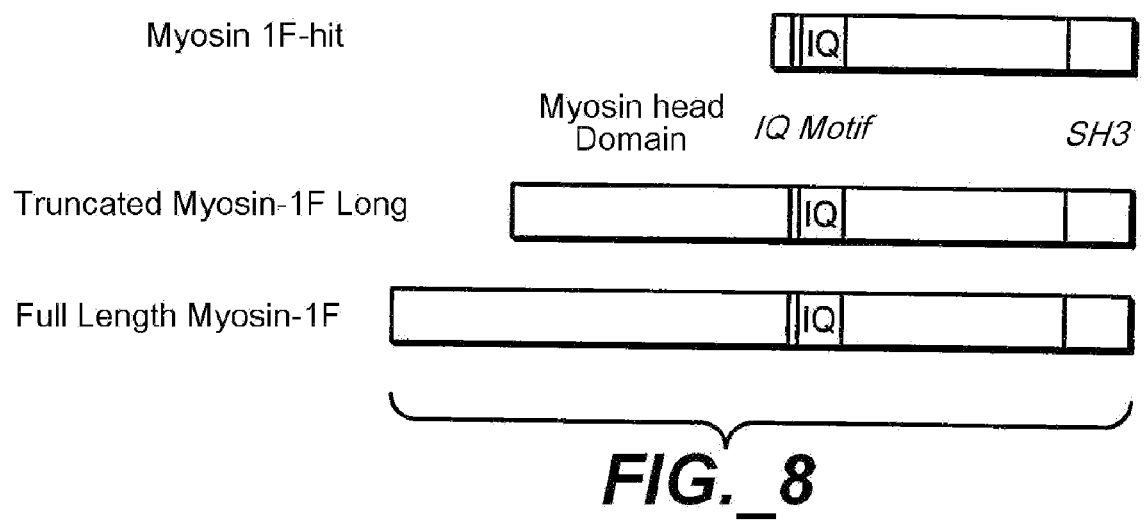
FIG. 8 shows the relationship between a truncated human myosin-1F protein (myosin-1F long above) (SEQ ID NO:4) and myosin-1F hit and full length myosin-1F.

The present invention provides compositions and methods for modulating B-lymphocyte activation and platelet activation. Compositions and methods for the treatment of disorders related to the dysfunction and dysregulation of B-lymphocyte activation and platelet activation are also provided. Prophylactics and methods for the prevention of such disorders are also provided. Also provided are compositions and methods for the diagnostic and prognostic determination of such disorders. Further provided are assays for the identification of bioactive agents capable of modulating B-lymphocyte activation and platelet activation.

In accordance with these objectives, in one aspect, the invention provides myosin-1F nucleic acids which are capable of modulating B-lymphocyte and platelet activation. Also in accordance with these objectives, in another aspect, the invention provides myosin-1F proteins capable of modulating B-lymphocyte and platelet activation.

A myosin-1F protein of the present invention may be identified in several ways. "Protein" in this sense includes proteins, polypeptides, and peptides. A myosin-1F protein may be identified by its ability to bind to myosin-1F binding partners as described herein. A myosin-1F protein may be identified by its ability to bind ATP, its ability to bind to actin in an ATP-dependent manner, its ability to bind to actin in an ATP-independent manner, its ability to bind to phospholipids, its ability to bind to calmodulin, its ATPase activity, and combinations of these properties. A myosin-1F protein may also be identified by amino acid sequence identity or similarity to SEQ ID NO:2, or by the sequence identity or similarity of its encoding nucleic acid to SEQ ID NO:1, more preferably the open reading frame (nucleotides 41-3337) of SEQ ID NO:1.

Myosin-1F nucleic acids and proteins may initially be identified by sequence identity or similarity to SEQ ID NOS:1 and 2, as further described below. In a preferred embodiment, myosin-1F nucleic acids and myosin-1F proteins have sequence identity or similarity to the sequences provided herein and one or more myosin-1F bioactivities described herein. Such sequence identity or similarity can be based upon the overall nucleic acid or amino acid sequence.

In a preferred embodiment, a myosin-1F protein provided herein comprises an amino acid sequence having at least about 85%, more preferably at least about 90%, more preferably at least about 95%, more preferably at least about 98% identity to the amino acid sequence set forth in SEQ ID NO:2. In a preferred embodiment, the myosin-1F protein comprises the amino acid sequence set forth in SEQ ID NO:2. Preferably, the myosin-1F protein also possesses one or more myosin-1F bioactivities described herein.

Myosin-1F protein having the amino acid sequence of SEQ ID NO:2 has been previously identified (Crozet et al., Genomics, 40:332-341, 1997). Myosin-1F is a member of the unconventional myosin I gene family, and comprises a number of conserved domains typically found in family members. Particularly, myosin-1F comprises an N-terminal myosin head domain having an ATP-binding site and actin binding site. The myosin head domain has ATPase activity and can bind to actin in an ATP-dependent manner. Following the myosin head domain, the "neck region" of the protein comprises a single IQ domain which binds to the calcium-binding protein "calmodulin". Following the single IQ domain are located a basic domain (TH1) which binds phospholipids, a glycine/proline/alanine-rich region (TH2) which binds actin in an ATP-independent manner, and a C-terminal SH3 domain (Crozet et al., supra). In addition, as with all vertebrate unconventional myosin I proteins, the myosin head domain lacks the conserved "TEDS rule" phosphorylation site found in protozoan myosins (Novak et al., Mol. Biol. of Cell, 9:75-88, 1998) and possesses a variation of this sequence.

Fragments are included in the definition of myosin-1F proteins herein. In a preferred embodiment, a myosin-1F protein provided herein comprises an amino acid sequence having at least about 85%, more preferably at least about 90%, more preferably at least about 95%, more preferably at least about 98% identity to a portion of the amino acid sequence set forth in SEQ ID NO:2. In a preferred embodiment, the myosin-1F protein comprises a portion of the amino acid sequence set forth in SEQ ID NO:2. Portion, or fragment, in this sense includes sequences from at least 2 amino acids up to the full length sequence in SEQ ID NO:2 minus one amino acid at either the N- or C-terminus.

In a preferred embodiment, such a myosin-1F protein comprises the amino acid sequence set forth in SEQ ID NO:4.

In an especially preferred embodiment, such a myosin-1F protein comprises a myosin head domain which can bind to ATP, possesses ATPase activity, and which can bind to actin, preferably in an ATP-dependent manner. In a preferred embodiment, such a myosin-1F protein comprises an amino acid sequence having at least about 85%, more preferably at least about 90%, more preferably at least about 95%, more preferably at least about 98% identity to the amino acid sequence set forth by residues 19-677, 1-677, 12-691, or 1-691 in SEQ ID NO:2. In an especially preferred embodiment, such a myosin-1F protein comprises the amino acid sequence set forth by residues 19-677, 1-677, 12-691, or 1-691 in SEQ ID NO:2.

In a preferred embodiment, such a myosin-1F protein comprises a partial myosin head domain. In a preferred embodiment, such a myosin-1F protein comprises an amino acid sequence having at least about 85%, more preferably at least about 90%, more preferably at least about 95%, more preferably at least about 98% identity to the amino acid sequence set forth by residues 260-677 or 260-691 in SEQ ID NO:2. In an especially preferred embodiment, such a myosin-1F protein comprises the amino acid sequence set forth by residues 260-677 or 260-691 in SEQ ID NO:2.

In another preferred embodiment, such a myosin-1F protein comprises a partial myosin head domain, an IQ domain, and a tail domain. In a preferred embodiment, such a myosin-1F protein comprises an amino acid sequence having at least about 85%, more preferably at least about 90%, more preferably at least about 95%, more preferably at least about 98% identity to the amino acid sequence set forth by residues 260-1098 in SEQ ID NO:2. In an especially preferred embodiment, such a myosin-1F protein comprises the amino acid sequence set forth by residues 260-1098 in SEQ ID NO:2. In another especially preferred embodiment, such a myosin-1F protein comprises the amino acid sequence set forth by SEQ ID NO:4.

In another especially preferred embodiment, such a myosin-1F protein comprises a tail domain, which comprises a TH1 domain, a TH2 domain, and an SH3 domain, each of which is further described herein. In a preferred embodiment, such a myosin-1F protein comprises an amino acid sequence having at least about 85%, more preferably at least about 90%, more preferably at least about 95%, more preferably at least about 98% identity to the amino acid sequence set forth by residues 718-1098 in SEQ ID NO:2. In an especially preferred embodiment, such a myosin-1F protein comprises the amino acid sequence set forth by residues 718-1098 in SEQ ID NO:2.

In another especially preferred embodiment, such a myosin-1F protein comprises an IQ domain, as further described herein. In a preferred embodiment, such a myosin-1F protein comprises an amino acid sequence having at least about 85%, more preferably at least about 90%, more preferably at least about 95%, more preferably at least about 98% identity to the amino acid sequence set forth by residues 695-717 in SEQ ID NO:2. In an especially preferred embodiment, such a myosin-1F protein comprises the amino acid sequence set forth by residues 695-717 in SEQ ID NO:2.

In another especially preferred embodiment, such a myosin-1F protein comprises an IQ domain and a tail domain. In a preferred embodiment, such a myosin-1F protein comprises an amino acid sequence having at least about 85%, more preferably at least about 90%, more preferably at least about 95%, more preferably at least about 98% identity to the amino acid sequence set forth by residues 695-1098 in SEQ ID NO:2. In an especially preferred embodiment, such a myosin-1F protein comprises the amino acid sequence set forth by residues 695-1098 in SEQ ID NO:2.

In another especially preferred embodiment, such a myosin-1F protein comprises an IQ domain and a tail domain. In a preferred embodiment, such a myosin-1F protein comprises an amino acid sequence having at least about 85%, more preferably at least about 90%, more preferably at least about 95%, more preferably at least about 98% identity to the amino acid sequence set forth by residues 617-1098 in SEQ ID NO:2. In an especially preferred embodiment, such a myosin-1F protein comprises the amino acid sequence set forth by residues 617-1098 in SEQ ID NO:2.

In another especially preferred embodiment, such a myosin-1F protein comprises a myosin head domain and an IQ domain. In a preferred embodiment, such a myosin-1F protein comprises an amino acid sequence having at least about 85%, more preferably at least about 90%, more preferably at least about 95%, more preferably at least about 98% identity to the amino acid sequence set forth by residues 1-717, 12-717 or 19-717 in SEQ ID NO:2. In an especially preferred embodiment, such a myosin-1F protein comprises the amino acid sequence set forth by residues 1-717, 12-717 or 19-717 in SEQ ID NO:2.

In another preferred embodiment, a myosin-1F protein provided herein consists essentially of an amino acid sequence having at least about 85%, more preferably at least about 90%, more preferably at least about 95%, more preferably at least about 98% identity to a portion of the amino acid sequence set forth in SEQ ID NO:2. In a preferred embodiment, the myosin-1F protein consists essentially of a portion of the amino acid sequence set forth in SEQ ID NO:2.

In another preferred embodiment, a myosin-1F protein provided herein consists essentially of the amino acid sequence set forth in SEQ ID NO:4.

In an especially preferred embodiment, such a myosin-1F protein consists essentially of a myosin head domain which can bind to ATP, possesses ATPase activity, and which can bind to actin, preferably in an ATP-dependent manner. In a preferred embodiment, such a myosin-1F protein consists essentially of an amino acid sequence having at least about 85%, more preferably at least about 90%, more preferably at least about 95%, more preferably at least about 98% identity to the amino acid sequence set forth by residues 19-677, 1-677, 12-691, or 1-691 in SEQ ID NO:2. In an especially preferred embodiment, such a myosin-1F protein consists essentially of the amino acid sequence set forth by residues 19-677, 1-677, 12-691, or 1-691 in SEQ ID NO:2.

In a preferred embodiment, such a myosin-1F protein consists essentially of a partial myosin head domain. In a preferred embodiment, such a myosin-1F protein consists essentially of an amino acid sequence having at least about 85%, more preferably at least about 90%, more preferably at least about 95%, more preferably at least about 98% identity to the amino acid sequence set forth by residues 260-677 or 260-691 in SEQ ID NO:2. In an especially preferred embodiment, such a myosin-1F protein consists essentially of the amino acid sequence set forth by residues 260-677 or 260-691 in SEQ ID NO:2.

In another preferred embodiment, such a myosin-1F protein consists essentially of a partial myosin head domain, an IQ domain, and a tail domain. In a preferred embodiment, such a myosin-1F protein consists essentially of an amino acid sequence having at least about 85%, more preferably at least about 90%, more preferably at least about 95%, more preferably at least about 98% identity to the amino acid sequence set forth by residues 260-1098 in SEQ ID NO:2. In an especially preferred embodiment, such a myosin-1F protein consists essentially of the amino acid sequence set forth by residues 260-1098 in SEQ ID NO:2. In another especially preferred embodiment, such a myosin-1F protein consists essentially of the amino acid sequence set forth by SEQ ID NO:4.

In another preferred embodiment, such a myosin-1F protein consists essentially of a tail domain, which comprises a TH1 domain, a TH2 domain, and an SH3 domain. In a preferred embodiment, such a myosin-1F protein consists essentially of an amino acid sequence having at least about 85%, more preferably at least about 90%, more preferably at least about 95%, more preferably at least about 98% identity to the amino acid sequence set forth by residues 718-1098 in SEQ ID NO:2. In an especially preferred embodiment, such a myosin-1F protein consists essentially of the amino acid sequence set forth by residues 718-1098 in SEQ ID NO:2.

In another preferred embodiment, such a myosin-1F protein consists essentially of an IQ domain and a tail domain which comprises a TH1 domain, a TH2 domain, and an SH3 domain. In a preferred embodiment, such a myosin-1F protein consists essentially of an amino acid sequence having at least about 85%, more preferably at least about 90%, more preferably at least about 95%, more preferably at least about 98% identity to the amino acid sequence set forth by residues 695-1098 in SEQ ID NO:2. In an especially preferred embodiment, such a myosin-1F protein consists essentially of the amino acid sequence set forth by residues 695-1098 in SEQ ID NO:2.

In another preferred embodiment, such a myosin-1F protein consists essentially of an IQ domain and a tail domain which comprises a TH1 domain, a TH2 domain, and an SH3 domain. In a preferred embodiment, such a myosin-1F protein consists essentially of an amino acid sequence having at least about 85%, more preferably at least about 90%, more preferably at least about 95%, more preferably at least about 98% identity to the amino acid sequence set forth by residues 617-1098 in SEQ ID NO:2. In an especially preferred embodiment, such a myosin-1F protein consists essentially of the amino acid sequence set forth by residues 617-1098 in SEQ ID NO:2.

In another preferred embodiment, such a myosin-1F protein consists essentially of a myosin head domain and an IQ domain. In a preferred embodiment, such a myosin-1F protein consists essentially of an amino acid sequence having at least about 85%, more preferably at least about 90%, more preferably at least about 95%, more preferably at least about 98% identity to the amino acid sequence set forth by residues 1-717, 12-717 or 19-717 in SEQ ID NO:2. In an especially preferred embodiment, such a myosin-1F protein consists essentially of the amino acid sequence set forth by residues 1-717, 12-717 or 19-717 in SEQ ID NO:2.

In another preferred embodiment, the such a myosin-1F protein consists essentially of a portion of a tail domain, particularly a TH2 domain and an SH3 domain.

In one aspect, the present invention provides myosin-1F nucleic acids, including myosin-1F nucleic acids encoding myosin-1F proteins.

In the case of a myosin-1F nucleic acid encoding a myosin-1F protein, the overall sequence identity of the nucleic acid sequence is commensurate with amino acid sequence identity but takes into account the degeneracy in the genetic code and codon bias of different organisms. Accordingly, the nucleic acid sequence identity may be either lower or higher than that of the protein sequence. A myosin-1F nucleic acid of the present invention comprises a nucleic acid sequence that preferably has greater than about 75% identity to the nucleic acid sequence set forth in SEQ ID NO:1, more preferably greater than about 80%, particularly greater than about 85% and most preferably greater than 90%. In some embodiments the sequence identity will be as high as about 93 to 95 or 98%.

In a preferred embodiment, a myosin-1F nucleic acid encodes a myosin-1F protein. As will be appreciated by those in the art, due to the degeneracy of the genetic code, an extremely large number of nucleic acids may be made, all of which encode the myosin-1F proteins of the present invention. Thus, having identified a particular amino acid sequence, those skilled in the art could make any number of different nucleic acids, by simply modifying the sequence of one or more codons in a way which does not change the amino acid sequence of the myosin-1F protein.

In a preferred embodiment, the myosin-1F nucleic acid comprises a nucleic acid sequence having at least about 85%, more preferably at least about 90%, more preferably at least about 95%, more preferably at least about 98% identity to the nucleic acid sequence set forth in SEQ ID NO:1, more preferably the open reading frame set forth in SEQ ID NO:1 from nucleotides 41-3337. In a preferred embodiment, the myosin-1F nucleic acid comprises the nucleic acid sequence set forth in SEQ ID NO:1, more preferably the open reading frame set forth in SEQ ID NO:1 from nucleotides 41-3337. In a preferred embodiment, the myosin-1F nucleic acid encodes a myosin-1F protein.

In a preferred embodiment, the myosin-1F nucleic acid comprises a nucleic acid sequence having at least about 85%, more preferably at least about 90%, more preferably at least about 95%, more preferably at least about 98% identity to the sequence set forth by nucleotides 1891-3558 in SEQ ID NO:1. In a preferred embodiment, the myosin-1F nucleic acid comprises the sequence set forth by nucleotides 1891-3558 in SEQ ID NO:1.

In a preferred embodiment, the myosin-1F nucleic acid comprises the sequence set forth by SEQ ID NO:3.

In a preferred embodiment, the myosin-1F nucleic acid comprises the sequence set forth by SEQ ID NO:5.

In a preferred embodiment, the present invention provides myosin-1F proteins encoded by myosin-1F nucleic acids provided herein.

In a preferred embodiment, the present invention provides myosin-1F nucleic acids encoding myosin-1F protein fragments described herein.

In one embodiment, the myosin-1F nucleic acid is determined through hybridization studies. Thus, for example, nucleic acids which hybridize under high stringency conditions to the nucleic acid sequences shown in SEQ ID NO:1 or their complements, or fragments thereof or their complements, are considered myosin-1F nucleic acids. High stringency conditions are known in the art; see for example Sambrook et al., *Molecular Cloning, A Laboratory Manual*. 3rd edition, 2001, Cold Spring Harbor Press, Cold Spring Harbor, N.Y.; and *Short Protocols in Molecular Biology*, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology-Hybridization with Nucleic Acid Probes, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH and nucleic acid concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide.

In another embodiment, less stringent hybridization conditions are used; for example, moderate or low stringency conditions may be used, as are known in the art; see Sambrook et al., *Molecular Cloning, A Laboratory Manual*, 3rd edition, 2001, Cold Spring Harbor Press, Cold Spring Harbor, N.Y.; and Tijssen, supra.

Also provided herein are myosin-1F antisense nucleic acids which will hybridize under high stringency conditions to a myosin-1F nucleic acid comprising the nucleic acid sequence set forth in SEQ ID NO:1. In a preferred embodiment, the myosin-1F antisense nucleic acid inhibits expression of myosin-1F protein. In a preferred embodiment, the myosin-1F antisense nucleic acid inhibits myosin-1F protein activity.

As is known in the art, a number of different programs can be used to identify whether a protein (or nucleic acid as discussed below) has sequence identity or similarity to a known sequence. Sequence identity and/or similarity is determined using standard techniques known in the art, including, but not limited to, the local sequence identity algorithm of Smith & Waterman, Adv. Appl. Math. 2:482 (1981), by the sequence identity alignment algorithm of Needleman & Wunsch, J. Mol. Biool. 48:443 (1970), by the search for similarity method of Pearson & Lipman, PNAS USA 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res. 12:387-395 (1984), preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127-149 (1988), Alan R. Liss, Inc.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, J. Mol. Evol. 35:351-360 (1987); the method is similar to that described by Higgins & Sharp CABIOS 5:151-153 (1989). Useful PILEUP parameters including a default gap weight of 3.00, a default gap length weight of 0.10, and weighted end gaps.

Another example of a useful algorithm is the BLAST algorithm, described in Altschul et al., J. Mol. Biol. 215, 403-410, (1990) and Karlin et al., PNAS USA 90:5873-5787 (1993). A particularly useful BLAST program is the WU-BLAST-2 program which was obtained from Altschul et al., *Methods in Enzymology*, 266: 460-480 (1996)]. WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al. Nucleic Acids Res. 25:3389-3402. Gapped BLAST uses BLOSUM-62 substitution scores; threshold T parameter set to 9; the two-hit method to trigger ungapped extensions; charges gap lengths of k a cost of 10+k; $X_u$ set to 16, and $X_g$ set to 40 for database search stage and to 67 for the output stage of the algorithms. Gapped alignments are triggered by a score corresponding to ~22 bits.

A percent amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, "percent (%) nucleic acid sequence identity" with respect to the coding sequence of the polypeptides identified herein is defined as the percentage of nucleotide residues in a candidate sequence that are identical with the nucleotide residues in the coding sequence of the myosin-1F protein. A preferred method utilizes the BLASTN module of WU-BLAST-2 set to the default parameters, with overlap span and overlap fraction set to 1 and 0.125, respectively.

The alignment may include the introduction of gaps in the sequences to be aligned. In addition, for sequences which contain either more or fewer amino acids than the protein encoded by SEQ ID NO:1, it is understood that in one embodiment, the percentage of sequence identity will be determined based on the number of identical amino acids in relation to the total number of amino acids. Thus, for example, sequence identity of sequences shorter than that shown in the Figure, as discussed below, will be determined using the number of amino acids in the shorter sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

As will be appreciated by those skilled in the art, the sequences of the present invention may contain sequencing errors. That is, there may be incorrect nucleosides, frameshifts, unknown nucleosides, or other types of sequencing errors in any of the sequences; however, the correct sequences will fall within the homology and stringency definitions herein.

In a preferred embodiment, a myosin-1F protein provided herein has one or more of the following characteristics: homology to SEQ ID NO:2; the ability to modulate B-lymphocyte activation without modulating T-lymphocyte activation; the ability to modulate antigen-receptor induced CD69 expression in B-lymphocytes; the ability to modulate immunoglobulin heavy chain gene (IgH) promoter activity in B-lymphocytes; the ability to modulate an increase in intracellular calcium concentration in B-lymphocytes in response to antigen receptor stimulation; the ability to modulate calcineurin activity in B-lymphocytes; and the ability to modulate NFAT activity in B-lymphocytes. Homology and identity to SEQ ID NO:2 can be determined as described above. In one embodiment, homology and identity are determined by performing a Blastp search in Genbank's non-redundant protein database using default parameters. In another embodiment, homology and identity are determined using the following database and parameters: Database:Non-redundant GenBank CDS translations+PDB+SwissProt+Spupdate+PIR; Lambda of 0.316, K of 0.133 and H of 0; Gapped Lambda of 0.27, K of 0.047, and H of 4.94e-324; Matrix is BLOSUM62; Gap Penalties: Existence: 11, Extension: 1.

In a preferred embodiment, the myosin-1F protein comprises the amino acid sequence set forth in SEQ ID NO:2. The characteristics described below also apply to other preferred myosin-1F proteins provided herein.

In some preferred embodiments, the myosin-1F protein binds to a myosin-1F binding partner, preferably selected from the group consisting of WASP, BLNK, WASP-IP, Bee1p, Vrp1p, calmodulin, Arp2/3 complex, Acan125, ATP and actin. In a preferred embodiment, the myosin-1F protein binds to a myosin-1F binding partner in B-lymphocytes. In another preferred embodiment, the myosin-1F protein binds to a myosin-1F binding partner in mast cells. In another preferred embodiment, the myosin-1F protein binds to a myosin-1F binding partner in platelets. In another preferred embodiment, the myosin-1F protein binds to a myosin-1F binding partner in monocytes. In another preferred embodiment, the myosin-F1 protein binds to a myosin-F1 binding partner in macrophages. In another preferred embodiment, the myosin-1F protein binds to a myosin-1F binding partner in peripheral blood lymphocytes. In an especially preferred embodiment, the myosin-1F protein binds to a myosin-1F binding partner in vitro.

WASP is the known Wiskoft-Aldrich syndrome protein associated with Wiskoft-Aldrich syndrome (Ramesh et al., Trends Cell Biol., 9:15-19, 1999; Machesky et al., Curr. Biol., 8:1347-1356, 1998). Wiskott-Aldrich syndrome is characterized by a decreased number of lymphocytes and platelets.

WASP-IP is the known WASP-interacting protein (Ramesh et al., supra; Ramesh et al., Proc. Nat'l Acad. Sci., 94:14671-14676, 1997). WASP and WASP-IP are known to associate with each other to regulate actin assembly (Vetterkind et al., J. Biol. Chem., 30:87-95, 2002).

Bee1p is a yeast homolog of WASP (Winter et al., Curr. Biol., 9:501-504, 1999) and Vrp1p is a yeast homolog of WASP-IP (Vaduva et al., J. Biol. Chem., 274:17103-17108, 1999). Beep1p and Vrp1p, as well as the Arp2/3 complex, are also involved in actin assembly in yeast (Winter et al., Proc. Natl. Acad. Sci., 96:7288-7293,1999).

Acan125 is a myosin I binding protein from Acanthamoeba (Xu et al., Proc. Natl. Acad. Sci., 94:3685-3690, 1997).

Calmodulin is a well known calcium-binding protein which binds to and regulates the activity of a large number of diverse proteins (Cheung, Science, 207:19-27, 1980; Hoeflich et al., Cell 108:739-742, 2002), including unconventional myosin I proteins.

ATP is adenosine triphosphate, the known nucleotide containing hydrolyzable phosphodiester bonds. As is known, the hydrolysis of ATP by ATPases is coupled to many enzymatic reactions (Stryer, Biochemistry, 4th Ed., W.H. Freeman and Co., New York, ISBN 0-7167-20094).

Actin is a well known polar protein which comprises the thin filaments of the cytoskeleton (Stryer, supra). As is well known in the art, actin polymers are directionally assembled from actin monomers in a head to tail fashion. The dynamic regulation of actin polymerization/depolymerization underlies cell motility and shape changes associated with, among other events, differentiation, division, and transformation.

BLNK is a well known B-cell linker protein which is involved in the mediation of B-cell activation. See Fu et al., Immunity, 9:93-103, 1998.

Myosin-1F proteins of the present invention may be shorter or longer than the amino acid sequence encoded by the nucleic acid sequence shown in SEQ ID NO:1. Thus, in a preferred embodiment, included within the definition of myosin-1F proteins are portions or fragments of the amino acid sequences encoded by the nucleic acid sequences provided herein. In one embodiment herein, fragments of myosin-1F proteins are considered myosin-1F proteins if a) they share at least one antigenic epitope; b) have at least the indicated sequence identity; c) and preferably have myosin-1F protein activity as further defined herein. In some cases, where the sequence is used diagnostically, that is, when the presence or absence of myosin-1F nucleic acid is determined, only the indicated sequence identity is required. The nucleic acids of the present invention may also be shorter or longer than the sequences in SEQ ID NO:1. The nucleic acid fragments include any portion of the nucleic acids provided herein which have a sequence not exactly previously identified; fragments having sequences with the indicated sequence identity to that portion not previously identified are provided in an embodiment herein.

In addition, as is more fully outlined below, myosin-1F proteins can be made that are longer than those depicted in SEQ ID NO:2; for example, by the addition of epitope or purification tags, the addition of other fusion sequences, or the elucidation of additional coding and non-coding sequences. As described below, the fusion of a myosin-1F peptide to a fluorescent protein, such as Blue Fluorescent Protein (BFP) or Green Fluorescent Protein (GFP), including those of Aquorea and Renilla species, is particularly preferred. In another preferred embodiment, the fluorescent protein is a GFP from Ptilosarcus. In another preferred embodiment, the fluorescent protein is a GFP homologue from Anthozoa species (Matz et al., Nat. Biotech., 17:969-973, 1999).

In a preferred embodiment, when a myosin-1F protein is to be used to generate antibodies, a myosin-1F protein must share at least one epitope or determinant with the full length protein. By "epitope" or "determinant" herein is meant a portion of a protein which will generate and/or bind an antibody. Thus, in most instances, antibodies made to a smaller myosin-1F protein will be able to bind to the full length protein. In a preferred embodiment, the epitope is unique; that is, antibodies generated to a unique epitope show little or no cross-reactivity. The term "antibody" includes antibody fragments, as are known in the art, including Fab Fab$_2$, single chain antibodies (Fv for example), chimeric antibodies, etc., either produced by the modification of whole antibodies or those synthesized de novo using recombinant DNA technologies.

In one embodiment, the antibodies to a myosin-1F protein are capable of reducing or eliminating the biological function of the myosin-1F proteins described herein, as is described below. That is, the addition of anti-myosin-1F antibodies (either polyclonal or preferably monoclonal) to myosin-1F proteins (or cells containing myosin-1F proteins) may reduce or eliminate their ability to modulate leukocyte and platelet activation. Generally, at least a 25% decrease in activity is preferred, with at least about 50% being particularly preferred and about a 95-100% decrease being especially preferred. These antibodies are sometimes referred to herein as function-blocking antibodies.

In another embodiment, anti-myosin-1F antibodies which increase the activity of myosin-1F or potentiate the activity of myosin-1F (function activating antibodies) are provided.

Function-activating and function-blocking antibodies may alter the ATPase activity of myosin-1F, or alter the affinity of myosin-1F for actin or for another myosin-1F binding partner, or may alter another myosin-1F bioactivity.

The anti-myosin-1F antibodies of the invention bind to myosin-1F proteins. In a preferred embodiment, the antibodies specifically bind to myosin-1F proteins. By "specifically bind" herein is meant that the antibodies bind to the protein with a binding constant in the range of at least $10^{-4}$-$10^{-6}$ M$^{-1}$, with a preferred range being $10^{-7}$-$10^{-9}$ M$^{-1}$. Antibodies are further described below.

The myosin-1F proteins and myosin-1F nucleic acids of the present invention are preferably recombinant. As used herein and further defined below, "nucleic acid" may refer to either DNA or RNA, or molecules which contain both deoxy- and ribonucleotides. The nucleic acids include genomic DNA, cDNA and oligonucleotides including sense and anti-sense nucleic acids. Such nucleic acids may also contain modifications in the ribose-phosphate backbone to increase stability and half life of such molecules in physiological environments.

The nucleic acid may be double stranded, single stranded, or contain portions of both double stranded and single stranded sequence. As will be appreciated by those in the art, the depiction of a single strand ("Watson") also defines the sequence of the other strand ("Crick"); thus the sequences depicted in the Figures also include the complement of the sequence.

By the term "recombinant nucleic acid" herein is meant nucleic acid, originally formed in vitro, in general, by the manipulation of nucleic acid by endonucleases, in a form not normally found in nature. Thus an isolated myosin-1F nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention. This includes nucleic acids which incorporate into the genome of a host cell.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of a myosin-1F protein from one organism in a different organism or host cell. Alternatively, the protein may be made at a significantly higher concentration than is normally seen, through the use of a inducible promoter or high expression promoter such that the protein is made at increased concentration levels. Alternatively, the protein may be in a form not normally found in nature, as in the addition of an epitope tag or amino acid substitutions, insertions and deletions, as discussed below.

In one embodiment, the present invention provides myosin-1F protein variants. These variants fall into one or more of three classes: substitutional, insertional or deletional variants. These variants ordinarily are prepared by site specific mutagenesis of nucleotides in the DNA encoding a myosin-1F protein, using cassette or PCR mutagenesis or other techniques well known in the art, to produce DNA encoding the variant, and thereafter expressing the DNA in recombinant cell culture as outlined above. However, variant myosin-1F protein fragments having up to about 100-150 residues may be prepared by in vitro synthesis using established techniques. Amino acid sequence variants are characterized by the predetermined nature of the variation, a feature that sets them apart from naturally occurring allelic or interspecies variation of the myosin-1F protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed myosin-1F protein variants screened for the optimal combination of desired activity. Techniques for making substitution mutations at predetermined sites in DNA having a known sequence are well known, for example, M13 primer mutagenesis and PCR mutagenesis. Screening of the mutants is done using assays of myosin-1F protein activities. Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the myosin-1F protein are desired, substitutions are generally made in accordance with the following chart:

CHART I

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophomyosin-1 Fity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophomyosin-1F residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and will elicit the same immune response as the naturally-occurring analogue, although variants also are selected to modify the characteristics of the myosin-1F proteins as needed. The variant may be designed such that the biological activity of the myosin-1F protein is altered. For example, catalytic residues or residues important for binding to myosin-1F binding partners may be altered.

In a preferred embodiment, myosin-1F variant proteins are provided which lack at least one myosin-1F protein activity. In a preferred embodiment, the myosin-1F variant protein lacks ATPase activity. In another preferred embodiment, the myosin-1F variant protein lacks the ability to bind to at least one myosin-1F binding partner selected from the group consisting of WASP, BLNK, WASP-IP, Bee1p, Vrp1p, calmodulin, Arp2/3 complex, Acan125, ATP and actin.

A preferred myosin-1F variant provided herein comprises an SH3 domain having a point mutation that diminishes or eliminates one or more myosin-1F activities, including binding to myosin-1F binding partners. Especially preferred is a myosin-1F variant having a mutation in the SH3 domain.

Another preferred myosin-1F variant provided herein comprises a myosin head domain having a point mutation that diminishes or eliminates one or more myosin-1F activities, including the ability to hydrolyze ATP and to bind actin in an ATP-dependent manner.

Another preferred myosin-1F variant provided herein comprises a myosin head domain having a point mutation that diminishes or eliminates the ability of myosin-1F to bind ATP.

A preferred myosin-1F variant provided herein has a point mutation at a residue which is normally phosphorylated in the context of myoain-1F by a protein kinase, preferably a PAK.

In a preferred embodiment, a myosin-1F variant protein provided herein exhibits dominant negative activity, i.e., inhibits the activity of wildtype myosin-1F protein. Such proteins are sometimes referred to herein as dominant negative myosin-1F proteins. Especially preferred are variant proteins which are capable of inhibiting the ability of wildtype myosin-1F to modulate lymphocyte activation.

In a preferred embodiment, the dominant negative myosin-1F protein modulates activation of the IgH promoter in lymphocytes.

In a preferred embodiment, the dominant negative myosin-1F protein modulates BCR-induced CD69 expression in B-lymphocytes.

In a preferred embodiment, the dominant negative myosin-1F protein modulates BCR-induced calcium flux in B-lymphocytes.

Without being bound by theory, in one aspect the dominant negative myosin-1F protein acts downstream of the BCR.

In one embodiment, myosin-1F variant proteins are provided which have increased activity. Increased activity may be due to a higher level of catalytic efficiency, a higher affinity for myosin-1F binding proteins, or a lower level of inhibition, or a combination thereof.

In a preferred embodiment, such myosin-1F variants modulate B-lymphocyte activation, for example in response to stimuli including but not limited to BCR engagement.

Covalent modifications of myosin-1F polypeptides are included within the scope of this invention. One type of covalent modification includes reacting targeted amino acid residues of a myosin-1F polypeptide with an organic derivatizing agent that is capable of reacting with selected side chains or the N-or C-terminal residues of a myosin-1F polypeptide. Derivatization with bifunctional agents is useful, for instance, for crosslinking myosin-1F to a water-insoluble support matrix or surface for use in the method for purifying anti-myosin-1F antibodies or screening assays, as is more fully described below. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the "-amino groups of lysine, arginine, and histidine side chains [T. E. Creighton, *Proteins: Structure and Molecular Properties*, W.H. Freeman & Co., San Francisco, pp. 79-86 (1983)], acetylation of the N-terminal amine, and amidation of any C-terminal carboxyl group.

Another type of covalent modification of the myosin-1F polypeptide included within the scope of this invention comprises altering the native glycosylation pattern of the polypeptide. "Altering the native glycosylation pattern" is intended for purposes herein to mean deleting one or more carbohydrate moieties found in native sequence myosin-1F polypeptide, and/or adding one or more glycosylation sites that are not present in the native sequence myosin-1F polypeptide.

Addition of glycosylation sites to myosin-1F polypeptides may be accomplished by altering the amino acid sequence thereof. The alteration may be made, for example, by the addition of, or substitution by, one or more serine or threonine residues to the native sequence myosin-1F polypeptide (for O-linked glycosylation sites). The myosin-1F amino acid sequence may optionally be altered through changes at the DNA level, particularly by mutating the DNA encoding the myosin-1F polypeptide at preselected bases such that codons are generated that will translate into the desired amino acids.

Another means of increasing the number of carbohydrate moieties on the myosin-1F polypeptide is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem.*, pp. 259-306 (1981).

Removal of carbohydrate moieties present on the myosin-1F polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo-and exo-glycosidases as described by Thotakura et al., *Meth. Enzymol.*, 138:350 (1987).

Another type of covalent modification of myosin-1F comprises linking the myosin-1F polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Myosin-1F polypeptides of the present invention may also be modified in a way to form chimeric molecules comprising a myosin-1F polypeptide fused to another, heterologous polypeptide or amino acid sequence. In one embodiment, such a chimeric molecule comprises a fusion of a myosin-1F polypeptide with a tag polypeptide which provides an epitope to which an anti-tag antibody can selectively bind. In a preferred embodiment, such a tag is the "flag tag" described below. The epitope tag is generally placed at the amino-or carboxyl-terminus of the myosin-1F polypeptide. The presence of such epitope-tagged forms of a myosin-1F polypeptide can be detected using an antibody against the tag polypeptide. Also, provision of the epitope tag enables the myosin-1F polypeptide to be readily purified by affinity purification using an anti-tag antibody or another type of affinity matrix that binds to the epitope tag. In an alternative embodiment, the chimeric molecule may comprise a fusion of a myosin-1F polypeptide with an immunoglobulin or a particular region of an immunoglobulin. For a bivalent form of the chimeric molecule, such a fusion could be to the Fc region of an IgG molecule as discussed further below.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159-2165 (1988)]; the c-myc tag and the 8F9, 3C7, 6E10, G4, B7 and 9E10 antibodies thereto [Evan et al., *Molecular and Cellular Biology*, 5:3610-3616 (1985)]; and the Herpes Simplex virus glycoprotein D (gD) tag and its antibody [Paborsky et al., *Protein Engineering*, 3(6):547-553 (1990)]. Other tag polypeptides include the Flag-peptide [Hopp et al., *BioTechnology*, 6:1204-1210 (1988)]; the KT3 epitope peptide [Martin et al., *Science*, 255:192-194 (1992)]; tubulin epitope peptide [Skinner et al., *J. Biol. Chem.*, 266:15163-15166 (1991)]; and the T7 gene 10 protein peptide tag [Lutz-Freyermuth et al., *Proc. Natl. Acad. Sci. USA*, 87:6393-6397 (1990)].

In an embodiment herein, myosin-1F protein family members and myosin-1F proteins from other organisms are cloned and expressed as outlined below. Thus, probe or degenerate polymerase chain reaction (PCR) primer sequences may be used to find other related myosin-1F proteins from humans or other organisms. As will be appreciated by those in the art, particularly useful probe and/or PCR primer sequences include the unique areas of the myosin-1F nucleic acid sequence. As is generally known in the art, preferred PCR primers are from about 15 to about 35 nucleotides in length, with from about 20 to about 30 being preferred, and may contain inosine as needed. The conditions for the PCR reaction are well known in the art. It is therefore also understood that provided along with the sequences in the sequences listed herein are portions of those sequences, wherein unique portions of 15 nucleotides or more are particularly preferred. The skilled artisan can routinely synthesize or cut a nucleotide sequence to the desired length.

Once isolated from its natural source, e.g., contained within a plasmid or other vector or excised therefrom as a linear nucleic acid segment, the recombinant myosin-1F nucleic acid can be further-used as a probe to identify and isolate other myosin-1F nucleic acids. It can also be used as a "precursor" nucleic acid to make modified or variant myosin-1F nucleic acids and proteins.

Of course, as will be recognized by the artisan, PCR may also be used to obtain large quantities of a desired myosin-1F nucleic acid from a source comprising such a myosin-1F nucleic acid.

Using the nucleic acids of the present invention which encode a myosin-1F protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the myosin-1F protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. As another example, operably linked refers to DNA sequences linked so as to be contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express the myosin-1F protein; for example, transcriptional and translational regulatory nucleic acid sequences from *Bacillus* are preferably used to express the myosin-1F protein in *Bacillus*. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are known in the art, and are useful in the present invention.

In addition, the expression vector may comprise additional elements. For example, the expression vector may have two replication systems, thus allowing it to be maintained in two organisms, for example in mammalian or insect cells for expression and in a prokaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

A preferred expression vector system is a retroviral vector system such as is generally described in PCT/US97/01019 and PCT/US97/01048, both of which are hereby expressly incorporated by reference.

Myosin-1F proteins of the present invention are produced by culturing a host cell transformed with an expression vector containing myosin-1F nucleic acid encoding a myosin-1F protein, under the appropriate conditions to induce or cause expression of the myosin-1F protein. The conditions appropriate for myosin-1F protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archebacteria, fungi, and insect and animal cells, including mammalian cells. Of particular interest are *Drosophila melangaster* cells, *Saccharomyces cerevisiae* and other yeasts, *E. coli, Bacillus subtilis*, SF9 cells, C129 cells, 293 cells, Neurospora, BHK, CHO, COS, and HeLa cells, fibroblasts, Schwanoma cell lines, immortalized mammalian myeloid and lymphoid cell lines.

In a preferred embodiment, the myosin-1F proteins are expressed in mammalian cells. Mammalian expression systems are also known in the art, and include retroviral systems. A mammalian promoter is any DNA sequence capable of binding mammalian RNA polymerase and initiating the downstream (3') transcription of a coding sequence for myosin-1F protein into mRNA. A promoter will have a transcription initiating region, which is usually placed proximal to the 5' end of the coding sequence, and usually a TATA box, typically located 25-30 base pairs upstream of the transcription initiation site. The TATA box is thought to direct RNA polymerase II to begin RNA synthesis at the correct site. However, TATA-free transcription initiation is also well known. A mammalian promoter will also contain an upstream promoter element (enhancer element), typically located within 100 to 200 base pairs upstream of the TATA box if present. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-transcriptional cleavage and polyadenylation. Examples of transcription terminator and polyadenlytion signals include those derived form SV40.

The methods of introducing exogenous nucleic acid into mammalian hosts, as well as other hosts, are well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

In a preferred embodiment, myosin-1F proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of myosin-1F protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli*, the ribosome binding site is called the Shine-Delgarno (SD) sequence and includes an initiation codon and a sequence 3-9 nucleotides in length located 3-11 nucleotides upstream of the initiation codon.

The expression vector may also include a signal peptide sequence that provides for secretion of the myosin-1F protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria).

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris*, and *Streptococcus lividans*, among others.

The bacterial expression vectors are transformed into bacterial host cells using techniques well known in the art, such as calcium chloride treatment, electroporation, and others.

In one embodiment, myosin-1F proteins are produced in insect cells. Expression vectors for the transformation of insect cells, and in particular, baculovirus-based expression vectors, are well known in the art.

In a preferred embodiment, myosin-1F protein is produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe*, and *Yarrowia lipolytica*. Preferred promoter sequences for expression in yeast include the inducible GAL1,10 promoter, the promoters from alcohol dehydrogenase, enolase, glucokinase, glucose-6-phosphate isomerase, glyceraldehyde-3-phosphate-dehydrogenase; hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the neomycin phosphotransferase gene, which confers resistance to G418; and the CUP1 gene, which allows yeast to grow in the presence of copper ions.

The myosin-1F protein may also be made as a fusion protein, using techniques well known in the art. Thus, for example, for the creation of monoclonal antibodies, if the desired epitope is small, the myosin-1F protein may be fused to a carrier protein to form an immunogen. Alternatively, the myosin-1F protein may be made as a fusion protein to increase expression, or for other reasons. For example, when the myosin-1F protein is a myosin-1F peptide, the nucleic acid encoding the peptide may be linked to other nucleic acid for expression purposes. Similarly, myosin-1F proteins of the invention can be linked to protein labels, such as green fluorescent protein (GFP), red fluorescent protein (RFP), blue fluorescent protein (BFP), yellow fluorescent protein (YFP), etc.

In one embodiment, the myosin-1F nucleic acids, proteins and antibodies of the invention are labeled. By "labeled" herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the compound at any position.

In a preferred embodiment, the myosin-1F protein is purified or isolated after expression. Myosin-1F proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the myosin-1F protein may be purified using a standard anti-myosin-1F antibody column. Ultrafiltration and diafiltration techniques, in conjunction with protein concentration, are also useful.

For general guidance in suitable purification techniques, see Scopes, R., *Protein Purification*, Springer-Verlag, NY (1982). The degree of purification necessary will vary depending on the use of the myosin-1F protein. In some instances no purification will be necessary.

Once expressed and purified if necessary, the myosin-1F proteins and nucleic acids are useful in a number of applications.

The nucleotide sequences (or their complement) encoding myosin-1F proteins have various applications in the art of molecular biology, including uses as hybridization probes, in chromosome and gene mapping and in the generation of anti-sense RNA and DNA. Myosin-1F protein nucleic acid will also be useful for the preparation of myosin-1F proteins by the recombinant techniques described herein.

The full-length native sequence myosin-1F protein gene, or portions thereof, may be used as hybridization probes for a cDNA library or genomic DNA library to isolate other genes (for instance, those encoding naturally-occurring variants of myosin-1F protein or myosin-1F protein from other species) which have a desired sequence identity to the myosin-1F protein coding sequence. Optionally, the length of the probes will be about 20 to about 50 bases. The hybridization probes may be derived from the nucleotide sequences herein or from genomic sequences including promoters, enhancer elements and introns of native sequences as provided herein. By way of example, a screening method will comprise isolating the coding region of the myosin-1F protein gene using the known DNA sequence to synthesize a selected probe of about 40 bases. Hybridization probes may be labeled by a variety of labels, including radionucleotides such as $^{32}P$ or 35S, or enzymatic labels such as alkaline phosphatase coupled to the probe via avidin/biotin coupling systems. Labeled probes having a sequence complementary to that of the myosin-1F protein gene of the present invention can be used to screen libraries of human cDNA, genomic DNA or mRNA to determine which members of such libraries the probe hybridizes.

Nucleotide sequences encoding a myosin-1F protein can also be used to construct hybridization probes for mapping the gene which encodes that myosin-1F protein and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

Nucleic acids which encode myosin-1F protein or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding a myosin-1F protein can be used to clone genomic DNA encoding a myosin-1F protein in accordance with established techniques and the genomic sequences used to generate transgenic animals that contain cells which express the desired myosin-1F DNA. In another embodiment, cDNA is used in the formation of a transgene. Methods for generating transgenic animals, particularly animals such as mice or rats, have become conventional in the art and are described, for example, in U.S. Pat. Nos. 4,736,866 and 4,870,009. Typically, particular cells would be targeted for the myosin-1F protein transgene expression with tissue-specific enhancers. Transgenic animals that include a copy of a transgene encoding a myosin-1F protein introduced into the germ line of the animal at an embryonic stage can be used to examine the effect of increased expression of the desired nucleic acid. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of the myosin-1F protein can be used to construct a myosin-1F protein "knock out" animal which has a defective or altered gene encoding a myosin-1F protein as a result of homologous recombination between the endogenous gene encoding a myosin-1F protein and altered genomic DNA encoding a myosin-1F protein introduced into an embryonic cell of the animal. For example, cDNA encoding a myosin-1F protein can be used to clone genomic DNA encoding a myosin-1F protein in accordance with established techniques. A portion of the genomic DNA encoding a myosin-1F protein can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell*, 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell*, 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the myosin-1F protein.

It is understood that the models described herein can be varied. For example, "knock-in" models can be formed, or the models can be cell-based rather than animal models.

Nucleic acid encoding the myosin-1F polypeptides, antagonists or agonists may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al, *Proc. Natl. Acad. Sci. USA* 83, 4143-4146 [1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology* 11, 205-210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al, *J. Biol. Chem.* 262, 4429-4432 (1987); and Wagner et al., *Proc. Natl. Acad. Sci. USA* 87, 3410-3414 (1990). For review of gene marking and gene therapy protocols see Anderson et al., *Science* 256, 808-813 (1992).

In a preferred embodiment, the myosin-1F proteins, nucleic acids, variants, modified proteins, cells and/or transgenics containing the said nucleic acids or proteins are used in screening assays. Identification of the myosin-1F proteins provided herein permits the design of drug screening assays for compounds that bind myosin-1F proteins, interfere with myosin-1F protein binding, modulate myosin-1F activity, and modulate B-lymphocyte activation.

The assays described herein preferably utilize human myosin-1F protein, although other mammalian proteins may also be used, including rodents (mice, rats, hamsters, guinea pigs, etc.), farm animals (cows, sheep, pigs, horses, etc.) and primates. These latter embodiments may be preferred in the development of animal models of human disease. In some embodiments, as outlined herein, truncated myosin-1F proteins may be used.

In a preferred embodiment, the methods comprise combining a myosin-1F protein and a candidate bioactive agent, and determining the binding of the candidate agent to the myosin-1F protein. In other embodiments, further discussed below, binding interference or bioactivity is determined.

The term "candidate bioactive agent" or "exogeneous compound" as used herein describes any molecule, e.g., protein, small organic molecule, carbohydrates (including polysaccharides), polynucleotide, lipids, etc. Generally a plurality of assay mixtures are run in parallel with different agent concentrations to obtain a differential response to the various concentrations. Typically, one of these concentrations serves as a negative control, i.e., at zero concentration or below the level of detection. In addition, positive controls, i.e. the use of agents known to bind myosin-1F protein, may be used.

Candidate agents encompass numerous chemical classes, though typically they are organic molecules, preferably small organic compounds having a molecular weight of more than 100 and less than about 2,500 daltons, more preferably between 100 and 2000, more preferably between about 100 and about 1250, more preferably between about 100 and about 1000, more preferably between about 100 and about 750, more preferably between about 200 and about 500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In a preferred embodiment, a library of different candidate bioactive agents are used. Preferably, the library should provide a sufficiently structurally diverse population of randomized agents to effect a probabilistically sufficient range of diversity to allow binding to a particular target. Accordingly, an interaction library should be large enough so that at least one of its members will have a structure that gives it affinity for the target. Although it is difficult to gauge the required absolute size of an interaction library, nature provides a hint with the immune response: a diversity of $10^7$-$10^8$ different antibodies provides at least one combination with sufficient affinity to interact with most potential antigens faced by an organism. Published in vitro selection techniques have also shown that a library size of $10^7$ to $10^8$ is sufficient to find structures with affinity for the target. A library of all combinations of a peptide 7 to 20 amino acids in length, such as generally proposed herein, has the potential to code for $20^7$ ($10^9$) to $20^{20}$. Thus, with libraries of $10^7$ to $10^8$ different molecules the present methods allow a "working" subset of a theoretically complete interaction library for 7 amino acids, and a subset of shapes for the $20^{20}$ library. Thus, in a preferred embodiment, at least $10^6$, preferably at least $10^7$, more preferably at least $10^8$ and most preferably at least $10^9$ different sequences are simultaneously analyzed in the subject methods. Preferred methods maximize library size and diversity.

In a preferred embodiment, the candidate bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and noreleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations. Chemical blocking groups or other chemical substituents may also be added.

In a preferred embodiment, the candidate bioactive agents are naturally occurring proteins or fragments of naturally occurring proteins. Thus, for example, cellular extracts containing proteins, or random or directed digests of proteinaceous cellular extracts, may be used. In this way libraries of procaryotic and eukaryotic proteins may be made for screening in the systems described herein. Particularly preferred in this embodiment are libraries of bacterial, fungal, viral, and mammalian proteins, with the latter being preferred, and human proteins being especially preferred.

In a preferred embodiment, the candidate bioactive agents are peptides of from about 5 to about 30 amino acids, with from about 5 to about 20 amino acids being preferred, and from about 7 to about 15 being particularly preferred, and 12 and 18 amino acids being most preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the candidate bioactive agents are nucleic acids. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage, et al., *Tetrahedron*, 49(10):1925 (1993) and references therein; Letsinger, *J. Org. Chem.*, 35:3800 (1970); Sprinzl, et al., *Eur. J. Biochem.*, 81:579 (1977); Letsinger, et al., *Nucl. Acids Res.*, 14:3487 (1986); Sawai, et al., *Chem. Lett.*, 805 (1984), Letsinger, et al., *J. Am. Chem. Soc.*, 110:4470 (1988); and Pauwels, et al., *Chemica Scripta*, 26:141 (1986)), phosphorothioate (Mag, et al., *Nucleic Acids Res.*, 19:1437 (1991); and U.S. Pat. No. 5,644,048), phosphorodithioate (Briu, et al., *J. Am. Chem. Soc.*, 111:2321 (1989)), O-methylphophoroamidite linkages (see Extern, Oligonucleotides and Analogues: A Practical Approach, Oxford University Press), and peptide nucleic acid backbones and linkages (see Egholm, *J. Am. Chem. Soc.*, 114: 1895 (1992); Meier, et al., *Chem. Int. Ed. Engl.*, 31:1008 (1992); Nielsen, *Nature*, 365:566 (1993); Carlsson, et al., *Nature*, 380:207 (1996), all of which are incorporated by reference)). Other analog nucleic acids include those with positive backbones (Denpcy, et al., *Proc. Natl. Acad. Sci. USA*, 92:6097 (1995)); non-ionic backbones (U.S. Pat. Nos.

5,386,023; 5,637,684; 5,602,240; 5,216,141; and 4,469,863; Kiedrowshi, et al., *Angew. Chem. Intl. Ed. English,* 30:423 (1991); Letsinger, et al., *J. Am. Chem. Soc.,* 110:4470 (1988); Letsinger, et al., Nucleoside & Nucleotide, 13:1597 (1994); Chapters 2 and 3, ASC Symposium Series 580, "Carbohydrate Modifications in Antisense Research", Ed. Y. S. Sanghui and P. Dan Cook; Mesmaeker, et al., *Bioorganic & Medicinal Chem. Left.,* 4:395 (1994); Jeffs, et al., *J. Biomolecular NMR,* 34:17 (1994); Tetrahedron Left., 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars, as well as "locked nucleic acids", are also included within the definition of nucleic acids (see Jenkins, et al., *Chem. Soc. Rev.,* (1995) pp. 169-176). Several nucleic acid analogs are described in Rawls, C & E News, Jun. 2, 1997, page 35. All of these references are hereby expressly incorporated by reference. These modifications of the ribose-phosphate backbone may be done to facilitate the addition of additional moieties such as labels, or to increase the stability and half-life of such molecules in physiological environments. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

For an example of how nucleic acids may be used as candidate agents to screen for a change in phenotype, see Holland et al., J. Exp. Med., 194:1263-1276, 2001. See also Hitoshi et al., Immunity, 8:461-471, 1998. Both of which are expressly incorporated herein by reference.

As described above generally for proteins, nucleic acid candidate bioactive agents may be naturally occurring nucleic acids, random nucleic acids, or "biased" random nucleic acids. For example, digests of procaryotic or eukaryotic genomes may be used as is outlined above for proteins.

In a preferred embodiment, the candidate bioactive agents are organic chemical moieties or small molecule chemical compositions, a wide variety of which are available in the literature.

In a preferred embodiment, the candidate bioactive agents are linked to a fusion partner. By "fusion partner" or "functional group" herein is meant a sequence that is associated with the candidate bioactive agent, that confers upon all members of the library in that class a common function or ability. Fusion partners can be heterologous (i.e. not native to the host cell), or synthetic (not native to any cell). Suitable fusion partners include, but are not limited to: a) presentation structures, which provide the candidate bioactive agents in a conformationally restricted or stable form; b) targeting sequences, which allow the localization of the candidate bioactive agent into a subcellular or extracellular compartment; c) rescue sequences which allow the purification or isolation of either the candidate bioactive agents or the nucleic acids encoding them; d) stability sequences, which confer stability or protection from degradation to the candidate bioactive agent or the nucleic acid encoding it, for example resistance to proteolytic degradation; e) dimerization sequences, to allow for peptide dimerization; or f) any combination of a), b), c), d), and e), as well as linker sequences as needed.

Generally, in a preferred embodiment of the methods herein, for example for binding assays, the myosin-1F protein or the candidate agent is non-diffusibly bound to an insoluble support having isolated sample receiving areas (e.g. a microtiter plate, an array, etc.). The insoluble supports may be made of any composition to which the compositions can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, teflon™, etc. Microtiter plates and arrays are especially convenient because a large number of assays can be carried out simultaneously, using small amounts of reagents and samples. In some cases magnetic beads and the like are included. The particular manner of binding of the composition is not crucial so long as it is compatible with the reagents and overall methods of the invention, maintains the activity of the composition and is nondiffusable. Preferred methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. Following binding of the protein or agent, excess unbound material is removed by washing. The sample receiving areas may then be blocked through incubation with bovine serum albumin (BSA), casein or other innocuous protein or other moiety. Also included in this invention are screening assays wherein solid supports are not used; examples of such are described below.

In a preferred embodiment, the myosin-1F protein is bound to the support, and a candidate bioactive agent is added to the assay. Alternatively, the candidate agent is bound to the support and the myosin-1F protein is added. Novel binding agents include specific antibodies, non-natural binding agents identified in screens of chemical libraries, peptide analogs, etc. Of particular interest are screening assays for agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the candidate bioactive agent to the myosin-1F protein may be done in a number of ways. In a preferred embodiment, the candidate bioactive agent is labelled, and binding determined directly. For example, this may be done by attaching all or a portion of the myosin-1F protein to a solid support, adding a labelled candidate agent (for example a fluorescently labeled agent), washing off excess reagent, and determining whether the label is present on the solid support. Various blocking and washing steps may be utilized as is known in the art.

By "labeled" herein is meant that the compound is either directly or indirectly labeled with a label which provides a detectable signal, e.g. radioisotope, fluorescers, enzyme, antibodies, particles such as magnetic particles, chemiluminescers, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined herein. The label can directly or indirectly provide a detectable signal.

In some embodiments, only one of the components is labeled. For example, the proteins (or proteinaceous candidate agents) may be labeled at tyrosine positions using $^{125}$I, or with fluorophores. Alternatively, more than one component may be labeled with different labels; using $^{125}$I for the proteins, for example, and a fluorophor for the candidate agents.

In a preferred embodiment, the binding of the candidate bioactive agent is determined through the use of competitive binding assays. In this embodiment, the competitor is a binding moiety known to bind to the target molecule (i.e. myosin-1F protein), such as an antibody. In a preferred embodiment, the competitor is selected from the group consisting of WASP, BLNK, WASP-IP, Bee1p, Vrp1p, calmodulin, Arp2/3 complex, Acan125, ATP and actin. Under certain circumstances, there may be competitive binding as between the bioactive agent and the binding moiety, with the binding moiety displacing the bioactive agent. This assay can be used to determine candidate agents which interfere with binding of myosin-1F to its binding partner. "Binding interference", or grammatical equivalents, as used herein means that native binding of the myosin-1F protein differs in the presence of the candidate agent. The binding can be eliminated or can be with a reduced affinity. In one embodiment, interference is caused by, for example, a conformational change, rather than direct competition for the native binding site.

In one embodiment, the candidate bioactive agent is labeled. Either the candidate bioactive agent, or the competitor, or both, is added first to the protein for a time sufficient to allow binding, if present. Incubations may be performed at any temperature which facilitates optimal activity, typically between 4° C. and 40° C. Incubation periods are selected for optimum activity, but may also be optimized to facilitate rapid high through put screening. Typically between 0.1 and 1 hour will be sufficient. Excess reagent is generally removed or washed away. The second component is then added, and the presence or absence of the labeled component is followed, to indicate binding. In a preferred embodiment, the competitor is added first, followed by the candidate bioactive agent.

Displacement of the competitor is an indication that the candidate bioactive agent is binding to the myosin-1F protein and thus is capable of binding to, and potentially modulating, the activity of the myosin-1F protein. In this embodiment, either component can be labeled. Thus, for example, if the competitor is labeled, the presence of label in the wash solution indicates displacement by the agent. Alternatively, if the candidate bioactive agent is labeled, the presence of the label on the support indicates displacement.

In an alternative embodiment, the candidate bioactive agent is added first, with incubation and washing, followed by the competitor. The absence of binding by the competitor may indicate that the bioactive agent is bound to the myosin-1F protein with a higher affinity. Thus, if the candidate bioactive agent is labeled, the presence of the label on the support, coupled with a lack of competitor binding, may indicate that the candidate agent is capable of binding to the myosin-1F protein.

In a preferred embodiment, the methods comprise differential screening to identity bioactive agents that are capable of modulating the activity of the myosin-1F proteins. In one embodiment, the methods comprise combining a myosin-1F protein and a competitor in a first sample. A second sample comprises a candidate bioactive agent, a myosin-1F protein and a competitor. The binding of the competitor is determined for both samples, and a change, or difference in binding between the two samples indicates the presence of an agent capable of binding to the myosin-1F protein and modulating its activity. That is, if the binding of the competitor is different in the second sample relative to the first sample, the agent is capable of binding to the myosin-1F protein and modulating its activity.

Alternatively, a preferred embodiment utilizes differential screening to identify drug candidates that bind to the native myosin-1F protein, but cannot bind to modified myosin-1F proteins. The structure of the myosin-1F protein may be modeled, and used in rational drug design to synthesize agents that interact with a catalytic, binding, or regulatory domain.

Positive controls and negative controls may be used in the assays. Preferably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

Screening for agents that modulate the activity of a myosin-1F protein may also be done. In a preferred embodiment, methods for screening for a bioactive agent capable of modulating the activity of a myosin-1F protein comprise the steps of adding a candidate bioactive agent to a sample of a myosin-1F protein and determining an alteration in the biological activity of the myosin-1F protein. "Modulating the activity of a myosin-1F protein" includes an increase in activity, a decrease in activity, or a change in the type or kind of activity present. Thus, in this embodiment, the candidate agent may bind to a myosin-1F protein (although this may not be necessary), and should alter its biological or biochemical activity as defined herein. The methods include in vivo screening of cells for alterations in the presence, cellular distribution, subcellular distribution, activity or amount of myosin-1F protein.

By "myosin-1F protein activity" or grammatical equivalents herein is meant at least one of the myosin-1F protein's biological activities, including, but not limited to, modulation of B-lymphocyte activation; modulation of lymphocyte activation by antigen; modulation of B-cell differentiation; modulation of B-lymphocyte proliferation; modulation of IgM and IgG induction in B-lymphocytes; modulation of calcium flux induced by BCR stimulation; modulation of immunoglobulin heavy chain gene promoter activity in lymphocytes; modulation of NFAT activity in B-lymphocytes; modulation of immunoglobulin secretion by B-lymphocytes; modulation of cytokine production in B-lymphocytes; modulation of surface protein expression including CD69, CD23, CD80 and CD86 in B-lymphocytes; modulation of intracellular calcium concentration in B-lymphocytes; modulation of intracellular calcium increase in response to antigen-receptor activation in B-lymphocytes; modulation of calcineurin activity in B-lymphocytes; modulation of calcineurin activity induction by antigen receptor activation in B-lymphocytes; binding to calmodulin, actin, BLNK, ATP, Arp2/3, Bee1p, WASP, WASP-I P, or Vrp1p; ATPase activity; ATP-dependent actin binding; ATP-independent actin binding; actin polymerization-inducing activity; and ability to modulate B-lymphocyte activation without modulating T-lymphocyte activation.

In a preferred embodiment, the activity of the myosin-1F protein is decreased; in another preferred embodiment, the activity of the myosin-1F protein is increased. Thus, bioactive agents that are antagonists are preferred in some embodiments, and bioactive agents that are agonists are preferred in other embodiments.

In an especially preferred embodiment, methods of screening for candidate bioactive agents capable of modulating the ATPase activity of a myosin-1F protein are provided. In a preferred embodiment, the methods involve incubating myosin-1F or a sample comprising myosin-1F with $\gamma^{32}$P-labelled ATP and separating $^{32}$P labelled inorganic phosphate from unreacted $\gamma^{32}$P-labelled ATP by thin layer chromatography to determine the extent of ATP hydrolysis. Such methods are well known, for example, see Burlacu et al., Biophys. J., 72:263-271, 1997. See also Bikle et al., J. Biol. Chem., 271:9075-9083, 1996.

In another especially preferred embodiment, methods of screening for candidate bioactive agents capable of modulating the calmodulin-binding activity of a myosin-1F protein are provided. Assays for determining calmodulin binding are known in the art, for example, see Coluccio, J. Cell Sci., 107:2279-2284, 1994.

In another especially preferred embodiment, methods of screening for candidate bioactive agents capable of modulating the actin-binding activity of a myosin-1F protein are provided. Methods for determining actin-myosin interactions are well known in the art, for example, see Bikle et al., J. Biol. Chem., 271:9075-9083, 1996.

In another preferred embodiment, methods of screening for candidate bioactive agents capable of modulating the actin polymerization-inducing activity of a myosin-1F protein are provided. In a preferred embodiment, the methods involve performing actin assembly assays in the presence of myosin-1F protein. Such assays employing yeast cells are known, for example, see Lechler et al., J. Cell Biol., 148: 363-373, 2000. Visual in vitro assays for actin polymerization are also known, for example, see Geli et al., EMBO J., 19:4281-4291, 2000.

Methods for screening for agents that modulate B-cell activation are also provided herein.

In a preferred embodiment, the methods comprise determining the ability of a candidate agent to bind to myosin-1F.

In a preferred embodiment, the methods comprise detecting binding of candidate agent to myosin-1F protein, contacting the candidate bioactive agent to a B-lymphocyte, and determining lymphocyte activation in the presence of said candidate agent. In a preferred embodiment, lymphocyte activation in the presence and absence of candidate agent is determined. In a preferred embodiment, an agent that normally induces lymphocyte activation is used. Lymphocyte activation is measured in the presence, and optionally, the absence of candidate agent following contact with the agent that normally induces lymphocyte activation. A preferred activation agent for use with B lymphocytes is anti-IgM antibody.

It will be understood that while agents that normally induce lymphocyte activation (i.e., activation agents) are used, the screening method is designed to identify agents that are capable of inhibiting lymphocyte activation. Accordingly, the presence of a bioactive agent that is capable of inhibiting lymphocyte activation may preclude activation of the lymphocyte by the activation agent. Such agents are nevertheless referred to herein as activation agents, and the step of contacting the cells with such an activation agent is frequently referred to herein as "inducing lymphocyte activation", even though a candidate bioactive agent may inhibit such activation by the agent. This nomenclature applies to the methods that follow as well.

In a preferred embodiment, the myosin-1F protein used in the method comprises a tail domain, including an SH3 domain, but lacks a myosin head domain. A preferred myosin-1F protein for use in the method consists essentially of an amino acid sequence having at least about 90%, more preferably at least about 95%, more preferably at least about 98% identity to residues 718-1098 in SEQ ID NO:2. An especially preferred myosin-1F protein for use in the method consists essentially of amino acids 718-1098 in SEQ ID NO:2.

In another preferred embodiment, the myosin-1F protein used in the method comprises an IQ domain and a tail domain, including an SH3 domain, but lacks a myosin head domain. A preferred myosin-1F protein for use in the method consists essentially of an amino acid sequence having at least about 90%, more preferably at least about 95%, more preferably at least about 98% identity to residues 695-1098 in SEQ ID NO:2. An especially preferred myosin-1F protein for use in the method consists essentially of amino acids 695-1098 in SEQ ID NO:2.

In another preferred embodiment, the myosin-1F protein used in the method comprises an IQ domain and a tail domain, including an SH3 domain. A preferred myosin-1F protein for use in the method consists essentially of an amino acid sequence having at least about 90%, more preferably at least about 95%, more preferably at least about 98% identity to residues 617-1098 in SEQ ID NO:2. An especially preferred myosin-1F protein for use in the method consists essentially of amino acids 617-1098 in SEQ ID NO:2.

In another preferred embodiment, the myosin-1F protein used in the method comprises a TH2 and SH3 domain, but lacks an IQ domain and a myosin head domain.

In another preferred embodiment, the myosin-1F protein used in the method comprises a myosin head domain and an IQ domain, but lacks a tail domain. A preferred myosin-1F protein for use in the method consists essentially of an amino acid sequence having at least about 90%, more preferably at least about 95%, more preferably at least about 98% identity to residues 1-717, 12-717 or 19-717 in SEQ ID NO:2. An especially preferred myosin-1F protein for use in the method consists essentially of amino acids 1-717, 12-717 or 19-717 in SEQ ID NO:2.

In another preferred embodiment, the myosin-1F protein used in the method comprises a myosin head domain, but lacks an IQ domain and a tail domain. A preferred myosin-1F protein for use in the method consists essentially of an amino acid sequence having at least about 90%, more preferably at least about 95%, more preferably at least about 98% identity to residues 19-677, 1-677, 12-691, or 1-691 in SEQ ID NO:2. An especially preferred myosin-1F protein for use in the method consists essentially of amino acids 19-677, 1-677, 12-691, or 1-691 in SEQ ID NO:2.

In another preferred embodiment, the myosin-1F protein used consists essentially of a partial myosin head domain. In a preferred embodiment, such a myosin-1F protein consists essentially of an amino acid sequence having at least about 85%, more preferably at least about 90%, more preferably at least about 95%, more preferably at least about 98% identity to the amino acid sequence set forth by residues 260-677 or 260-691 in SEQ ID NO:2. In an especially preferred embodiment, such a myosin-1F protein consists essentially of the amino acid sequence set forth by residues 260-677 or 260-691 in SEQ ID NO:2.

In another preferred embodiment, the myosin-1F protein consists essentially of a partial myosin head domain, an IQ domain, and a tail domain. In a preferred embodiment, such a myosin-1F protein consists essentially of an amino acid sequence having at least about 85%, more preferably at least about 90%, more preferably at least about 95%, more preferably at least about 98% identity to the amino acid sequence set forth by residues 260-1098 in SEQ ID NO:2. In an especially preferred embodiment, such a myosin-1F protein consists essentially of the amino acid sequence set forth by residues 260-1098 in SEQ ID NO:2. In another especially preferred embodiment, such a myosin-1F protein consists essentially of the amino acid sequence set forth by SEQ ID NO:4.

In another preferred embodiment, the myosin-1F protein used in the method comprises a myosin head domain, an IQ domain, and a tail domain. A preferred myosin-1F protein for use in the method consists essentially of an amino acid sequence having at least about 90%, more preferably at least about 95%, more preferably at least about 98% identity to SEQ ID NO:2. An especially preferred myosin-1F protein for use in the method comprises SEQ ID NO:2.

Bioactive agents that inhibit B-lymphocyte activation in these assays are useful as immunosuppressants.

By immunosuppressant is meant an agent that suppresses the body's ability to react to an antigen.

In another preferred embodiment, the methods comprise determining the ability of a candidate agent to modulate the binding of myosin-1F to a myosin-1F binding partner.

In a preferred embodiment, the methods comprise detecting modulation of the binding of myosin-1F protein to a myosin-1F binding partner in the presence of candidate agent, contacting the candidate bioactive agent to a B-lymphocyte, and determining lymphocyte activation in the presence of said candidate agent. In a preferred embodiment, lymphocyte activation in the presence and absence of candidate agent is determined. In a preferred embodiment, an agent that normally induces lymphocyte activation is used. Lymphocyte activation is measured in the presence, and optionally, the absence of candidate agent following contact with the agent that normally induces lymphocyte activation. A preferred activation agent for use with B lymphocytes is anti-IgM antibody.

In a preferred embodiment, the myosin-1F binding partner used is selected from the group consisting of WASP, BLNK, WASP-IP, Bee1p, Vrp1p, calmodulin, Arp2/3 complex, Acan125, ATP and actin.

In a preferred embodiment, the myosin-1F protein used in the method comprises a tail domain, including an SH3 domain, but lacks a myosin head domain. A preferred myosin-1F protein for use in the method consists essentially of an amino acid sequence having at least about 90%, more preferably at least about 95%, more preferably at least about 98% identity to residues 718-1098 in SEQ ID NO:2. An especially preferred myosin-1F protein for use in the method consists essentially of amino acids 718-1098 in SEQ ID NO:2.

In another preferred embodiment, the myosin-1F protein used in the method comprises an IQ domain and a tail domain, including an SH3 domain, but lacks a myosin head domain. A preferred myosin-1F protein for use in the method consists essentially of an amino acid sequence having at least about 90%, more preferably at least about 95%, more preferably at least about 98% identity to residues 695-1098 in SEQ ID NO:2. An especially preferred myosin-1F protein for use in the method consists essentially of amino acids 695-1098 in SEQ ID NO:2.

In another preferred embodiment, the myosin-1F protein used in the method comprises an IQ domain and a tail domain, including an SH3 domain. A preferred myosin-1F protein for use in the method consists essentially of an amino acid sequence having at least about 90%, more preferably at least about 95%, more preferably at least about 98% identity to residues 617-1098 in SEQ ID NO:2. An especially preferred myosin-1F protein for use in the method consists essentially of amino acids 617-1098 in SEQ ID NO:2.

In another preferred embodiment, the myosin-1F protein used in the method comprises a TH2 and TH3 domain, but lacks an IQ domain and a myosin head domain.

In another preferred embodiment, the myosin-1F protein used in the method comprises a myosin head domain and an IQ domain, but lacks a tail domain. A preferred myosin-1F protein for use in the method consists essentially of an amino acid sequence having at least about 90%, more preferably at least about 95%, more preferably at least about 98% identity to residues 1-717, 12-717 or 19-717 in SEQ ID NO:2. An especially preferred myosin-1F protein for use in the method consists essentially of amino acids 1-717, 12-717 or 19-717 in SEQ ID NO:2.

In another preferred embodiment, the myosin-1F protein used consists essentially of a partial myosin head domain. In a preferred embodiment, such a myosin-1F protein consists essentially of an amino acid sequence having at least about 85%, more preferably at least about 90%, more preferably at least about 95%, more preferably at least about 98% identity to the amino acid sequence set forth by residues 260-677 or 260-691 in SEQ ID NO:2. In an especially preferred embodiment, such a myosin-1F protein consists essentially of the amino acid sequence set forth by residues 260-677 or 260-691 in SEQ ID NO:2.

In another preferred embodiment, the myosin-1F protein consists essentially of a partial myosin head domain, an IQ domain, and a tail domain. In a preferred embodiment, such a myosin-1F protein consists essentially of an amino acid sequence having at least about 85%, more preferably at least about 90%, more preferably at least about 95%, more preferably at least about 98% identity to the amino acid sequence set forth by residues 260-1098 in SEQ ID NO:2. In an especially preferred embodiment, such a myosin-1F protein consists essentially of the amino acid sequence set forth by residues 260-1098 in SEQ ID NO:2. In another especially preferred embodiment, such a myosin-1F protein consists essentially of the amino acid sequence set forth by SEQ ID NO:4.

In another preferred embodiment, the myosin-1F protein used in the method comprises a myosin head domain, but lacks an IQ domain and a tail domain. A preferred myosin-1F protein for use in the method consists essentially of an amino acid sequence having at least about 90%, more preferably at least about 95%, more preferably at least about 98% identity to residues 19-677, 1-677, 12-691, or 1-691 in SEQ ID NO:2. An especially preferred myosin-1F protein for use in the method consists essentially of amino acids 19-677, 1-677, 12-691, or 1-691 in SEQ ID NO:2.

In another preferred embodiment, the myosin-1F protein used in the method comprises a myosin head domain, an IQ domain, and a tail domain. A preferred myosin-1F protein for use in the method consists essentially of an amino acid sequence having at least about 90%, more preferably at least about 95%, more preferably at least about 98% identity to SEQ ID NO:2. An especially preferred myosin-1F protein for use: in the method comprises SEQ ID NO:2.

By modulation of the binding of myosin-1F protein to myosin-1F binding partner is meant a detectable increase or decrease in binding as compared to binding in the absence of agent, or absence of binding.

Bioactive agents that inhibit B-lymphocyte activation in these assays are useful as immunosuppressants.

In another preferred embodiment, the methods comprise determining the ability of a candidate bioactive agent to modulate the activity of a myosin-1F protein.

In a preferred embodiment, the methods comprise detecting modulation of the ATPase activity of myosin-1F in the presence of candidate bioactive agent, contacting: the candidate bioactive agent to a B-lymphocyte, and determining lymphocyte activation in the presence of said candidate agent. In a preferred embodiment, lymphocyte activation in the presence and absence of candidate agent is determined. In a preferred embodiment, an agent that normally induces lymphocyte activation is used. Lymphocyte activation is measured in the presence, and optionally, the absence of candidate agent following contact with the agent that normally induces lymphocyte activation. A preferred activation agent for use with B lymphocytes is anti-IgM antibody.

In another preferred embodiment, the methods comprise detecting modulation of the actin polymerization-inducing activity of myosin-1F in the presence of candidate bioactive agent, contacting the candidate bioactive agent to a B-lymphocyte, and determining lymphocyte activation in the presence of said candidate agent. In a preferred embodiment, lymphocyte activation in the presence and absence of candidate agent is determined. In a preferred embodiment, an agent that normally induces lymphocyte activation is used. Lymphocyte activation is measured in the presence, and optionally, the absence of candidate agent following contact with the agent that normally induces lymphocyte activation. A preferred activation agent for use with B lymphocytes is anti-IgM antibody.

In a preferred embodiment, the myosin-1F protein used in the method comprises a myosin head domain and an IQ domain, but lacks a tail domain. A preferred myosin-1F protein for use in the method consists essentially of an amino acid sequence having at least about 90%, more preferably at least about 95%, more preferably at least about 98% identity to residues 1-717, 12-717, or 19-717 in SEQ ID NO:2. An especially preferred myosin-1F protein for use in the method consists essentially of amino acids 1-717, 12-717, or 19-717 in SEQ ID NO:2.

In another preferred embodiment, the myosin-1F protein used in the method comprises a myosin head domain, but lacks a tail domain and an IQ domain. A preferred myosin-1F protein for use in the method consists essentially of an amino acid sequence having at least about 90%, more preferably at least about 95%, more preferably at least about 98% identity to residues 19-677, 1-677, 12-691, or 1-691 in SEQ ID NO:2. An especially preferred myosin-1F protein for use in the method comprises residues 19-677, 1-677, 12-691, or 1-691 in SEQ ID NO:2.

In another preferred embodiment, the myosin-1F protein used in the method comprises a myosin head domain, an IQ domain, and a tail domain. A preferred myosin-1F protein for use in the method consists essentially of an amino acid sequence having at least about 90%, more preferably at least about 95%, more preferably at least about 98% identity to SEQ ID NO:2. An especially preferred myosin-1F protein for use in the method consists essentially of SEQ ID NO:2.

In another preferred embodiment, the methods comprise detecting a change in ATP-dependent actin binding activity of myosin-1F in the presence of candidate bioactive agent, contacting the candidate bioactive agent to a B-lymphocyte, and determining lymphocyte activation in the presence of said candidate agent. In a preferred embodiment, lymphocyte activation in the presence and absence of candidate agent is determined. In a preferred embodiment, an agent that normally induces lymphocyte activation is used. Lymphocyte activation is measured in the presence, and optionally, the absence of candidate agent following contact with the agent that normally induces lymphocyte activation. A preferred activation agent for use with B lymphocytes is anti-IgM antibody.

In a preferred embodiment, the myosin-1F protein used in the method comprises a myosin head domain and an IQ domain, but lacks a tail domain. A preferred myosin-1F protein for use in the method consists essentially of an amino acid sequence having at least about 90%, more preferably at least about 95%, more preferably at least about 98% identity to residues 1-717, 12-717, or 19-717 in SEQ ID NO:2. An especially preferred myosin-1F protein for use in the method consists essentially of amino acids 1-717, 12-717, or 19-717 in SEQ ID NO:2.

In another preferred embodiment, the myosin-1F protein used in the method comprises a myosin head domain, but lacks a tail domain and an IQ domain. A preferred myosin-1F protein for use in the method consists essentially of an amino acid sequence having at least about 90%, more preferably at least about 95%, more preferably at least about 98% identity to residues 19-677, 1-677, 12-691, or 1-691 in SEQ ID NO:2. An especially preferred myosin-1F protein for use in the method comprises residues 19-677, 1-677, 12-691, or 1-691 in SEQ ID NO:2.

In another preferred embodiment, the myosin-1F protein used in the method comprises a myosin head domain, an IQ domain, and a tail domain. A preferred myosin-1F protein for use in the method consists essentially of an amino acid sequence having at least about 90%, more preferably at least about 95%, more preferably at least about 98% identity to SEQ ID NO:2. An especially preferred myosin-1F protein for use in the method consists essentially of SEQ ID NO:2.

By modulation of the ATPase activity of myosin-1F is meant a detectable increase or decrease in the ability of myosin-1F to hydrolyze ATP as compared to its ability to hydrolyze ATP in the absence of agent, or loss of the ability to hydrolyze ATP.

By modulation of the actin polymerization-inducing activity is meant a detectable increase or decrease in the ability of myosin-1F to induce the polymerization of actin as compared to its ability to induce the polymerization of actin in the absence of agent, or loss of the ability induce the polymerization of actin.

By change in actin ATP-dependent actin binding activity is meant a detectable increase or decrease in the ability of myosin-1F to bind actin in an ATP-dependent manner as compared to its ability to do so in the absence of agent, or loss of the ability to bind actin in an ATP-dependent manner Bioactive agents that inhibit B-lymphocyte activation in these assays are useful as immunosuppressants.

Additional methods of screening for immunosuppressants are provided herein. In a preferred embodiment, the methods comprise detecting binding of candidate agent to myosin-1F protein, contacting the candidate bioactive agent to a B-lymphocyte, and determining CD23 expression in the presence of said candidate agent. In a preferred embodiment, CD23 expression in the presence and absence of candidate agent is determined. In a preferred embodiment, an agent that normally induces CD23 expression is used. Lymphocyte activation is measured in the presence, and optionally, the absence of candidate agent following contact with the agent that normally induces CD23 expression. Preferred CD23 inducing agents are IL-4, CD40L, and the combination of IL-4 and CD40L.

Bioactive agents that inhibit CD23 induction in these assays are useful as immunosuppressants.

In a preferred embodiment, the methods comprise detecting modulation of the binding of myosin-1F protein to a myosin-1F binding partner in the presence of candidate agent, contacting the candidate bioactive agent to a B-lymphocyte, and determining CD23 expression in the presence of said candidate agent. In a preferred embodiment, CD23 expression in the presence and absence of candidate agent is determined. In a preferred embodiment, an agent that normally induces CD23 expression is used. Lymphocyte activation is measured in the presence, and optionally, the absence of candidate agent following contact with the agent that normally induces CD23 expression. Preferred CD23 inducing agents are IL4, CD40L, and the combination of IL4 and CD40L.

In an especially preferred embodiment, the myosin-1F binding partner used in these methods is selected from the group consisting of WASP, BLNK, WASP-IP, Bee1p, Vrp1p, calmodulin, Arp2/3 complex, Acan125, ATP and actin.

Bioactive agents that inhibit CD23 induction in these assays are useful as immunosuppressants.

In a preferred embodiment, the methods comprise detecting modulation of ATPase activity, or modulation of actin binding activity, or modulation of actin polymerization inducing activity of myosin-1F in the presence of candidate bioactive agent, contacting the candidate bioactive agent to a B-lymphocyte, and determining CD23 expression in the presence of said candidate agent. In a preferred embodiment, CD23 expression in the presence and absence of candidate agent is determined. In a preferred embodiment, an agent that normally induces CD23 expression is used. Lymphocyte activation is measured in the presence, and optionally, the absence of candidate agent following contact with the agent that normally induces CD23 expression. Preferred CD23 inducing agents are IL4, CD40L, and the combination of IL4 and CD40L.

Bioactive agents that inhibit CD23 induction in these assays are useful as immunosuppressants.

In a preferred embodiment, the methods comprise detecting binding of candidate agent to myosin-1F protein, contacting the candidate bioactive agent to a resting B-lymphocyte, and determining the level of surface Ig expression; preferably surface IgM expression, in the cell. Particularly preferred are Ramos cells and primary B-cells.

In a preferred embodiment, the methods comprise detecting modulation of the binding of myosin-1F protein to a myosin-1F binding partner in the presence of candidate agent, contacting the candidate bioactive agent to a resting B-lymphocyte, and determining the level of surface Ig expression, preferably surface IgM expression, in the cell. Particularly preferred are Ramos cells and primary B-cells.

In a preferred embodiment, the methods comprise detecting modulation of ATPase activity, or modulation of actin binding activity, or modulation of actin polymerization inducing activity of myosin-1F in the presence of candidate bioactive agent, contacting the candidate bioactive agent to a resting B-lymphocyte, and determining the level of surface Ig-expression, preferably surface IgM expression, in the cell. Particularly preferred are Ramos cells and primary B-cells.

Agents that decrease surface Ig expression in resting B-cells are particularly preferred, and are useful as immunosuppressants.

In another preferred embodiment, the level of myosin-1F mRNA expression, myosin-1F protein expression, or myosin-1F activity is used to screen for agents that modulate the level of myosin-1F activity in B-lymphocytes. In a preferred embodiment, such agents inhibit B-lymphocyte activation and are useful as immunosuppressants.

In a preferred embodiment, candidate bioactive agents used in these assays are small molecule chemical compounds, from about 100 to about 1500, more preferably about 100 to about 1200, more preferably about 100 to about 1000, more preferably about 200 to about 500 daltons.

In a preferred embodiment, a library of candidate bioactive agents is contacted to myosin-1F protein.

In another preferred embodiment, a library of candidate agents is contacted to a population of cells comprising myosin-1F.

In a preferred embodiment, determining lymphocyte activation in the methods herein comprises determining the level of expression of a surface marker which is associated with activation of a B-lymphocyte, in the presence of candidate agent. In a preferred embodiment, the level of surface marker expression is determined in the presence and absence of candidate agent. In a preferred embodiment, the surface marker is selected from the group consisting of CD69, CD23, CD80 and CD86. In an especially preferred embodiment, the surface marker used is CD69.

In another preferred embodiment, determining lymphocyte activation in the methods herein comprises determining the level of activity of a promoter in the presence of candidate agent, which activity correlates with B-lymphocyte activation in the absence of candidate agent. In a preferred embodiment, the level of promoter activity is determined in the presence and absence of candidate agent. In a preferred embodiment the promoter is an NFAT-responsive promoter, such as the IL-2 promoter. In an especially preferred embodiment, the promoter is the IgH promoter.

In a preferred embodiment, determining B-lymphocyte activation involves measuring lymphocyte activation using a FACS machine. In a preferred embodiment, lymphocytes are sorted by FACS on the basis of activation.

Similarly, in a preferred embodiment, determining surface Ig, preferably surface IgM expression in a resting B-lymphocyte is done using a FACS machine. In a preferred embodiment, lymphocytes are sorted by FACS on the basis of surface Ig expression.

In some embodiments, the methods involve determining B-lymphocyte activation by other means, which may also include the use of a FACS machine. As will be appreciated, lymphocyte activation can be determined in a number of ways. For a review of B-cell activation and methods of measuring, see Clark et al., Ann. Rev. Immunol., 9:97-127, 1993, and references therein. It will be appreciated that mechanisms of leukocyte and platelet activation and methods for determining activation are known (see for example Kay, Immunol. Invest. 17:679-705, 1988; Lukacs et. al., Chem. Immunol. 72:102-120, 1999; Stankunas et al., Cold Spring Harbor Symposia on Quant. Biol., 64: 505-516, 1999; Metcalf et. al., Physiol. Rev. 77:1033-1079, 1997;

Hematol. Oncol. Clin. North Am. 4:1-26, 1990; Brass et. al., Adv. Exp. Med. Biol., 344:17-36, 1993; Brass et. al., Thromb. Haemost., 70:217-223, 1993; *Cellular and Molecular Immunology*, Abbas et. al., W. B. Saunders, ISBN 0-7216-3032-4, Chapters 7, 9, 12, and 14). Particularly relevant are the methods disclosed by Holland et al., J. Exp. Med., 194:1263-1276, 2001, expressly incorporated herein by reference.

In some embodiments, indicators of lymphocyte activation are used. There are a number of parameters that may be evaluated or assayed to determine lymphocyte activation, including, but not limited to, IgH promoter activity, calcium flux, NFAT activity, Ig secretion, IgG and IgM production, lymphocyte proliferation, expression cell surface markers correlated with lymphocyte activation, cytokine production, intracellular calcium levels, release of calcium from intracellular stores, amount of SYK protein, level of SYK protein ubiquitination, SYK protein tyrosine kinase activity, and IL-2 expression. These parameters may be assayed and used as indicators to evaluate the effect of candidate drug agents on lymphocyte activation. In this manner, rapid, accurate screening of candidate agents may be performed to identify agents that modulate lymphocyte activation.

By a "population of cells" or "library of cells" herein is meant at least two cells, with at least about $10^3$ being preferred, at least about $10^6$ being particularly preferred, and at least about $10^8$ to $10^9$ being especially preferred. The population or sample can contain a mixture of different cell types from either primary or secondary cultures although samples containing only a single cell type are preferred, for example, the sample can be from a cell line, particularly tumor cell lines, as outlined below. In a preferred embodiment, cells that are replicating or proliferating are used; this may allow the use of retroviral vectors for the introduction of candidate bioactive agents. Alternatively, non-replicating cells may be used, and other vectors (such as adenovirus and lentivirus vectors) can be used. In addition, although not required, the cells are compatible with dyes and antibodies.

Preferred cell types for use in the invention include, but are not limited to, mammalian cells, including animal (rodents, including mice, rats, hamsters and gerbils), primates, and human cells, particularly including tumor cells of all types, including breast, skin, lung, cervix, colonrectal, leukemia, brain, etc. More preferable cell types include the Ig(+) and IgM secreting B-cell lines CL-01, LA350, BJAB, and CA46. Primary cells are also preferred, including peripheral blood lymphocytes (PBLs) and peripheral blood mononuclear cells (PBMCs). Ramos cells (B-cell cell line) are also preferred.

In the methods provided herein requiring the use of B-lymphocytes, B-lymphocyte-like cells or B-lymphocyte cell lines, such as those described above, or primary B-lymphocytes may be used.

Preferred cell surface markers useful as indicators of B-lymphocyte activation in the methods herein exhibit low background expression in the absence of lymphocyte activation. Especially preferred cell surface markers include CD69, CD23, CD80, CD86. CD69 and CD23 are especially preferred.

Agents that recognize such surface-molecules (e.g. antibodies) can be used as an affinity ligand, and attached to a solid support such as a bead, a surface, etc., and used to pull out B-cells that are undergoing activation. Similarly, these agents can be coupled to a fluorescent dye such as PerCP, and then assayed using a FACS machine, and cells may be optionally sorted on this basis.

FACS analysis can be used in conjunction with antibodies recognizing lymphocyte surface markers that are correlated with lymphocyte activation. A FACS machine is used to analyze, and optionally sort cells based on the expression of these markers to detect unstimulated and stimulated lymphocytes. In a preferred embodiment, sorted lymphocytes are used to retrieve candidate bioactive agents introduced thereto.

In a preferred embodiment, IgH promoter activity and NFAT activity are measured using lymphocyte clones comprising an IgH promoter or an NFAT-responsive promoter (such as IL-2 promoter) operably linked to a reporter gene. For example, a surface Ig(+), IgM secreting B-cell line such as the BJAB, CL-01, CA46, or LA350 cell line is transfected with a construct comprising GFP/2a/TK fusion under the control of an IgH promoter, Eµ and 3'α enhancer elements. Stable transfectants (referred to herein as immunoglobulin heavy chain reporter cell lines) are selected and maintained in gancyclovir. Preferred immunoglobulin heavy chain reporter cell lines for use in the present invention exhibit low background GFP expression and strong basal activity and/or inducible activity in the presence of positive control. Such cell lines can be generated with the use of retroviral constructs.

Release of calcium from intracellular calcium stores may be assayed using membrane permeant vital calcium sensing fluorescent dyes, as are well known in the art. For example, see Calcium Green™, Calcium Orange™, from Molecular Probes, Eugene, Oreg., catalog numbers C-3010, C-3013, for example.

A preferred embodiment utilizes a cell proliferation assay. For example, B-cells proliferate when activated. By "proliferation assay" herein is meant an assay that allows the determination that a cell population is either proliferating, i.e. replicating, or not proliferating.

In a preferred embodiment, the proliferation assay is a dye inclusion assay. A dye inclusion assay relies on dilution effects to distinguish between proliferating and non-proliferating cells. Briefly, a dye (generally a fluorescent dye as outlined below) is introduced to cells and taken up by the cells. Once taken up, the dye is trapped in the cell, and does not diffuse out. As the cell population divides, the dye is proportionally diluted. That is, after the introduction of the inclusion dye, the cells are allowed to incubate for some period of time; cells that lose fluorescence over time are dividing, and the cells that remain fluorescent are arrested in a non-growth phase.

The rate of loss of fluorescence is indicative of the rate of proliferation. An increase in proliferation rate above that of unstimulated cells is indicative of B-cell activation.

These methods may also be applied to platelets.

Generally, the introduction of the inclusion dye may be done in one of two ways. Either the dye cannot passively enter the cells (e.g. it is charged), and the cells must be treated to take up the dye; for example through the use of an electric pulse. Alternatively, the dye can passively enter the cells, but once taken up, it is modified such that it cannot diffuse out of the cells. For example, enzymatic modification of the inclusion dye may render it charged, and thus unable to diffuse out of the cells. For example, the Molecular Probes CellTracker™ dyes are fluorescent chloromethyl derivatives that freely diffuse into cells, and then glutathione S-transferase-mediated reaction produces membrane impermeant dyes.

Suitable inclusion dyes include, but are not limited to, the Molecular Probes line of CellTracker™ dyes including, but not limited to CellTracker™ Blue, CellTracker™ Yellow- Green, CellTracker™ Green, CellTracker™ Orange, PKH26 (Sigma), and others known in the art; see the Molecular Probes Handbook; chapter 15 in particular.

In general, inclusion dyes are provided to the cells at a concentration ranging from about 100 ng/ml to about 5 μg/ml, with from about 500 ng/ml to about 1 μg/ml being preferred. A wash step may or may not be used. In a preferred embodiment, a candidate bioactive agent is combined with the cells as described herein. The cells and the inclusion dye are incubated for some period of time, to allow cell division and thus dye dilution.

Without being bound by theory, it is recognized herein that myosin-1F proteins are involved in the regulation of signal transduction in B-lymphocytes and platelets. Particularly, myosin-1F proteins are recognized herein as being critical regulators of B-cell activation as well as platelet proliferation. As discussed above, the activation of specific signaling pathways in lymphocytes determines the quality, magnitude, and duration of immune responses. In transplantation, acute and chronic inflammatory diseases, and autoimmunity, it is these pathways that are responsible for the induction, maintenance and exacerbation of undesirable lymphocyte responses.

Accordingly, in one aspect, the invention provides compositions and methods for the treatment of B-lymphocyte activation disorders and platelet activation or proliferation disorders, as described below.

In a preferred embodiment, the present invention provides myosin-1F proteins and nucleic acids, as well as agents that bind to them and/or modulate their activity, including and preferably small molecule chemical compositions as discussed herein, which are useful in the treatment of acute and chronic inflammatory diseases and autoimmune diseases, as well as in the treatment of a host receiving a transplant. Among these diseases are those listed in FIG. 5.

In another preferred embodiment, the present invention provides myosin-1F proteins and nucleic acids, as well as agents that bind to them and/or modulate their activity, including and preferably small molecule chemical compositions as discussed herein, which are useful in the treatment of physiological states that are characterized by or lead to the presentation of some or all symptoms characteristic of acute inflammatory disease, chronic inflammatory disease, autoimmune disease, or response to transplantation.

It will be understood that these diseases and states may or may not be associated with altered myosin-1F activity. That is, myosin-1F compositions (proteins, nucleic acids, antimyosin-1F antibodies, agonists, antagonists) find use in the prevention and/or treatment of diseases and states which do not have myosin-1F dysregulation or dysfunction as a molecular basis, but still involve lymphocyte activation or platelet proliferation. That is, a disease or state need not be associated with myosin-1F activity for the present compositions and methods to be useful in preventing or treating it. Many autoimmune diseases fall into this category.

In another preferred embodiment, the present invention provides myosin-1F proteins and nucleic acids, as well as agents that bind to them and/or modulate their activity, including and preferably small molecule chemical compositions as discussed herein, which are useful as prophylactics for the prevention of acute inflammatory disease, chronic inflammatory disease, autoimmune disease, and response to transplantation.

In a preferred embodiment, the present invention provides myosin-1F proteins and nucleic acids, as well as agents that bind to them and/or modulate their activity, including and preferably small molecule chemical compositions as discussed herein, which are useful as prophylactics for the prevention of physiological states that are characterized by or lead to the presentation of some or all symptoms characteristic of acute inflammatory disease, chronic inflammatory disease, autoimmune disease, or response to transplantation.

In a preferred embodiment, myosin-1F proteins and nucleic acids provided herein are useful for the modulation of antigen receptor-induced B-lymphocyte activation, as characterized by the induction of CD69 and other markers of activation.

In an especially preferred embodiment, myosin-1F proteins and nucleic acids provided herein are useful for the modulation of immunoglobulin production by B-lymphocytes that normally results from BCR activation by antigen.

Particularly useful for these purposes is a myosin-1F variant protein comprising an SH3 domain having a point mutation which disrupts binding to a myosin-1F binding partner. Another myosin-1F protein particularly useful for this purpose is a variant myosin-1F protein comprising a myosin head domain having a point mutation in the ATP-binding domain which is incapable of hydrolyzing ATP.

Another myosin-1F protein particularly useful for this purpose consists essentially of amino acids 617-1098 in SEQ ID NO:2. Another myosin-1F protein particularly useful for this purpose consists essentially of a polynucleotide encoded by SEQ ID NO:5.

Without being bound by theory, myosin-1F proteins, being modulators of signal transduction in B-lymphocytes, particularly signal transduction events underlying B-lymphocyte activation, are involved in the regulation of proliferation of B-lymphocytes, and have utility as modulators of lymphocyte proliferation. Further, disorders associated with myosin-1F dysfunction or dysregulation include lymphocyte proliferation disorders, such as B-cell leukemias, lymphomas, and Wiskoft-Aldrich syndrome.

Accordingly, in a preferred embodiment, the present invention provides myosin-1F proteins and nucleic acids, as well as agents capable of binding to them or modulating their activity, including and preferably small molecule chemical compositions as discussed herein, which are useful in the treatment of disorders involving B-cell proliferation, including leukemias, lymphomas, and Wiskott-Aldrich syndrome.

Without being bound by theory, myosin-1F proteins, being modulators of signal transduction in platelets, are involved in the regulation of proliferation of platelets, and have utility as modulators of platelet proliferation. Further, disorders associated with myosin-1F dysfunction or dysregulation include platelet proliferation disorders, such as Wiskott-Aldrich syndrome.

It is recognized in the art that signaling pathways involved in the regulation of cell proliferation frequently participate in, directly or indirectly, the regulation of cell survival and programmed cell death. It is further recognized in the art that the dysregulation of mechanisms of programmed cell death can lead to cancer, particularly in lymphocytes. For example, overexpression of Bcl-2, which promotes cell survival through the inhibition of apoptotic processes, is thought to be responsible for the survival of excessive numbers of lymphocytes in a form of lymphoma (Reed et al., Science, 236:1295-1299, 1987; Tsujimoto et al., Science, 228:1440-1443, 1985).

Accordingly, the present invention provides myosin-1F proteins and nucleic acids, as well as agents capable of binding to them and/or modulating their activity, including and preferably small molecule chemical compositions as discussed herein, which are useful in the treatment of disorders involving B-cell survival and programmed cell death, including cancer.

The proteins and nucleic acids provided herein can also be used for screening purposes wherein the protein-protein interactions of the myosin-1F proteins can be identified. Genetic systems have been described to detect protein-protein interactions. The first work was done in yeast systems, namely the "yeast two-hybrid" system. The basic system requires a protein-protein interaction in order to turn on transcription of a reporter gene. Subsequent work was done in mammalian cells. See Fields et al., Nature 340:245 (1989); Vasavada et al., PNAS USA 88:10686 (1991); Fearon et al., PNAS USA 89:7958 (1992); Dang et al., Mol. Cell. Biol. 11:954 (1991); Chien et al., PNAS USA 88:9578 (1991); and U.S. Pat. Nos. 5,283,173, 5,667,973, 5,468,614, 5,525,490, and 5,637,463. A preferred system is described in Ser. No. 09/050,863, filed Mar. 30, 1998 and Ser. No. 09/359,081 filed Jul. 22, 1999, entitled "Mammalian Protein Interaction Cloning System". For use in conjunction with these systems, a particularly useful shuttle vector is described in Ser. No. 09/133,944, filed Aug. 14, 1998, entitled "Shuttle Vectors".

In general, two nucleic acids are transformed into a cell, where one is a "bait" such as the gene encoding a myosin-1F protein or a portion thereof, and the other encodes a test candidate. Only if the two expression products bind to one another will an indicator, such as a fluorescent protein, be expressed. Expression of the indicator indicates when a test candidate binds to the myosin-1F protein, and identifies the candidate as being part of a B-cell or platelet myosin-1F signaling pathway. A test candidate so identified may then be used as bait to identify binding proteins that are also identified as being part of a B-cell or platelet myosin-1F signaling pathway. Additionally, myosin-1F proteins may be used to identify new baits, or agents that bind to myosin-1F proteins. Additionally, the two-hybrid system can be used wherein a test candidate is added in addition to the bait and the myosin-1F protein encoding nucleic acids to determine agents which interfere with the binding of bait to the myosin-1F protein.

In one embodiment, a mammalian two-hybrid system is preferred. Mammalian systems provide post-translational modifications of proteins which may contribute significantly to their ability to interact. In addition, a mammalian two-hybrid system can be used in a wide variety of mammalian cell types to mimic the regulation, induction, processing, etc. of specific proteins within a particular cell type. For example, proteins involved in a disease state (i.e., cancer, apoptosis related disorders) could be tested in the relevant disease cells. Similarly, for testing of random proteins, assaying them under the relevant cellular conditions will give the highest positive results. Furthermore, the mammalian cells can be tested under a variety of experimental conditions that may affect intracellular protein-protein interactions, such as in the presence of hormones, drugs, growth factors and cytokines, radiation, chemotherapeutics, cellular and chemical stimuli, etc., that may contribute to conditions which can affect protein-protein interactions.

Assays involving binding such as the two-hybrid system may take into account non-specific binding proteins (NSB).

Expression in various cell types, and assays for myosin-1F activity are described above. The activity assays can be performed to confirm the activity of myosin-1F proteins which have already been identified by their sequence identity/similarity to myosin-1F (SEQ ID NO:2), as well as to further confirm the activity of lead compounds identified as modulators of myosin-1F activity.

The components provided herein for the assays provided herein may also be combined to form kits. The kits can be based on the use of myosin-1F proteins and/or nucleic acids encoding myosin-1F proteins. In one embodiment, other components are provided in the kit. Such components include one or more of packaging, instructions, antibodies, and labels. Additional assays such as those used in diagnostics are further described below.

Bioactive agents may be identified by the methods provided herein. Compounds with pharmacological activity are able to enhance or interfere with the activity of the myosin-1F protein. The compounds having the desired pharmacological activity may be administered in a physiologically acceptable carrier to a host, as further described below.

The present discovery relating to the role of myosin-1F proteins B-lymphocytes thus provides methods for inducing or preventing B-lymphocyte activation and platelet proliferation. In a preferred embodiment, the myosin-1F proteins, and particularly myosin-1F protein fragments, are useful in the study or treatment of conditions which involve dysfunction or dysregulation of myosin-1F protein activity, i.e. to diagnose, treat or prevent myosin-1F associated disorders. "Myosin-1F associated disorders" or "disease states" or "physiological states associated with myosin-1F dysfunction or dysregulation" include conditions involving insufficient, excessive, and inappropriate myosin-1F activity. Among these disorders are B-lymphocyte activation disorders, and platelet proliferation disorders.

Thus, in one embodiment, methods for regulating B-lymphocyte activation in cells or organisms are provided. In one embodiment, the methods comprise administering to a cell or individual, a myosin-1F protein in a therapeutic amount. Alternatively, an anti-myosin-1F antibody that reduces or eliminates the biological activity of the endogenous myosin-1F protein is administered. Particularly preferred are intrabodies, which are useful for the inhibition of intracellular myosin-1F protein in situ. The use of intrabodies is known in the art, for example, see Marasco, Curr. Top. Microbiol. Immunol. 260:247-270, 2001. Alternatively and preferably a myosin-1F dominant negative protein variant is administered. In another embodiment, a bioactive agent as identified by the methods provided herein is administered. In a further preferred embodiment, a small molecule chemical composition which inhibits myosin-1F activity is administered. Alternatively, the methods comprise administering to a cell or individual a recombinant nucleic acid encoding a myosin-1F protein. In one embodiment, nucleic acid encoding a myosin-1F dominant negative variant protein is administered. In another embodiment, a myosin-1F antisense nucleic acid is administered. In another embodiment, a myosin-1F RNAi is administered. RNAi's are well known in the art, for example, see Caplan, Trends in Biotechnology, 20: 49-51, 2002.

In one embodiment, the activity of myosin-1F is increased. As will be appreciated by those in the art, this may be accomplished in any number of ways. In a preferred embodiment, the activity of myosin-1F is increased by increasing the amount of myosin-1F in the cell, for example by overexpressing the endogenous myosin-1F or by administering a gene encoding a myosin-1F protein, using known gene-therapy techniques, for example. In a preferred embodiment, the gene therapy techniques include the incorporation of the exogenous gene using enhanced homologous recombination (EHR), for example as described in PCT/US93/03868, hereby incorporated by reference in its entirety. Alternatively, myosin-1F activity may be increased by administering an agent determined to increase myosin-1F activity or expression by the methods provided herein.

In one embodiment, the activity of myosin-1F is decreased. As will be appreciated by those in the art, this may be accomplished in any number of ways. In a preferred embodiment, the activity of myosin-1F is decreased by decreasing the amount of myosin-1F mRNA in the cell, for example by expressing myosin-1F antisense RNA. Double stranded nucleic acids for use in RNA interference (see Caplan, Trends in Biotechnology, 20: 49-51, 2002) are also preferred for this purpose. Alternatively, endogenous myosin-1F activity is decreased by administering a dominant negative myosin-1F protein or a gene encoding a dominant negative myosin-1F protein. Alternatively, endogenous myosin-1F activity is decreased by administering anti-myosin-1F antibody or a gene encoding anti-myosin-1F antibody or an epitope recognizing portion thereof. Particularly preferred are intrabodies, which are useful for the inhibition of intracellular myosin-1F protein in situ. Known gene-therapy techniques may be used to administer these agents. In a preferred embodiment, the gene therapy techniques involve incorporation of the exogenous gene into the host genome using enhanced homologous recombination (EHR), for example as described in PCT/US93/03868, hereby incorporated by reference in its entirety. Alternatively, myosin-1F activity may be decreased by administering an agent determined to decrease myosin-1F activity or expression by the methods provided herein.

It appears that myosin-1F protein is an important protein in B-lymphocyte activation and platelet proliferation. Accordingly, disorders based on mutant or variant myosin-1F genes may be determined. In one embodiment, the invention provides methods for identifying cells containing variant myosin-1F genes comprising determining all or part of the sequence of at least one endogenous myosin-1F gene in a cell. As will be appreciated by those in the art, this may be done using any number of sequencing techniques. In a preferred embodiment, the invention provides methods of identifying the myosin-1F genotype of an individual comprising determining all or part of the sequence of at least one myosin-1F gene of the individual. This is generally done in at least one tissue of the individual, and may include the evaluation of a number of tissues or different samples of the same tissue. The method may include comparing the sequence of the sequenced myosin-1F gene to a known myosin-1F gene, i.e. a wild-type gene.

The sequence of all or part of the myosin-1F gene can then be compared to the sequence of a known myosin-1F gene to determine if any differences exist. This can be done using any number of known sequence identity programs, such as Bestfit, etc. In a preferred embodiment, the presence of a difference in the sequence between the myosin-1F gene of the patient and the known myosin-1F gene is indicative of a disease state or a propensity for a disease state, particularly a B-lymphocyte activation disorder or a platelet proliferation disorder.

In one embodiment, the invention provides methods for diagnosing a myosin-1F related condition in an individual. The methods comprise measuring the activity of myosin-1F in a tissue from the individual or patient, which may include a measurement of the amount or specific activity of a myosin-1F protein. This activity is compared to the activity of myosin-1F from either an unaffected second individual or from an unaffected tissue from the first individual. When these activities are different, the first individual may be at risk for a myosin-1F associated disorder. In this way, for example, monitoring of various disease conditions may be done by monitoring the absolute myosin-1F activity in a sample or the specific activity of a myosin-1F protein from a sample. Similarly, activity levels may correlate with prognosis.

In a preferred embodiment, myosin-1F activity levels are determined in B-lymphocytes of an affected individual. In another preferred embodiment, myosin-1F activity levels are determined in platelets of an affected individual.

In one aspect, the expression levels of myosin-1F genes (encoding myosin-1F proteins) are determined in different patient samples or cells for which either diagnostic or prognostic information is desired. Gene expression monitoring is done on genes encoding myosin-1F proteins. In one aspect, the expression levels of myosin-1F genes are determined for different cellular states, such as normal cells and activated cells. By comparing myosin-1F gene expression levels in cells in different states, information including both up- and down-regulation of myosin-1F genes is obtained, which can be used in a number of ways. For example, the evaluation of a particular treatment regime may be evaluated: does a chemotherapeutic drug act to improve the long-term prognosis in a particular patient. Similarly, diagnosis may be done or confirmed by comparing patient samples. Furthermore, these gene expression levels allow screening of drug candidates with an eye to mimicking or altering a particular expression level. This may be done by making biochips comprising probes that determine the presence of myosin-1F genes, which biochips can be used in these screens. These methods can also be done on the protein basis; that is, myosin-1F protein expression levels can be evaluated for diagnostic and prognostic purposes or to screen candidate agents for their effects on myosin-1F protein expression. ELISA methods, and array-based protein detection methods are know to those skilled in the art.

In a preferred embodiment; myosin-1F expression levels are determined in B-lymphocytes in the presence of candidate agents. This determination is done to screen for agents capable of modulating myosin-1F expression, which find use as immunosuppressants and as agents for the inhibition of B-lymphocyte activation.

In a preferred embodiment, nucleic acid probes to myosin-1F nucleic acids and their complements are made. The nucleic acid probes are designed to be substantially complementary to myosin-1F nucleic acids, i.e., the target sequence, such that hybridization of the target sequence and the probe occurs. As outlined below, this complementarity need not be perfect; there may be any number of base pair mismatches which will interfere with hybridization between the target sequence and the single stranded nucleic acids of the present invention. However, if the number of mismatches is so great that no hybridization can occur under even the least stringent of hybridization conditions, the sequence is not a complementary target sequence. Thus, by "substantially complementary" herein is meant that the probes are sufficiently complementary to the target sequences to hybridize under normal reaction conditions, particularly high stringency conditions, as outlined herein.

A "nucleic acid probe" is generally single stranded but can be partially single and partially double stranded. The strandedness of the probe is dictated by the structure, composition, and properties of the target sequence. In general, the nucleic acid probes range from about 8 to about 100 bases long, with from about 10 to about 80 bases being preferred, and from about 30 to about 50 bases being particularly preferred. In some embodiments, much longer nucleic acids can be used, up to hundreds of bases (e.g., whole genes).

As will be appreciated by those in the art, nucleic acids can be attached or immobilized to a solid support in a wide variety of ways. By "immobilized" and grammatical equivalents herein is meant the association or binding between the nucleic acid probe and the solid support is sufficient to be stable under the conditions of binding, washing, analysis, and removal. The binding can be covalent or non-covalent. By "non-covalent binding" and grammatical equivalents herein is meant one or more of either electrostatic, hydrophilic, and hydrophobic interactions. Included in non-covalent binding is the covalent attachment of a molecule, such as, streptavidin to the support and the non-covalent binding of the biotinylated probe to the streptavidin. By "covalent binding" and grammatical equivalents herein is meant that the two moieties, the solid support and the probe, are attached by at least one bond, including sigma bonds, pi bonds and coordination bonds. Covalent bonds can be formed directly between the probe and the solid support or can be formed by a cross linker or by inclusion of a specific reactive group on either the solid support or the probe or both molecules. Immobilization may also involve a combination of covalent and non-covalent interactions.

In general, the probes are attached to the biochip in a wide variety of ways, as will be appreciated by those in the art. As described herein, the nucleic acids can either be synthesized first, with subsequent attachment to the biochip, or can be directly synthesized on the biochip.

The biochip comprises a suitable solid substrate. By "substrate" or "solid support" or other grammatical equivalents herein is meant any material that can be modified to contain discrete individual sites appropriate for the attachment or association of the nucleic acid probes and is amenable to at least one detection method. As will be appreciated by those in the art, the number of possible substrates are very large, and include, but are not limited to, glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses, plastics, etc. In general, the substrates allow optical detection and do not appreciably show fluorescence.

In a preferred embodiment, the surface of the biochip and the probe may be derivatized with chemical functional groups for subsequent attachment of the two. Thus, for example, the biochip is derivatized with a chemical functional group including, but not limited to, amino groups, carboxy groups, oxo groups and thiol groups, with amino groups being particularly preferred. Using these functional groups, the probes can be attached using functional groups on the probes. For example, nucleic acids containing amino groups can be attached to surfaces comprising amino groups, for example using linkers as are known in the art; for example, homo-or hetero-bifunctional linkers as are well known (see 1994 Pierce Chemical Company catalog, technical section on cross-linkers, pages 155-200, incorporated herein by reference). In addition, in some cases, additional linkers, such as alkyl groups (including substituted and heteroalkyl groups) may be used.

In this embodiment, oligonucleotides, corresponding to the nucleic acid probe, are synthesized as is known in the art, and then attached to the surface of the solid support. As will be appreciated by those skilled in the art, either the 5' or 3' terminus may be attached to the solid support, or attachment may be via an internal nucleoside.

In an additional embodiment, the immobilization to the solid support may be very strong, yet non-covalent. For example, biotinylated oligonucleotides can be made, which bind to surfaces covalently coated with streptavidin, resulting in attachment.

Alternatively, the oligonucleotides may be synthesized on the surface, as is known in the art. For example, photoactivation techniques utilizing photopolymerization compounds and techniques are used. In a preferred embodiment, the nucleic acids can be synthesized in situ, using well known photolithographic techniques, such as those described in WO 95/25116; WO 95/35505; U.S. Pat. Nos. 5,700,637 and 5,445,934; and references cited within, all of which are expressly incorporated by reference; these methods of attachment form the basis of the Affimetrix GeneChip™ technology.

"Differential expression," or grammatical equivalents as used herein, refers to both qualitative as well as quantitative differences in the genes' temporal and/or cellular expression patterns within and among the cells. Thus, a differentially expressed gene can qualitatively have its expression altered, including an activation or inactivation, in, for example, a normal versus an apoptotic cell. That is, genes may be turned on or turned off in a particular state, relative to another state. As is apparent to the skilled artisan, any comparison of two or more states can be made. Such a qualitatively regulated gene will exhibit an expression pattern within a state or cell type which is detectable by standard techniques in one such state or cell type, but is not detectable in both. Alternatively, the determination is quantitative in that expression is increased or decreased; that is, the expression of the gene is either upregulated, resulting in an increased amount of transcript, or downregulated, resulting in a decreased amount of transcript. The degree to which expression differs need only be large enough to quantify via standard characterization techniques, such as by use of Affymetrix GeneChip™ expression arrays, Lockhart, Nature Biotechnology 14:1675-1680 (1996), hereby expressly incorporated by reference. Other techniques include, but are not limited to, quantitative reverse transcriptase PCR, Northern analysis and RNase protection.

Though discussed above with respect to transcripts, it will be appreciated by those in the art that this may be done by evaluation at either the gene transcript, or the protein level; that is, the amount of gene expression may be monitored using nucleic acid probes to the DNA or RNA gene transcript, and the quantification of gene expression levels, or, alternatively, the final gene product itself (protein) can be monitored, for example through the use of antibodies to the myosin-1F protein and standard immunoassays (ELISAs, etc.) or other techniques, including mass spectroscopy assays, 2D gel electrophoresis assays, etc.

In another method detection of the mRNA is performed in situ. In this method permeabilized cells or tissue samples are contacted with a detectably labeled nucleic acid probe for sufficient time to allow the probe to hybridize with the target mRNA. Following washing to remove the non-specifically bound probe, the label is detected. For example a digoxygenin labeled riboprobe (RNA probe) that is complementary to the mRNA encoding a Myosin-1F protein is detected by binding the digoxygenin with an anti-digoxygenin secondary antibody and exposed to nitro blue tetrazolium and 5-bromo4-chloro-3-indoyl phosphate.

In another preferred method, expression of myosin-1F protein is determined using in situ imaging techniques employing antibodies to myosin-1F proteins. In this method cells are contacted with from one to many antibodies to the myosin-1F protein(s). Following washing to remove non-specific antibody binding, the presence of the antibody or antibodies is detected. In one embodiment the antibody is detected by incubating with a secondary antibody that contains a detectable label. In another method the primary antibody to the myosin-1F protein(s) contains a detectable label. In another preferred embodiment each one of multiple primary antibodies contains a distinct and detectable label. This method finds particular use in simultaneous screening for a plurality of myosin-1F proteins. The label may be detected in a fluorometer which has the ability to detect and distinguish emissions of different wavelengths. Labels may be detected using a fluorescence microscope which has multiple fluorescence channels. In addition, a fluorescence activated cell sorter (FACS) can be used in this method. As will be appreciated by one of ordinary skill in the art, numerous other histological imaging techniques are useful in the invention and the antibodies can also be used in ELISA, immunoblotting (Western blotting), immunoprecipitation, BIACORE technology, and the like.

In one embodiment, the myosin-1F proteins of the present invention may be used to generate polyclonal and monoclonal antibodies to myosin-1F proteins, which are useful as described herein. Similarly, the myosin-1F proteins can be coupled, using standard technology, to affinity chromatography columns. These columns may then be used to purify myosin-1F antibodies. In a preferred embodiment, the antibodies are generated to epitopes unique to the myosin-1F protein; that is, the antibodies show little or no cross-reactivity to other proteins. These antibodies find use in a number of applications. For example, the myosin-1F antibodies may be coupled to standard affinity chromatography columns and used to purify myosin-1F proteins as further described below. The antibodies may also be used as blocking polypeptides, as outlined above, since they will specifically bind to the myosin-1F protein.

The anti-myosin-1F protein antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant.

Typically, the immunizing agent and/or adjuvant will be injected in the mammal by multiple subcutaneous or intra-peritoneal injections. The immunizing agent may include the myosin-1F protein or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid a, synthetic trehalose dicorynomycolate). The immunization protocol may be selected by one skilled in the art without undue experimentation.

The anti-myosin-1F protein antibodies may, alternatively, be monoclonal antibodies. Monoclonal antibodies may be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the Myosin-1F protein or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59-103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*. Marcel Dekker, Inc., New York, (1987) pp. 51-63].

The culture medium in which the hybridoma cells are cultured can then be assayed for the presence of monoclonal antibodies directed against myosin-1F protein. Preferably, the binding specificity of monoclonal antibodies produced by the hybridoma cells is determined by immunoprecipitation or by an in vitro binding assay, such as radioimmunoassay (RIA) or enzyme-linked immunosorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein a-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies).

The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

Alternatively, intrabodies may be prepared that are capable of binding to myosin-1F intracellularly. Wirtz et al., Prot. Sci. 8(11):2245-50 (1999); Ohage et al., J. Mol. Biol. 291(5):1129-34 and Ohage et al. J. Biol. Chem. 291(5): 1119-28 (1999), the disclosures of which are expressly incorporated by reference herein. Preferably such intrabodies are lipid soluble and lack a constant region. Intrabodies are particularly useful for the treatment of B-lymphocyte activation disorders, including those associated with myosin-1F dysregulation or dysfunction.

The anti-myosin-1F protein antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann, et al., Nature, 332:323-329 (1988); and Presta, Curr. Op. Struct. Biol. 2593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., Nature, 321:522-525 (1986); Riechmann et al., Nature, 332:323-327 (1988); Verhoeyen et al., Science, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol. 227:381 (1991); Marks et al., J. Biol. 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10 779-783 (1992); Lonberg et al., Nature 368,856-859 (1994); Morrison, Nature 368, 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995).

Bispecific antibodies are monoclonal, preferably human or humanized, antibodies that have binding specificities for at least two different antigens. In the present case, one of the binding specificities is for the myosin-1F protein, the other one is for any other antigen, and preferably for a cell-surface protein or receptor or receptor subunit, preferably for a protein on the surface of a dysregulated or dysfunctional B-lymphocyte or platelet.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, Nature, 305:537-539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., *EMBO J.,* 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al:, *Methods in Enzymoloqy,* 121:210 (1986).

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

The anti-myosin-1F protein antibodies of the invention have various utilities. For example, anti-myosin-1F protein antibodies may be used in diagnostic assays for a myosin-1F protein, e.g., detecting its expression in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: a Manual of Techniques*, CRC Press, Inc. (1987) pp. 147-158]. The antibodies used in the diagnostic assays can be labeled with a detectable moiety. The detectable moiety should be capable of producing, either directly or indirectly, a detectable signal. For example, the detectable moiety may be a radioisotope, such as $^3H$, $^{14}C$, $^{32}P$, $^{35}S$, or $^{25}I$, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature,* 144:945 (1962); David et al., *Biochemistry,* 13:1014 (1974); Pain et al., *J. Immunol. Meth.,* 40:219 (1981); and Nygren, *J. Histochem. and Cytochem.,* 30:407 (1982).

Anti-myosin-1F protein antibodies also are useful for the affinity purification of myosin-1F protein from recombinant cell culture or natural sources. In this process, the antibodies against myosin-1F protein are immobilized on a suitable support, such a Sephadex resin or filter paper, using methods well known in the art. The immobilized antibody then is contacted with a sample containing the myosin-1F protein to be purified, and thereafter the support is washed with a suitable solvent that will remove substantially all the material in the sample except the myosin-1F protein, which is bound to the immobilized antibody. Finally, the support is washed with another suitable solvent that will release the myosin-1F protein from the antibody.

The anti-myosin-1F protein antibodies may also be used in treatment. In one embodiment, the genes encoding the antibodies are provided, such that the antibodies bind to and modulate the myosin-1F protein within the cell.

In one embodiment, anti-myosin-1F antibodies provided herein are capable of reducing or eliminating myosin-1F bioactivity. These antibodies are sometimes referred to herein as function-blocking or function-inhibiting antibodies.

In another embodiment, anti-myosin-1F antibodies provided herein are capable of increasing or enhancing myosin-1F bioactivity. These antibodies are sometimes referred to herein as function-activating antibodies.

In one embodiment, a therapeutically effective dose of a myosin-1F protein, agonist or antagonist is administered to a patient. By "therapeutically effective dose" herein is meant a dose that produces the effects for which it is administered. The exact dose will depend on the purpose of the treatment, and will be ascertainable by one skilled in the art using known techniques. As is known in the art, adjustments for myosin-1F protein degradation, systemic versus localized delivery, as well as the age, body weight, general health, sex, diet, time of administration, drug interaction and the severity of the condition may be necessary, and will be ascertainable with routine experimentation by those skilled in the art.

A "patient" for the purposes of the present invention includes both humans and other animals, particularly mammals. Thus the methods are applicable to both human therapy and veterinary applications. In the preferred embodiment the patient is a mammal, and in the most preferred embodiment the patient is human.

The administration of the myosin-1F protein, agonist or antagonist of the present invention can be done in a variety of ways, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds and inflammation, the composition may be directly applied as a solution or spray. Depending upon the manner of introduction, the compounds may be formulated in a variety of ways. The concentration of therapeutically active compound in the formulation may vary from about 0.1-100% wt.

The pharmaceutical compositions of the present invention comprise a myosin-1F protein, agonist or antagonist (including antibodies and bioactive agents as described herein, most preferably small molecule chemical compositions as described herein) in a form suitable for administration to a patient. In the preferred embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol. Additives are well known in the art, and are used in a variety of formulations.

Combinations of the compositions may be administered. Moreover, the compositions may be administered in combination with other therapeutics, including growth factors or chemotherapeutics and/or radiation. Targeting agents (i.e. ligands for receptors on cancer cells) may also be combined with the compositions provided herein.

In one embodiment provided herein, the antibodies are used for immunotherapy, thus, methods of immunotherapy are provided. By "immunotherapy" is meant treatment of myosin-1F protein related disorders with an antibody raised against a myosin-1F protein. Immunotherapy may also be used to treat lymphocyte disorders not associated with myosin-1F, but treatable by myosin-1F modulation. As used herein, immunotherapy can be passive or active. Passive immunotherapy, as defined herein, is the passive transfer of antibody to a recipient (patient). Active immunization is the induction of antibody and/or T-cell responses in a recipient (patient). Induction of an immune response can be the consequence of providing the recipient with a myosin-1F protein antigen to which antibodies are raised. As appreciated by one of ordinary skill in the art, the myosin-1F protein antigen may be provided by injecting a myosin-1F protein against which antibodies are desired to be raised into a recipient, or contacting the recipient with a myosin-1F nucleic acid, capable of expressing the myosin-1F protein antigen, under conditions for expression of the myosin-1F protein antigen.

In a preferred embodiment, a therapeutic compound is conjugated to an antibody, preferably a myosin-1F protein antibody. The therapeutic compound may be a cytotoxic agent. In this method, targeting the cytotoxic agent to apoptotic cells or tumor cells results in a reduction in the number of afflicted cells, thereby reducing symptoms associated with apoptosis or cancer. Cytotoxic agents are numerous and varied and include, but are not limited to, cytotoxic drugs or toxins or active fragments of such toxins. Suitable toxins and their corresponding fragments include diptheria A chain, exotoxin A chain, ricin A chain, abrin A chain, curcin, crotin, phenomycin, enomycin and the like. Cytotoxic agents also include radiochemicals made by conjugating radioisotopes to antibodies raised against myosin-1F proteins, or binding of a radionuclide to a chelating agent that has been covalently attached to the antibody.

In a preferred embodiment, myosin-1F protein genes are administered as DNA vaccines, either single nucleic acids or combinations of myosin-1F protein genes. Naked DNA vaccines are generally known in the art; see Brower, Nature Biotechnology 16:1304-1305 (1998). Methods for the use of nucleic acids as DNA vaccines are well known to one of ordinary skill in the art, and include placing a myosin-1F protein gene or portion of a myosin-1F protein nucleic acid under the control of a promoter for expression in a patient. The myosin-1F protein gene used for DNA vaccines can encode full-length myosin-1F proteins, but more preferably encodes portions of the myosin-1F proteins including peptides derived from the myosin-1F protein. In a preferred embodiment a patient is immunized with a DNA vaccine comprising a plurality of nucleotide sequences derived from a myosin-1F protein gene. Similarly, it is possible to immunize a patient with a plurality of myosin-1F protein genes or portions thereof, as defined herein. Without being bound by theory, following expression of the polypeptide encoded by the DNA vaccine, cytotoxic T-cells, helper T-cells and antibodies are induced which recognize and destroy or eliminate cells expressing myosin-1F proteins.

In a preferred embodiment, the DNA vaccines include a gene encoding an adjuvant molecule with the DNA vaccine. Such adjuvant molecules include cytokines that increase the immunogenic response to the myosin-1F protein encoded by the DNA vaccine. Additional or alternative adjuvants are known to those of ordinary skill in the art and find use in the invention.

The invention also includes the use of myosin-1F protein compositions, myosin-1F agonists, or myosin-1F antibodies, in the preparation of a medicament for the treatment of lymphocyte activation disorders and lymphocyte proliferation disorders.

All references cited herein are expressly incorporated by reference in their entirety. Moreover, all sequences displayed, cited by reference or accession number in the references are incorporated by reference herein.

We claim:

1. A method of screening for an agent that modulates B-lymphocyte activation, comprising:
    a) combining a candidate bioactive agent and a myosin-1F protein, wherein the sequence of said myosin-1F protein is at least 95% identical to SEQ ID NO:2, and wherein the myosin-1F protein has an activity selected from the group consisting of an ATPase activity, an actin polymerization activity, and a binding activity selected from the group consisting of WASP binding activity, BLNK binding activity, WASP-IP binding activity, Bee1p binding activity, Vrp1p binding activity, calmodulin binding activity, Arp2/3 complex binding activity, Acan125 binding activity, and actin binding activity;
    b) measuring the selected activity of said myosin-1F protein in the presence of said candidate bioactive agent;
    c) contacting said candidate bioactive agent to a B-lymphocyte;
    d) inducing activation of said B-lymphocyte; and
    e) determining the activation of said B-lymphocyte in the presence of said candidate bioactive agent;
    wherein a decrease in the activity of said myosin-1F protein in the presence of said candidate bioactive agent, as compared with the activity of said myosin-1F protein in the absence of said candidate bioactive agent, indicates that said candidate bioactive agent modulates the level of myosin-1F activity, and wherein a decrease in the activation of said B-lymphocyte in the presence of said candidate bioactive agent as compared with activation of said B-lymphocyte in the absence of said candidate bioactive agent indicate that said candidate bioactive agent modulates B-lymphocyte activation.

2. The method of claim 1, wherein the activation of said lymphocyte is determined by measuring CD23 expression.

3. The method of claim 1, wherein the activation of said lymphocyte is determined by measuring expression of a lymphocyte surface marker selected from CD23, CD69, CD80, and CD86.

4. The method of claim 1, wherein the activation of said lymphocyte is determined by measuring promoter activity of a promoter selected from the group consisting of an IL-2 promoter and an immunoglobulin heavy chain gene promoter.

5. The method of claim 1, wherein the activation of said lymphocyte is determined by measuring intracellular calcium concentration.

6. The method of claim 1, wherein said myosin-1F protein consists of the amino acid sequence set forth in SEQ ID NO:2.

7. The method of claim 1, further comprising:
    f) contacting said candidate bioactive agent to a T-lymphocyte;
    g) inducing activation of said T-lymphocyte; and h) determining the activation of said T-lymphocyte in the presence of said candidate bioactive agent;

wherein said candidate bioactive agent modulates activation of the B-lymphocyte, but does not modulate activation of a T lymphocyte.

8. The method of claim 1, wherein the myosin-1F activity measured is selected from the group consisting of WASP binding activity, BLNK binding activity, WASP-IP binding activity, Bee1p binding activity, Vrp1p binding activity, Arp2/3 complex binding activity, and Acan125 binding activity.

\* \* \* \* \*